US011242515B2

United States Patent
Dong et al.

(10) Patent No.: US 11,242,515 B2
(45) Date of Patent: Feb. 8, 2022

(54) METHOD FOR PURIFICATION AND ACTIVATION OF BOTULINUM NEUROTOXIN

(71) Applicant: President and Fellows of Harvard College, Cambridge, MA (US)

(72) Inventors: Min Dong, Weatogue, CT (US); Sulyman Barkho, Jamaica Plain, MA (US); Liang Tao, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/302,088

(22) PCT Filed: May 16, 2017

(86) PCT No.: PCT/US2017/032985
§ 371 (c)(1),
(2) Date: Apr. 12, 2019

(87) PCT Pub. No.: WO2017/201105
PCT Pub. Date: Nov. 23, 2017

(65) Prior Publication Data
US 2019/0153418 A1     May 23, 2019

Related U.S. Application Data

(60) Provisional application No. 62/336,958, filed on May 16, 2016.

(51) Int. Cl.
*C12N 9/52* (2006.01)
*C07K 14/33* (2006.01)

(52) U.S. Cl.
CPC .............. *C12N 9/52* (2013.01); *C07K 14/33* (2013.01); *C12Y 304/24069* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 4,703,004 A | 10/1987 | Hopp et al. | |
| 4,851,341 A | 7/1989 | Hopp et al. | |
| 5,011,912 A | 4/1991 | Hopp et al. | |
| 5,284,933 A | 2/1994 | Dobeli et al. | |
| 5,310,663 A | 5/1994 | Dobeli et al. | |
| 5,654,176 A | 8/1997 | Smith | |
| 6,013,462 A | 1/2000 | Kauvar et al. | |
| 6,303,128 B1 | 10/2001 | Webb et al. | |
| 7,189,541 B2 | 3/2007 | Donovan | |
| 7,985,554 B2* | 7/2011 | Chapman | A61P 39/02 435/7.1 |
| 8,128,940 B2* | 3/2012 | Steward | A61P 9/00 424/239.1 |
| 8,137,924 B2* | 3/2012 | Chapman | C12Y 304/24069 435/7.32 |
| 8,450,277 B2* | 5/2013 | Chapman | A61P 39/00 514/17.7 |
| 8,623,999 B2* | 1/2014 | Steward | A61P 25/04 530/350 |
| 8,771,707 B2* | 7/2014 | Chapman | C07K 14/705 424/239.1 |
| 8,987,208 B2* | 3/2015 | Chapman | A61P 39/02 514/17.7 |
| 8,999,649 B2* | 4/2015 | Chapman | C07K 14/705 435/6.15 |
| 9,598,685 B2* | 3/2017 | Dong | A61P 1/06 |
| 10,190,110 B2* | 1/2019 | Dong | A61P 19/00 |
| 2009/0053248 A1* | 2/2009 | Simpson | A61K 47/6415 424/183.1 |
| 2012/0178140 A1* | 7/2012 | Steward | A61P 5/00 435/188 |
| 2015/0166972 A1 | 6/2015 | Dong et al. | |
| 2019/0153418 A1* | 5/2019 | Dong | C12Y 304/24069 |

FOREIGN PATENT DOCUMENTS

| | | |
|---|---|---|
| EP | 2524963 A1 | 11/2012 |
| JP | 2010-037253 A | 2/2010 |
| JP | 2010-249840 A | 11/2010 |
| WO | WO-95/33850 A1 | 12/1995 |
| WO | WO-2017/201105 A1 | 11/2017 |

OTHER PUBLICATIONS

Hasegawa et al, The Protein Journal, Aug. 2004, 23/6:371-378 (Year: 2004).*
Kouguchi et al, Eur. J. Biochem, 2001, 268:4019-4026 (Year: 2001).*
Lee et al. Abstracts/Toxicon 93(2015) Abstract# 128, pp. S39-S40 (Year: 2015).*
Matsui e tal, J.Mol. Biol., 2014, 426:3773-3785 (Year: 2014).*
Matsuo et al, FEMS Immunol Med Microbiol, 2011, 63:35-43 (Year: 2011).*
Nakamura et al, J. Moi. Biol, 2009, 385:1193-1206. Available online: Nov. 27, 2008 (Year: 2009).*
Sugawara etal, PLoS ONE 9 (10): e111170. https://doi.org/10.1371/journal.pone.0111170. 2014 Published: Oct. 23, 2014 (Year: 2014).*

(Continued)

*Primary Examiner* — Nita M. Minnifield
(74) *Attorney, Agent, or Firm* — Choate, Hall & Stewart LLP; Brenda Herschbach Jarrell; Rebekah Z. Kitto

(57) ABSTRACT

Disclosed herein are methods for the isolation and purification of a botulinum neurotoxin (BoNT) protein, or a polypeptide comprising a receptor binding domain of BoNT, from a solution. The method comprises contacting the solution containing the protein or polypeptide to a matrix which has attached thereto a non-toxic non-hemagglutinin (NTNHA) under conditions appropriate for binding, washing the matrix to thereby remove unbound materials, and eluting the protein or polypeptide with a solution that dissociates the bound protein from the NTNHA. Conditions appropriate for binding are a pH of less than 7.5 (e.g, 6). Conditions appropriate for dissociation are a pH greater than or equal to 7.5 (e.g., 8). Compositions specific to the methods are also disclosed.

20 Claims, 13 Drawing Sheets
Specification includes a Sequence Listing.

(56) References Cited

OTHER PUBLICATIONS

Terilli et al. BMC Microbiology 2011, 11:232 http://www.biomedcentral.com/1471-2180/11/232, 12 pages (Year: 2011).*
Fujinaga et al, FEBS Letter, 467,(200), 179-183 (Year: 2000).*
Ma. Aug. 2010. pp. 137143 (Year: 2010).*
Yamashit et al. FEBS Letters586 (2012) pp. 2404-2410. Available online: Jun. 7, 2012 (Year: 2012).*
Miyata et al. Biochemical and Biophysical Research Communications. 2009, 384:126-130. Available online: Apr. 24, 2009 (Year: 2009).*
Blasi, J et al., Botulinum neurotoxin A selectively cleaves the synaptic protein SNAP-25, Nature, 365(6442):160-3 (1993).
Bonventre P. and Kempe, L., Physiology of toxin production by Clostridium botulinum types A and B. III. Effect of pH and temperature during incubation on growth, autolysis, and toxin production, Appl Microbiol., 7:374-7 (1959).
Borjigin, J. and Nathans, J., Insertional mutagenesis as a probe of rhodopsin's topography, stability, and activity, J Biol Chem., 269(20):14715-22 (1994).
Brizzard, B. et al., Immunoaffinity purification of FLAG epitope-tagged bacterial alkaline phosphatase using a novel monoclonal antibody and peptide elution, Biotechniques, 16(4):730-5 (1994).
Dasgupta, B. and Boroff, D., Chromatographic isolation of hemagglutinin-free neurotoxin from crystalline toxin of Clostridium botulinum type A, Biochim Biophys Acta., 147(3):603-5 (1967).
Dent, P., et al., Regulation of Raf-1 and Raf-1 mutants by Ras-dependent and Ras-independent mechanisms in vitro, Mol Cell Biol., 15(8):4125-35 (1995).
Dipaolo, G. et al., Targeting of SCG10 to the area of the Golgi complex is mediated by its NH2-terminal region, J Biol Chem., 272(8):5175-82 (1997).
Dong, M. et al., SV2 is the protein receptor for botulinum neurotoxin A, Science, 312(5773):592-6 (2006).
Duff J. et al., Studies on immunity to toxins of Clostridium botulinum. I. A simplified procedure for isolation of type A toxin, J Bacteriol., 73(1):42-7 (1957).
Duff, J. et al., Studies on immunity to toxins of Clostridium botulinum. II. Production and purification of type B toxin for toxoid, J Bacteriol., 73(5):597-601 (1957).
Evan, G. et al., Isolation of monoclonal antibodies specific for human c-myc proto-oncogene product, Mol Cell Biol., 5(12):3610-6 (1985).
Field, J. et al., Purification of a RAS-responsive adenylyl cyclase complex from *Saccharomyces cerevisiae* by e of an epitope addition method, Mol Cell Biol., 8(5):2159-65 (1988).
Finzi, E. and Rosenthal, N., Treatment of depression with onabotulinumtoxinA: a randomized, double-blind, placebo controlled trial, J Psychiatr Res., 52:1-6 (2014).
Goldstein, D. et al., The BPV-1 E5 oncoprotein expressed in Schizosaccharomyces pombe exhibits normal biochemical properties and binds to the endogenous 16-kDa component of the vacuolar proton-ATPase, Virology, 190(2):889-93 (1992).
Grussenmeyer, T. et al., Complexes of polyoma vir medium T antigen and cellular proteins, Proc Natl Acad Sci A, 82(23):7952-4 (1985).
Gu, S. et al., Botulinum Neurotoxin Is Shielded by NTNHA in an Interlocked Complex, Science, 335:977-981 (2012).
Hexsel, C. et al., Botulinum toxin type A for aging face and aesthetic uses, Dermatol Ther., 24(1):54-61 (2011).
International Search Report for PCT/US2017/032985, 6 pages (dated Sep. 7, 2017).
Jackson, J. et al., Botulinum toxin A for prophylactic treatment of migraine and tension headaches in adults: a meta-analysis, JAMA, 307(16):1736-45 (2012).
Jankovic, J. and Brin, M., Therapeutic uses of botulinum toxin, N Engl J Med., 324(17):1186-94 (1991).
Jekel, P. et al., Use of endoproteinase Lys-C from Lysobacter enzymogenes in protein sequence analysis, Anal Biochem., 134(2):347-54 (1983).
Jiang, Y. et al., Current and potential urological applications of botulinum toxin A, Nat Rev Urol., 12(9):519-33 (2015).
Kassera, H. and Laidler, K., pH Effects in trypsin catalysis, Canadian Journal of Chemistry, 47(21):4021-4029 (1969).
Koralnik, I. et al., The p12I, p13II, and p30II proteins encoded by human T-cell leukemia/lymphotropic vir type I open reading frames I and II are localized in three different cellular compartments, J Virol., 67(4):2360-6 (1993).
Kreis, T.E., Microinjected antibodies against the cytoplasmic domain of vesicular stomatitis vir glycoprotein block its transport to the cell surface, EMBO J., 5(5):931-41 (1986).
Lacy, D. et al., Crystal structure of botulinum neurotoxin type A and implications for toxicity, Nat Struct Biol., 5(10):898-902 (1998).
Lee, J. et al., A protein kinase involved in the regulation of inflammatory cytokine biosynthesis, Nature, 372(6508):739-46 (1994).
Lee, K., et al., Molecular basis for disruption of E-cadherin adhesion by botulinum neurotoxin A complex, Science, 344(6190):1405-10 (2014).
Liang, T. et al., Antibody binding to a peptide but not the whole protein by recognition of the C-terminal carboxy group, Arch Biochem Biophys., 329(2):208-14 (1996).
Lietzow, M. et al., Composition and Molecular Size of Clostridium botulinum Type A Toxin-Hemagglutinin Complex, Protein J., 28:250-251 (2009).
Lim, P. et al., Distribution and specific identification of papillomavirus major capsid protein epitopes by immunocytochemistry and epitope scanning of synthetic peptides, Infect Dis., 162(6):1263-9 (1990).
Luo, W. et al., A universal tag for recombinant proteins, Arch Biochem Biophys., 329(2):215-20 (1996).
MacArthur, H. and Walter, G., Monoclonal antibodies specific for the carboxy termin of simian vir 40 large T antigen, J Virol., 52(2):483-91 (1984).
Malizio, C. et al., Purification of Clostridium botulinum type A neurotoxin, Methods Mol Biol., 145:27-39 (2000).
Martin, G.A., The GAP-related domain of the neurofibromatosis type 1 gene product interacts with ras p21, Cell, 63(4):843-9 (1990).
Masuyer, G. et al., Engineered botulinum neurotoxins as new therapeutics, Annu Rev Pharmacol Toxicol., 54:27-51 (2014).
Miyata, K. et al., Expression and stability of the nontoxic component of the botulinum toxin complex, Biochemical and Biophysical Research Communications, 384:126-130 (2009).
Miyata, K. et al., Purification and Characterization of Nontoxic Protein Complex from Serotype D 4947 Botulinum Toxin Complex, Protein J., 31:387-392 (2012).
Montal, M., Botulinum neurotoxin: a marvel of protein design, Annu Rev Biochem., 79:591-617 (2010).
Munro, S. and Pelham, H., A C-terminal signal prevents secretion of luminal ER proteins, Cell, 48(5):899-907 (1987).
Pickett, A. and Perrow, K., Composition and molecular size of Clostridium botulinum Type A toxin-hemagglutinin complex, Protein J., 28(5):248-9; discsion 250-1 (2009).
Pickett, A., Botulinum Toxin as a Clinical Product: Manufacture and Pharmacology. In Clinical Applications of Botulinum Neurotoxin, Current Topics in Neurotoxicity, Springer New York, pp. 7-49 (2014).
Ritchie, P. et al., Baculovir expression and biochemical characterization of the human microsomal triglyceride transfer protein, Biochem J., 338(Pt 2):305-10 (1999).
Rossetto, O. et al., Botulinum neurotoxins: genetic, structural and mechanistic insights, Nat Rev Microbiol., 12(8):535-49 (2014).
Roth, M. et al., A conserved family of nuclear phosphoproteins localized to sites of polymerase II transcription, J Cell Biol., 115(3):587-96 (1991).
Rubinfeld, B. et al., Molecular cloning of a GTPase activating protein specific for the Krev-1 protein p21rap1, Cell, 65(6):1033-42 (1991).
Sagane, Y. et al., Spontaneous nicking in the nontoxic-nonhemagglutinin component of the Clostridium botulinum toxin complex, Biochem Biophys Res Commun., 292(2):434-40 (2002).
Schantz, E. and Johnson, E., Properties and use of botulinum toxin and other microbial neurotoxins in medicine, Microbiol Rev., 56(1):80-99 (1992).

(56) References Cited

OTHER PUBLICATIONS

Shenyan et al., Science 335: 977-981 (2012).

Smith, D.J., Mini-exon epitope tagging for analysis of the protein coding potential of genomic sequence, Biotechniques, 23(1):116-20 (1997).

Snipe, P. and Sommer, H., Studies on botulin toxin 3. Acid precipitation of botulin toxin, The Journal of infectious diseases, 43(2):452-160 (1928).

Studier, F., Protein production by auto-induction in high density shaking cultures, Protein Expr Purif., 4(1):207-34 (2005).

Truong, D. and Jost, W., Botulinum toxin: clinical use, Parkinsonism Relat Disord., 12(6):331-55 (2006).

Tse, C. et al., Preparation and characterisation of homogeneous neurotoxin type A from Clostridium botulinum. Its inhibitory action on neuronal release of acetylcholine in the absence and presence of beta-bungarotoxin, Eur J Biochem., 122(3):493-500 (1982).

Turner, J. et al., Carboxy-terminal vesicular stomatitis vir G protein-tagged intestinal Na+-dependent glucose cotransporter (SGLT1): maintenance of surface expression and global transport function with selective perturbation of transport kinetics and polarized expression, J Biol Chem., 271(13):7738-44 (1996).

Visco, A. et al., Anticholinergic therapy vs. onabotulinumtoxinA for urgency urinary incontinence., N Engl J Med., 367(19):1803-13 (2012).

Weetall, H.H., Covalent coupling methods for inorganic support materials, Methods Enzymol., 44:134-48 (1976).

Weetall, Howard H., Preparation of Immobolized Proteins Covalently Coupled Through Silane Coupling Agents to Inorganic Supports, Adv. Mol. Cell Bio., 15A:161-192 (2008).

Wilson, I. et al., The structure of an antigenic determinant in a protein, Cell, 37(3):767-78 (1984).

Written Opinion for PCT/US2017/032985, 8 pages (dated Sep. 7, 2017).

Xu, T. and Rubin, G., Analysis of genetic mosaics in developing and adult *Drosophila* tissues, Development, 117(4):1223-37 (1993).

Xu, Y. et al., E1A-mediated repression of progesterone receptor-dependent transactivation involves inhibition of the assembly of a multisubunit coactivation complex, Mol Cell Biol., 20(6):2138-46 (2000).

Sagane, Y. et al., Small-angle X-ray scattering reveals structural dynamics of the botulinum neurotoxin associating protein, nontoxic nonhemagglutinin, Biochemical and Biophysical Research Communications, 425:256-260 (2012).

\* cited by examiner

NTNHA A1:  Clostridium botulinum A str. ATCC 350. (YP_001253341.1) (SEQ ID NO: 22)

```
   1 mnindnlsin spvdnknvvv vrarktdtvf kafkvapniw vaperyyges lsideeykvd
  61 ggiydsnfls qdsekdkflq aiitllkrin stnagekllr listaipfpy gyigggyyap
 121 nmitfgsapk snkklnslis stipfpyagy retnylssed nksfyasniv ifgpganive
 181 nntvfykked aengmgtmte iwfqpfltyk ydefyidpai elikcliksl yflygikpsd
 241 dlvipyrlrs elenieysql nivdllvsgg idpkfintdp ywftdnyfsn akkvfedhrn
 301 iyeteiegnn aigndiklrl kqkfrinind iwelnlnyfs kefsimmpdr fnnalkhfyr
 361 kqyykidype nysingfvng qinaqlslsd rnqdiinkpe eiinllngnn vslmrsniyg
 421 dglkstvddf ysnykipynr ayeyhfnnsn dssldnvnig vidnipeiid vnpykencdk
 481 fspvqkitst reintnipwp inylqaqntn nekfslssdf vevvsskdks lvysflsnvm
 541 fyldsikdns pidtdkkyyl wlreifrnys fditatqein tncginkvvt wfgkalniln
 601 tsdsfveefq nlgaislink kenlsmpiie syeipndmlg lplndlnekl fniyskntay
 661 fkkiyynfld qwwtqyysqy fdlicmakrs vlaqetlikr iiqkklsyli gnsnissdnl
 721 almnltttnt lrdisnesqi amnnvdsfln naaicvfesn iypkfisfme qcinninikt
 781 kefiqkctni nedeklqlin qnvfnsldfe flniqnmksl fssetallik eetwpyelvl
 841 yafkepgnnv igdasgknts ieyskdiglv yginsdalyl ngsnqsisfs ndffengltn
 901 sfsiyfwlrn lgkdtikskl igskedncgw eiyfqdtglv fnmidsngne kniylsdvsn
 961 nswhyitisv drlkeqllif iddnlvanes ikeilniyss niisllsenn psyiegltil
1021 nkpttsqevl snyfevlnns yirdsneerl eynktyqlyn yvfsdkpice vkqnnniylt
1081 inntnnlnlq askfkllsin pnkqyvqkld eviisvldnm ekyidisedn rlqlidnknn
1141 akkmiisndi fisncltlsy ngkyiclsmk denhnwmicn ndmskylylw sfk
```

FIG. 5A

NTNHA A2:   Clostridium botulinum A2 str. Kyoto (WP 012704905) (SEQ ID NO: 23)

```
   1 mkinnnfnid slidnrdvai vrgrktdtff kvfqvapniw iaperyyges lninedqksd
  61 ggiydsnfls tndekdeflq atvkilqrin nnvigaklls listaipfpy eykpgdyrqt
 121 nylvskdnqh yytanlvifg pgtnivenna iyykkedsen gmgtmseiwf qpfltykygq
 181 fyvdpaleli kclikslyyl ygikpsddls ipyrlrseln sfeyseldmi dflisggtey
 241 klldtnpywf tdnyfidapk nfekykndye tkiknnndia nsiklyleqk fktnaqdiwe
 301 lnlsyfstef eimmpeifnn alnhyyrkey yvidyfknyn ingfingqik tilplskynk
 361 niinkpelvv nlinenntvl mksnvygdgl kgtmdnfyaa ykipynigde yhinysylnn
 421 vnveeinnip pindadiypy rknsdpfipv ynitetkein tttplsvnyl qaqvtnsndi
 481 slsssdfskvi sskdrslvys fldntidyld sikydepidt dkkyylwlke ifrnysfdmt
 541 etqevntpcg inkvvpwlgk alnilntgns fieefkslgp islinkkeni tmpkieidei
 601 pnsmlnlsfk dlsenlfnrf sknnsyfeki yydfldqwwt qyysqyfdli cmakksilaq
 661 etlikkiiqk klsylignsn issdnlalmn ltttntlrdi snesqiamnn vdsflnsaai
 721 cvfegniysk fisfmeqcin ninkntrefi qkctnitene klqlinqnif ssldfdflni
 781 enlkslfsse tallikeets pyelvlyafq epdnnaigda sakntsieys kdidlvygin
 841 sdalylngsn qsisfsndff engltnsfsi yfwlrnlgkd tiskkligsk edncgweiyf
 901 qdtglvfnmi dsngnekniy lsdvsnnswh yitisvdrlk eqllifiddn lvanesikei
 961 lniyssniis llsennpsyi egltilnkpt tsqevlnnyf kvlnnsyird sneerleynk
1021 tyqlynyvfs dkpicevkqn nniyltinnt nnlnlqpskf kllsinsnkq yvqkfdevii
1081 silgnmekyi disednrlql idnkngakkm iisndmfisn cltlscggky iclsmkdenh
1141 nwmicnndms kylylwsfk
```

FIG. 5B

NTNHA B:  Clostridium botulinum B1 str. Okra (WP 003404192.1) (SEQ ID NO: 24)

```
   1 mnindnlsin spvdnknvvv vrarktdtvf kafkvapniw vaperyyges lsideeykvd
```

FIG. 5C

```
  61 ggiydsnfls qdsekdkflq aiitllkrin stnageklls listaipfpy gyigggyyap
 121 nmitfgsapk snkklnslis stipfpyagy retnylssed nksfyasniv ifgpganive
 181 nntvfykked aengmgtmte iwfqpfltyk ydefyidpai elikcliksl yflygikpsd
 241 dlvipyrlrs elenieysql nivdllvsgg idpkfintdp ywftdnyfsn akkvfedhrn
 301 iyetqiegnn aigndiklrl kqkfrinind iwelnlnyfs kefsimmpdr fnnalkhfyr
 361 kqyykidype nysingfvng qinvqlslsd rnqdiinkpe eiinllngnn vslmrsniyg
 421 dglkstvddf ysnykipynr ayeyhfnnsn dssldnvnig vidnipeiid vnpykencdk
 481 fspvqkitst reintnipwp inylqaqntn nekfslssdf vevvsskdks lvysflsnvm
 541 fyldsikdns pidtdkkyyl wlreifrnys fditatqein tdcginkvvt wfgkalniln
 601 tsdsfveefq nlgpislink kenlsmpiie iygipndmlg lplndlnekl fniylknily
 661 fkkvyfnfld qwwteyysqy fdlicmakqs ilaqeklikq iiqnklqdlf kadismdkln
 721 lmnlatektf idlsnesqia innindflnk saicvfdtni ypkfisfmeq cinsvnsnvt
 781 afiqkctnit edeklqlikl ntfmnidfef fdiqsikdli tsetdlikee kesdynlflf
 841 tlqednnkvi edisgkntlv kysdsislvy gvngdalylk epdesvsfsn kafengltns
 901 fsicfwlrnl gediitskli enkadncgwe iyfennglvf sivdcngnee niylsdvisk
 961 nwyyisisid rlrnqllifi ndkliangsi eqilniyssn tislvnennp iyieglsiln
1021 rsitseevvn nyfsylnnsy irdisgerle ynktyelyny vfpenslyev tennniylsi
1081 kdtnnlniqg akfklinida nkqyvqkwde gvvcllgdee kyvdissenn riqlvnskdt
1141 akriifnndi fmpncltfay nnkylslslr drnynwmicn nndnipkaah lwalkgi
```

FIG. 5C Continued

NTNHA C1: Clostridium botulinum C1 (YP 398515.1) (SEQ ID NO: 25)

```
MDINDDLNIN SPVDNKNVVI VRARKTNTFF KAFKVAPNIW VAPERYYGEP LDIAEEYKLD
GGIYDSNFLS QDSERENFLQ AIIILLKRIN NTISGKQLLS LISTAIPFPY GYIGGGYSSP
NIFTFGKTPK SNKKLNSLVT STIPFPFGGY RETNYIESQN NKNFYASNII IFGPGSNIVE
NNVIYYKKND AENGMGTMAE IVFQPLLTYK YNKFYIDPAM ELTKCLIKSL YFLYGIKPSD
NLVVPYRLRT ELDNKQFSQL NIIDLLISGG VDLEFINTNP YWFTNSYFPN SIKMFEKYKN
IYKTEIEGNN AIGNDIKLRL KQKFQINVQD IWNLNLNYFC QSFNSIIPDR FSNALKHFYR
KQYYTMDYTD NYNINGFVNG QINTKLPLSN KNTNIISKPE KVVNLVNENN ISLMKSNIYG
DGLKGTTEDF YSTYKIPYNE EYEYRFNDSD NFPLNNISIE EVDSIPEIID INPYKDNSDN
LVFTQITSMT EEVTTHTALS INYLQAQITN NENFTLSSDF SKVVSSKDKS LVYSFLDNLM
SYLETIKNDG PIDTDKKYYL WLKEVFKNYS FDINLTQEID SMCGINEVVL WFGKALNILN
TSNSFVEEYQ DSGAISLISK KDNLREPNIE IDDISDSLLG LSFKDLNNKL YEIYSKNIVY
FKKIYFSFLD QWWTEYYSQY FELICMAKQS ILAQESLVKQ IVQNKFTDLS KASIPPDTLK
LIRETTEKTF IDLSNESQIS MNRVDNFLNK ASICVFVEDI YPKFISYMEK YINNINIKTR
EFIQRCTNIN DNEKSILINS YTFKTIDFKF LDIQSIKNFF NSQVEQVMKE ILSPYQLLLF
ASKGPNSNII EDISGKNTLI QYTESIELVY GVNGESLYLK SPNETIKFSN KFFTNGLTNN
FTICFWLRFT GKNDDKTRLI GNKVNNCGWE IYFEDNGLVF EIIDSNGNQE SVYLSNIIND
NWYYISISVD RLKDQLLIFI NDKNVANVSI DQILSIYSTN IISLVNKNNS IYVEELSVLD
NPITSEEVIR NYFSYLDNSY IRDSSKSLLE YKNYQLYNY VFPETSLYEV NDNNKSYLSL
KNTDGINISS VKFKLINIDE SKVYVQKWDE CIICVLDGTE KYLDISPENN RIQLVSSKDN
AKKITVNTDL FRPDCITFSY NDKYFSLSLR DGDYNWMICN DNNKVPKGAH LWILES
```

FIG. 5D

NTNHA D: Clostridium botulinum D (BAA75083.1) (SEQ ID NO: 26)

```
   1 mdinddlnin spvdnknvvi vrarktntff kafkvapniw vaperyygep ldiaeeykld
  61 ggiydsnfls qdserenflq aiiillkrin ntisgkqlls listaipfpy gyigggyssp
 121 niftfgktpk snkklnslvt stipfpfggy retnyiesqn nknfyasniv ifgpgsnive
 181 nnviyykknd aengmgtmae ivfqplltyk ynkfyidpam eltkcliksl yflygikpsd
 241 nlvvpyrlrt eldnkqfsql niidllisgg vdlefintnp ywftnsyfpn sikmfekykn
 301 iykteiegnn aigndiklrl kqkfqinvqd iwnlnlnyfc qsfnsiipdr fsnalkhfyr
 361 kqyytmdytd nyningfvng qintklplsn kntniiskpe kvvnlvnenn islmksniyg
 421 dglkgstedf ystykipyne eyeyrfndsd nfplnnisie evdsipeiid inpykdnsdn
 481 lvftqitsmt eevtthtals inylqaqitn nenftlssdf skvvsskdks lvysfldnlm
 541 syletikndg pidtdkkyyl wlkevfknys fdinltqeid smcginevvl wfgkalniln
 601 tsnsfveeyq dsgaislisk kdnlrepnie iddisdsllg lsfkdlnnkl yeiysknivy
 661 fkkiyfsfld qwwteyysqy felicmakqs ilaqeslvkq ivqnkftdls kasippdtlk
 721 lirettektf idlsnesqis mnrvdnflnk asicvfvedi ypkfisymek yinniniktr
 781 efiqrctnin dneksilins ytfktidfkf ldiqsiknff nsqveqvmke ilspyqlllf
 841 askgpnsnii edisgkntli qytesielvy gvngeslylk spnetikfsn kfftngltnn
 901 fticfwlrft gknddktrli gnkvnncgwe iyfednglvf eiidsngnqe svylsniind
 961 nwyyisisvd rlkdqllifi ndknvanvsi dqilsiystn iislvnknns iyveelsvld
1021 npitseevir nyfsyldnsy irdssksllc ynknyqlyny vfpetslyev ndnnksylsl
1081 kntdginiss vkfklinide skgyvqkwde ciicvldgte kyldispenn riqlvsskdn
1141 akkitvntdl frpdcitfsy ndkyfslslr dgdynwmicn dnnkvpkgah lwiles
```

FIG. 5E

NTNHA E: Clostridium botulinum type E (WP_003409842) variant (SEQ ID NO: 27)

```
   1 mkingnlnid spvdnknvai vrsrksdvff kafqvapniw iaperyyges lkinedqksd
  61 ggiydsnfls tnnekdeflq atikllqrin nnvvgaklls listaipfpy enntedyrqt
 121 nylssknneh yytanlvifg pgsniiknnv iyykkeyaen gmgtmleiwf qpflthkyde
 181 fyvdpaleli kclikslyyl ygikpndnln ipyrlrnefn sleyseldmi dflisggidy
 241 kllntnpywf idkyfidtsk nfekykndye ikiknnnyia nsiklyleqk fkinvkdiwe
 301 lnlsyfskef qimmperynn alnhyyrkey yvidyfknyn ingfkngqik tklplskynk
 361 eiinkpeliv nlinqnntvl mksniygdgl kgtvdnfysn yiipynlnye hsinysyldn
 421 vnieeiekip pindediypy rknadtfipv ynitkakein tttplpvnyl qaqmidsndi
 481 nlssdflkvi sskgslvysf lnntmdylef ikydkpidtd kkyykwlkai frnysldite
 541 tqeisnqfgd tkiipwigra lnilntnnsf veefknlgpi slinkkenit ipkikideip
 601 ssmlnfsfkd lsenlfniyc knnfylkkiy ynfldqwwtq yysqyfdlic masksvlaqe
 661 klikkliqkq lrylmensni sstnlilinl tttntlrdis nqsqiainni dkffnnaamc
 721 vfenniypkf tsfmeqcikn inkstkefil kctninetek shlimqnsfs nldfdfldiq
 781 nmkklfnsyt ellikeqtsp yelslyafqe qdnnvigdts gkntlveypk diglvyginn
 841 naihltganq nikftndyfe ngltnnfsiy fwlrnlnqnt ikskligske dncgweiyfe
 901 nnglvfniid sngnekniyl snisnkswhy ivisinrlkd qllifidnil vanedikeil
 961 niyssdiisl lsdnnnvyie glsvlnktin sneiltdyfs dlnnsyirnf deeilqynrt
1021 yelfnyvfpe iainkieqnn niylsnnnen slnfkplkfk llntnpnkqy vqkwdevifs
1081 vldgtekyld isidnnriql vdnknnaktf iinndifisn cltltynnvn vylsiknqdy
1141 nwvicdlnhd ipkksylwil kni
```

FIG. 5F

NTNHA F: Clostridium botulinum type F  (YP_001390122.1) (SEQ ID NO: 28)

NTNHA G: clostridium botulinum (Clostridium argentinense) type G ATCC
27322 (CAA61228.1) (SEQ ID NO: 29)

```
   1 mkinsnltin spidnknvvi vraretskff kafkvapniw vaperyyges lsieeskkvn
  61 ggvydsnfls qnnekdkflq aiitllkrin sniageklls lvstaipfpy gyigggyycp
 121 nivtfgstik ynkkinslis ttipfpyggy retnylsskd tenfyaaniv ifgpganive
 181 nntvfykked aengmgtmae icfqpfltyk ydqfyvdpal elmecliksl yflygikpnn
 241 nltvpyrlrn elsniefsql sivdllisgg idskfintdp ywfidsyfsn akttfeehks
 301 iyeteikgnn aigndiklrl kqkfqttvhd iwqlnldyfs kefqimmpyr fnnalkyyyr
 361 keyykidype kysiagfvdg qlntqlslsd knqyiinkpe livnlisenn islmrsniyg
 421 dglkyttdnf ystykipynr ayeyhfnnss tsslenvnve eisnipeiid inpyrensdi
 481 fspveniiet kevntktpwp inylqaqipn neeftlssdf sqvvsyktqs lvysflsnvi
 541 syldsvkdtn pidtdekyyl wlreifrnys fditaieein tscginkvvs wfgkalniln
 601 tsnsfvkefk nlgpislink kenlsmpiie vneipndmlg lslkdlnekl fniylknily
 661 fkkvyfsfld qwwteyysqy fglicmakqs ilaqenlikk ivqkklsdls kqsnisnekl
 721 nlmnlttekt fidlsnqsqi amnninnfln kaaicvfesn iypkfisfme qyinninikt
 781 tafirkctni tekeklqlin qntfnnldfe ffdiqtienl ltsetnliik ektspydlll
 841 fslqeadrkv ikdisgkdtl vqysdtidls ygvngdalyl kepnqsvnfs nnifengltn
 901 sfsicfwlrn lgqdnlssnl ignivnncgw qiyfennglv fsmvdcngne kniylsdvls
 961 kywyyisvsv drlrnkllif indklivnes ieqilniyss niislvnenn picieelsil
1021 nkaltseevl nsyftnlnns yirdsygarl eynknyelyn yvfpenslye viennnmyls
1081 ikniknthil gakfklintd eskqyvqkwd eviicvlgdt ekyadiqagn nriqlvnskd
1141 narkiivnnn ifrpncvlfs ynnkylslsl rnrnynwmic ndnsfipkha hlwilkki
```

FIG. 5H

NTNHA E: Clostridium botulinum type E (WP_012450714.1) (SEQ ID NO: 30)

```
   1 mkingnlnid spvdnknvai vrarksdvff kafqvapniw ivperyyges lkinedqkfd
  61 ggiydsnfls tnnekddflq atikllqrin nnvvgaklls listaipfpy enntedyrqt
 121 nylssknneh yytanlvifg pgsniiknnv iyykkeyaes gmgtmleiwf qpflthkyde
 181 fyvdpaleli kclikslyyl ygikpndnln ipyrlrnefn sleyseldmi dflisggidy
 241 kllntnpywf idkyfidtsk nfekykndye ikiknnnyia nsiklyleqk fkinvkdiwe
 301 lnlsyfskef qimmperynn alnhyyrkey yvidyfknyn ingfkngqik tklplskynk
 361 eiinkpeliv nlinqnntvl mksniygdgl kgtvdnfysn yiipynlnye hsinysyldn
 421 vnieeiekip pindediypy rknadtfipv ynitkakein tttplpvnyl qagmidsndi
 481 nlssdflkvi sskgslvysf lnntmdylef ikydkpidtd kkyykwlkai frnysldite
 541 tqeisnqfgd tkiipwigra lnilntnnsf veefknlgpi slinkkenit ipkikideip
 601 ssmlnfsfkd lsenlfniyc knnfylkkiy ynfldqwwtq yysqyfdlic masksvlaqe
 661 klikkliqkq lrylmensni sstnlililni tttntlrdis nqsqiainni dkffnnaamc
 721 vfenniypkf tsfmeqcikn inkstkefil kctninetek shlimqnsfs nldfdfldiq
 781 nmknlfnsyt ellikeqtsp yelslysfqe qdnnvigdts gkntlveypk diglvyginn
 841 naihltganq nikftndyfe ngltnnfsiy fwlrnlkqnt ikskligske dncgweiyfe
 901 ndglvfniid sngnekniyl snisnnswhy ivisinrlkd qllifidnil vanedikeil
 961 niyssdiisl lsdnnnvyie glsvlnktin sneiltdyfs dlnnsyirnf deeilqysrt
1021 yelfnyvfpe iainkiegnn niylsinnen nlnfkplkfx lintnpnkqy vqkwdevifs
1081 vldgtekyld isttnnriql vdaknnnaqif iinndifisn cltltynnvn vylsiknqdy
1141 nwvicdlnhd ipkksylwil kni
```

FIG. 5I

Neutral-alkaline pH

BoNT          NTNHA pH 6

NTNHA:BoNT complex

FIG. 6A

GSH:GST-NTNHA     BoNT (E.coli lysate)

1 hr incubation
4°C

Binding Buffer
(50 mM MES, 150 mM NaCl, pH 6)

GST-NTNHA:BoNT complex

Wash I: remove contaminants
(binding buffer)

+ protease (activation)

GST-NTNHA:BoNT complex endoproteinase

Activation of bound BoNT
2-4 hr, RT

Wash II: remove protease
(binding buffer)

Elution
(50 mM Tris, 150 mM NaCl, pH 8)

Purified, Activated BoNT

Regenerated GSH:GST-NTNHA

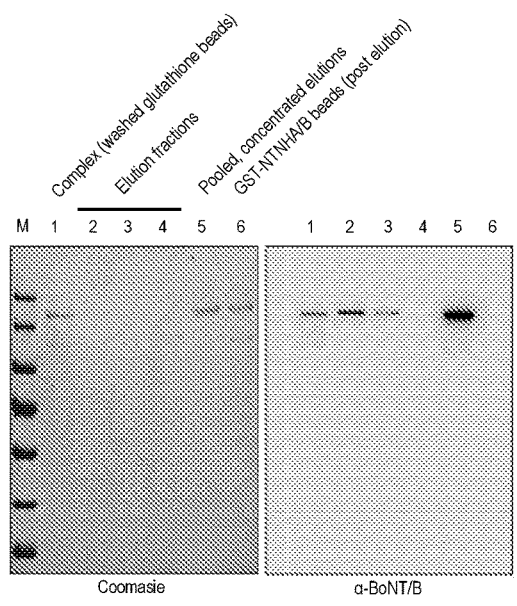
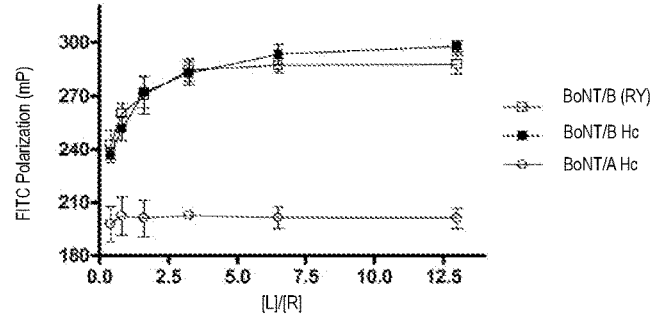
FIG. 7A
FIG. 7B

FIG. 9

METHOD FOR PURIFICATION AND ACTIVATION OF BOTULINUM NEUROTOXIN

CROSS REFERENCE TO RELATED APPLICATIONS

This application is the National Stage of International Application No. PCT/US2017/032985, filed on May 16, 2017, which claims the benefit of U.S. Provisional Application No. 62/336,958, filed on May 16, 2016, the content of which is hereby incorporated by reference herein in its entirety.

SEQUENCE LISTING

The present specification makes reference to a Sequence Listing (submitted electronically as a .txt file named "0342941-0584_SL.TXT" on Nov. 15, 2018). The .txt file was generated on May 16, 2017, and is 96,153 bytes in size. The entire contents of the Sequence Listing are hereby incorporated by reference.

FIELD OF THE INVENTION

The present invention relates to the field of therapeutic use of neurotoxins.

BACKGROUND OF THE INVENTION

Botulinum neurotoxins (BoNTs) are the most toxic substances known to humans. Seven serotypes of BoNTs (A-G) have been identified; with many subtypes within each serotype. BoNTs are ~150 kDa proteins produced by different strains of the bacterium *Clostridium botulinum* (Montal 2010). These toxins cause botulism in animals, a severe neurological disease manifested in extreme flaccid paralysis and possible death. The molecular basis of this toxicity lies in the ability of the BoNTs to bind and enter motor neurons and release their enzymatic domain into the cytosol, which cleaves cellular machinery responsible for synaptic vesicle fusion at neuromuscular junctions (NMJs) and inhibits neurotransmission by blocking acetylcholine release.

The neuro-inhibitory function of BoNTs was explored as a treatment strategy for many muscular disorders ranging from strabismus to managing multiple dystonias (Masuyer et al. 2014), not to mention the steep increase in cosmetic uses of BoNTs (A) to induce flaccid paralysis in facial muscles to smooth wrinkles. The market for BoNTs is approaching 2 billion dollars and still grows at a fast pace.

Several challenges in BoNTs productions exist currently. BoNTs need to be produced in bacteria and isolated from bacterial lysates. The current therapeutic BoNTs are still produced and isolated utilizing old methodologies similar to those originating over 50 years ago when the first batch of lab-prepared BoNT/A was described (Bonventre & Kempe 1959; Pickett 2014). These methods typically involve lengthy incubation/fermentation of the natural bacterial strains that produce these toxins (spore-forming clostridium strains) and many subsequent labor-intensive chromatography steps. Aside from the engineering and containment challenges, these processes may also compromise the final yield, efficacy, and reproducibility of BoNT preparations.

Expressing BoNTs recombinantly from common host systems used for protein production in industry, such as *E. coli* and insect cells has been explored in recent years. An affinity tag, such as His-6 (SEQ ID NO: 1) or GST, is usually fused to BoNTs to facilitate purification via affinity purification. Although isolation of recombinant BoNT with affinity tags simplifies the purification steps, it introduces new problems. The tag may adversely affect biological activity of the toxin and/or have undesired antigenicity. As a result, the tag must be removed after purification, which involves additional enzymatic treatment and purification steps. Furthermore, there are often additional residues left attached to the toxin from the cleaved tag, creating a non-native N- or C-termini which may affect activity or promote immunological consequences in a patient.

Isolation of natural forms of BoNTs is greatly preferred but remains a labor- and time-intensive process.

Purified BoNTs must further be activated through limited proteolysis prior to use. RecombinantBoNTs are usually activated post-purification by incubation with an endoproteinase, such as trypsin. Such activation can cause non-specific degradation, and requires an additional purification step to remove the activation endoproteinase, both of which compromise toxin activity and yield.

SUMMARY OF THE INVENTION

As will be apparent to those skilled in the art reading the present disclosure, the present invention encompasses the recognition of a problem with compositions and methods for production, purification, and/or activation of botulinum neurotoxins (BoNTs) or portions or fragments thereof. Among other things, the present invention identifies challenges in providing materials and procedures that facilitate production, purification, and/or activation of BoNTs with desired characteristics (e.g., relatively uncompromised biological activity; limited introduction of undesired antigenicity; limited contaminants such as undesired endoproteinases and/or degradation products; and high quality, potency, and/or reproducibility of the desired BoNT), while reducing limitations of prior approaches (e.g., limited efficiency of production, time-consuming and/or laborious steps, and/or harsh conditions).

One aspect of the invention relates to a molecule comprising a non-toxic non-hemagglutinin (NTNHA) polypeptide covalently linked to a heterologous affinity moiety. In one embodiment, the NTNHA and affinity moiety are expressed as a fusion protein. In one embodiment of the compositions disclosed herein, the affinity moiety is located at a position selected from the group consisting of the N-terminus of NTNHA amino acid sequence, the C-terminus of NTNHA amino acid sequence, and internal to the NTNHA amino acid sequence. In one embodiment of the compositions disclosed herein, the affinity moiety effectively binds a binding target under conditions of about pH 6 to about pH 8. In one embodiment of the compositions disclosed herein, the affinity moiety is selected from the group consisting of glutathione-S-transferase (GST), C-myc tag, Chitin-binding domain, Streptavidin binding protein (SBP), Cellulose-binding domain, Calmodulin-binding peptide, S-tag, Strep-tag II, FLA, Protein A, Protein G, histidine affinity tag (HAT), Poly-His, and maltose binding protein (MBP). In one embodiment of the compositions disclosed herein, the NTNHA is from serotype A, B, C1, D, E, F, or G. In one embodiment of the compositions disclosed herein, the NTNHA is from serotype B. In one embodiment of the compositions disclosed herein, the molecule is in a complex with a compatible Botulinum neurotoxin (BoNT) or a polypeptide comprising a receptor binding domain thereof. In one embodiment of the compositions disclosed herein, the BoNT or the polypeptide comprises a modified receptor binding domain of *Clostridial botulinum* serotype B (B-H$_c$). In one embodiment of the compositions disclosed herein, the molecule is further bound to a binding target through the affinity moiety. In one embodiment of the compositions disclosed herein, the binding target is stably attached to a matrix.

Another aspect of the invention relates to an aqueous solution comprising one of the molecules described herein.

Another aspect of the invention relates to a nucleic acid that encodes one of the functional NTNHA and affinity moiety fusion protein described herein.

Another aspect of the invention relates to an expression vector comprising the nucleic acid that encodes one of the functional NTNHA and affinity moiety fusion protein described herein.

Another aspect of the invention relates to a host cell that comprises and expresses the nucleic acid that encodes one of the functional NTNHA and affinity moiety fusion protein described herein. In one embodiment, the host cell further expresses a compatible Botulinum neurotoxin (BoNT). In one embodiment of the host cells described herein, the BoNT comprises a modified receptor binding domain of *Clostridial botulinum* serotype B (B-H$_c$). In one embodiment of the host cells described herein, the host cell is prokaryotic or eukaryotic.

In one embodiment of the host cells described herein, the host cell is a bacterial cell, a yeast cell, a mammalian cell, an insect cell, a plant cell, or an amphibian cell.

Another aspect of the invention relates to a method of purifying Botulinum neurotoxin (BoNT) comprising contacting the BoNT to a compatible non-toxic non-hemagglutinin (NTNHA), under conditions appropriate for binding of the NTNHA to the BoNT to thereby form a NTNHA-BoNT complex. In one embodiment, the BoNT is in solution, and the NTNHA is attached to a matrix, whereby the solution is contacted to the matrix to thereby contact the BoNT to the NTNHA. In one embodiment of the methods described herein, the method further comprises washing the matrix to thereby remove unbound materials, and eluting the BoNT from the matrix by contacting the matrix with an aqueous solution that dissociates the BoNT from the NTNHA-BoNT complex. In one alternate embodiment of the methods described herein, following contacting of the BoNT solution to the NTNHA matrix, the method further comprises washing the matrix to thereby remove unbound materials, contacting the matrix with a protease under conditions that preserve the NTNHA-BoNT complex and are appropriate for cleavage of the BoNT within the NTNHA-BoNT complex, washing the matrix to thereby remove the protease and unbound materials, and eluting the BoNT from the matrix by contacting the matrix with an aqueous solution that dissociates the BoNT from the NTNHA-BoNT complex. In one embodiment of the methods described herein, the NTNHA is covalently linked to an affinity moiety, the matrix is linked to a binding target of the affinity moiety, and the NTNHA is non-covalently bound to the matrix through interactions of the affinity moiety and the binding target. In one embodiment of the methods described herein, the NTNHA is covalently linked to the matrix. In one embodiment of the methods described herein, the BoNT comprises a modified receptor binding domain of *Clostridial botulinum* serotype B (B-H$_c$). In one embodiment of the methods described herein, the aqueous solution that dissociates the BoNT from the NTNHA-BoNT complex has a pH of ≤7.5. In one embodiment of the methods described herein, the solution comprising the BoNT is a cleared cell extract from BoNT expressing cells. In one embodiment of the methods described herein, the cleared cell extract further comprises 1 mM of phenylmethylsulfonyl fluoride (PMSF). In one embodiment of the methods described herein, conditions appropriate for binding comprise contacting the BoNT in the context of a binding buffer which has a physiological ionic strength and a pH of <7.5. In one embodiment of the methods described herein, washing is with a wash buffer that is of physiological ionic strength with a pH of <7.5. In one embodiment of the methods described herein, the binding buffer and/or wash buffer is between 100-200 mM KCl or NaCl. In one embodiment of the methods described herein, the binding buffer and/or wash buffer has a pH of about 6. In one embodiment of the methods described herein, the binding buffer and/or wash buffer comprises 50 mM MES, 150 mM NaCl, pH 6. In one embodiment of the methods described herein, the aqueous solution that dissociates the BoNT from the NTNHA-BoNT complex is an elution buffer of about 50 mM Tris, 150 mM NaCl. In one embodiment of the methods described herein, the aqueous solution is an elution buffer of about pH 8. In one embodiment of the methods described herein, the affinity moiety is selected from the group consisting of glutathione-S-transferase (GST), C-myc tag, Chitin-binding domain, Streptavidin binding protein (SBP), Cellulose-binding domain, Calmodulin-binding peptide, S-tag, Strep-tag II, FLA, Protein A, Protein G, histidine affinity tag (HAT), Poly-His, and maltose binding protein (MBP).

In one embodiment of the methods described herein, the affinity moiety is GST, and the binding target is glutathione.

In one embodiment of the methods described herein, the NTNHA is present at a molar ratio between about 1:1 and about 10:1 to the BoNT, for example about 2:1, 3:1, 4:1 or 5:1 to the BoNT. In one embodiment of the methods described herein the BoNT and the NTNHA are co-expressed in the same host cell, for example *E. coli*. In one embodiment of the methods described herein the BoNT and the NTNHA are expressed in different host cells. In one embodiment of the methods described herein the BoNT is produced in a recombinant manner in a heterologous host cell such a *E. coli*. In one embodiment of the methods described herein the BoNT is produced in its native Clostridial cell. In one embodiment of the methods described herein the NTNHA is produced in a recombinant manner in a heterologous host cell such as *E. coli*. In one embodiment of the methods described herein the NTNHA is produced in its native Clostridial cell.

In one embodiment of the methods described herein, the protease is selected from trypsin, pepsin, Lys-C endoproteinase, Lys-N endoproteinase, arginyl endopeptidase, plasmin, omptin and a clostridial protease as described in EP2524963. In a preferred embodiment, the protease is trypsin or Lys-C endoproteinase. In one embodiment, the protease is a protease that cleaves a BoNT non-native (i.e. exogenous) cleavage site. In such clostridial toxins, the native protease cleavage site (also known as the activation site) is modified or replaced with a protease cleavage site that is not native to that clostridial toxin. Non-native proteases that may be employed include Enterokinase (DDDDK↓ (SEQ ID NO: 2)), Factor Xa (IEGR↓(SEQ ID NO: 3)/IDGR↓(SEQ ID NO: 4)), TEV (Tobacco Etch virus) (ENLYFQ↓G (SEQ ID NO: 5)), Thrombin (LVPR↓GS (SEQ ID NO: 6)) and PreScission (LEVLFQ↓GP (SEQ ID NO: 7)).

In one embodiment of the methods described herein, the protease is added at a molar ratio of from about 1:2 to about 1:1000 to the NTNHA, preferably from about 1:5 to about 1:100 to the NTNHA, for example about 1:10, 1:20, 1:30, 1:40 or 1:50. In one embodiment of the methods described herein, the protease is added at a molar ratio from about 1:2 to about 1:1000 to the BoNT, preferably from about 1:5 to about 1:100 to the BoNT, for example about 1:10, 1:20, 1:30, 1:40 or 1:50. Appropriate conditions for the specific protease used will be determined by the skilled practitioner. The length of time for exposure to the protease will also vary with the protease, the concentration used, and the temperature. In one embodiment of the methods described herein, the protease is contacted to the matrix at a temperature from about 2° C. to about 40° C., preferably from about 4° C. to about 37° C., for example 4° C., 16° C., 20° C. or 37° C. In one embodiment of the methods described herein, the protease is contacted to the matrix at room temperature (about 20-22° C.). In one embodiment of the methods described herein, the protease is contacted to the matrix from about 10 minutes to about 18 hours, preferably from about 30 minutes to about 5 hours for example about 30 minutes, 1 hour, 2 hours, 3 hours, 4 hours or 5 hours. In one embodiment of the methods described herein, the protease is contacted to the matrix at a pH of about 5.5 to about 8.5, preferably from about 6 to 8, for example at a pH of about 6, 7 or 8. In one embodiment, the protease is selected from the proteases: trypsin and Lys-C endoproteinase, and is contacted to the matrix at room temperature for about 30 minutes to 2 hours at a pH between 6 and 7.

In one embodiment of the methods described herein, the protease is added at a molar ratio of about 1:10 to the NTNHA. In one embodiment of the methods described herein, the protease is contacted to the matrix at room temperature. In one embodiment of the methods described herein, the protease is contacted to the matrix for about 30 minutes to 12 hours.

Another aspect of the invention relates to a method of purifying Botulinum neurotoxin (BoNT) comprising contacting a cleared cell extract comprising the BoNT to a glutathione coated matrix which has attached thereto a compatible non-toxic non-hemagglutinin (NTNHA) fused to glutathione-S-transferase, in a binding buffer with a pH of about 6 to thereby form a NTNHA-BoNT complex, washing the matrix with a wash buffer with a pH of about 6 to thereby remove unbound materials, contacting the matrix with a protease in a buffer with a pH of about 6 to thereby cleave the BoNT within the NTNHA-BoNT complex, washing the matrix with a wash buffer with a pH of about 6 to thereby remove the protease and unbound materials, and eluting the BoNT from the matrix by contacting the matrix with an elution buffer that has a pH of ≥7.5 to thereby dissociate the BoNT from the NTNHA-BoNT complex. In one embodiment of the methods described herein, the BoNT comprises a modified receptor binding domain of *Clostridial botulinum* serotype B (B-$H_c$). In one embodiment of the methods described herein, the binding buffer and/or wash buffer comprises 50 mM MES, 150 mM NaCl. In one embodiment of the methods described herein, the binding buffer further comprises 1 mM phenylmethylsulfonyl fluoride (PMSF). In one embodiment of the methods described herein, the elution buffer comprises 50 mM Tris, 150 mM NaCl, and has a pH of about 8. In one embodiment of the methods described herein, the glutathione coated matrix is glutathione-linked agarose beads. In one embodiment of the methods described herein, the glutathione coated matrix is a column. In one embodiment of the methods described herein, the glutathione coated matrix has about 5 mg/ml bound NTNHA. In one embodiment of the methods described herein, the protease is trypsin or Lys-C endoproteinase.

Another aspect of the invention relates to a method of purifying a polypeptide comprising a receptor binding domain (Hc polypeptide) of Botulinum neurotoxin, comprising the steps contacting a solution comprising the Hc polypeptide to a matrix which has attached thereto compatible non-toxic non-hemagglutinin (NTNHA), under conditions appropriate for binding of the NTNHA to the Hc-polypeptide to thereby form a NTNHA-Hc polypeptide complex, washing the matrix to thereby remove unbound materials, and eluting the Hc polypeptide from the matrix by contacting the matrix with an aqueous solution that dissociates the Hc polypeptide from the NTNHA-Hc polypeptide complex. In one embodiment of the methods described herein, the receptor binding domain of the Hc polypeptide is a modified receptor binding domain of *Clostridial botulinum* serotype B (B-$H_c$). In one embodiment of the methods described herein, the Hc polypeptide is a Botulinum neurotoxin (BoNT) polypeptide. In one embodiment of the methods described herein, the Hc polypeptide is a chimeric Botulinum neurotoxin (BoNT) polypeptide.

Another aspect of the invention relates to the use of a molecule described herein in a method or purifying a Botulinum neurotoxin (BoNT) polypeptide.

BRIEF DESCRIPTION OF THE DRAWINGS

This patent or application file contains at least one drawing executed in color. Copies of this patent or patent application publication with color drawing (s) will be provided by the Office upon request and payment of the necessary fee.

FIG. 1A) Schematic illustration of pH-dependent bi-molecular complexation of BoNTs and NTNHA. LC: light chain, HN: translocation domain, HCN, HCC: N-terminal and C-terminal segments of the receptor binding domain, respectively. NTNHA has the same domain contents as BoNTs, it is shown as a GST (Glutathione-S-transferase) fused protein immobilized on Glutathione-Agarose resin. FIG. 1B) A flow chart describing a comprehensive purification, activation, and elution protocol of BoNTs using their natural binding partner NTNHA.

FIG. 2A and FIG. 2B are images of gel fractionated proteins. The experimental results indicate the successful purification of BoNT/B using NTNHA/B as a model complex for BoNTs. FIG. 2A) A monoclonal antibody against BoNT/B is used to monitor the presence of BoNT/B along each purification step described in FIG. 1B (except that samples here were not treated with trypsin). FIG. 2B) An SDS-PAGE gel of selected samples stained with Coomassie shows the purity of BoNT/B purified as described in panel A. A major band (~150 kDa) corresponding to BoNT/B is observed in Elution fraction.

FIG. 3A and FIG. 3B are images of two sets of gel fractionated proteins. The experimental results indicate that BoNT/B is efficiently activated in NTNHAB•BoNTB complexes. FIG. 3A) Representative immunoblot of NTNHA-bound BoNT/B activation by trypsin, which separates BoNT/B into two fragments (100 kDa and 50 kDa, respectively). The two fragments of BoNT/B remain attached with each other by a single disulfide bond. They separate from each other when DTT is added to reduce disulfide bond. FIG. 3B) Coomassie stained Elution fraction shows the toxin bands corresponding to the cleaved toxin fragments (at 100 and 50 kDa, respectively). The 150 kDa band is the portion of full-length toxin that remains to be cleaved.

FIG. 4 is an image of gel fractionated proteins. The experimental results establish successful purification of chimeric BoNT/A1B toxin using NTNHA/B. A polyclonal antibody against BoNT/A was used to track the purification steps of a chimeric toxin BoNT/A1B, which is made of BoNT/A1 light chain and translocation domain, with the receptor binding domain from BoNT/B. Full-length BoNT/A1B (the 150 kDa band in the Elution fraction) was successfully purified and eluted using NTNHA/B. We note that the prominent band at 100 kDa is a degradation product of this chimeric toxin, likely cut by endogenous proteases in E. Coli.

Figure 5G:
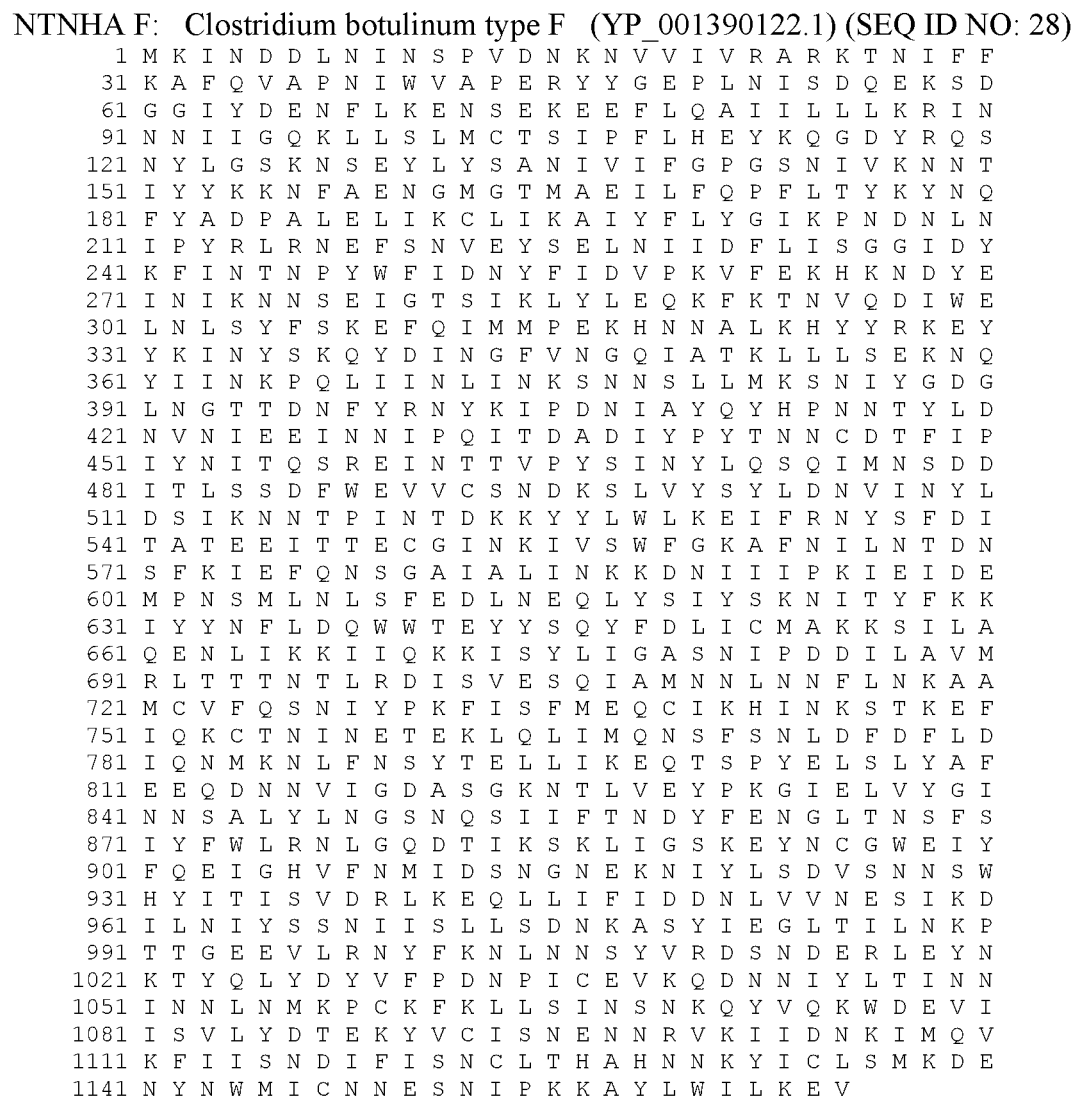

FIGS. 5A-5I (SEQ ID NO.s 22-30) is a list of the amino acid sequences of various serotypes of NTNHA, and variants thereof.

FIGS. 6A-6C is an illustration of an embodiment of a purification principle and protocol for BoNTs, as described herein. FIG. 6A) Schematic illustration of a pH-dependent bi-molecular complexation of BoNTs and NTNHA. LC: light chain, $H_N$: translocation domain, $H_{CN}$, $H_{CC}$: N-terminal and C-terminal segments of the receptor binding domain, respectively. NTNHA has the same domain contents as BoNTs and is shown as a GST (Glutathione-s-transferase) fused protein that may be immobilized on Glutathione-Agarose resin. Interaction between BoNT and NTNHA under slightly acidic conditions (for example, ~pH 6), can be disrupted by manipulating the buffer conditions toward a neutral-alkaline pH. FIG. 6B) BoNT isolation and activation protocol. A flow diagram describing a strategy for purification, activation, and elution of tagged and untagged BoNTs from crude lysates using NTNHA. FIG. 6C) SDS-PAGE analysis of a typical isolation of an inactive BoNT (BoNT/$B_{(RY)}$) from clarified E. coli lysate using GST-NTNHA/B immobilized on Glutathione agarose beads. Binding and wash steps were performed at pH 6 and eluting by exchanging the buffer to pH 8.

FIG. 7A and FIG. 7B show isolated BoNT/B using immobilized NTNHA is pure and binds its canonical neuronal receptor. FIG. 7A) SDS-PAGE analysis (left) shows three elution fractions that are pooled and concentrated (lane 5). A monoclonal antibody against BoNT/B to detect the toxin in all steps (WB, right). The eluted fractions contain non-activated BoNT/B as the major band at ~150 kDa corresponding to a single-chain BoNT/$B_{(RY)}$ toxin. FIG. 7B) Anisotropy-detected binding: the eluted full-length toxin shows similar affinity to a FITC-tagged fragment of its canonical synaptic vesicle receptor Synaptotagmin 1 (Syt 1) as its recombinant $H_C$ domain; BoNT/A $H_C$ does not bind Syt. Error bars represent mean+SEM of 3 samples.

FIG. 8A) Trypsin-mediated activation (cleavage) of BoNT/$B_{(RY)}$ is visualized on an 8% SDS-PAGE. Time-course cleavage of the single chain (SC) toxin results in two fragments: Heavy chain (HC) and Light Chain (LC) linked by a single disulfide bond. FIG. 8B) WB analysis shows that activation of BoNT/B while complexed with NTNHA/B protects it from non-specific trypsinization while allowing for efficient washing and removal of endoproteinase. FIG. 8C) Lys-C endoproteinase can also be used as a specific activator to produce active, dichain toxins using this method.

FIG. 9 shows isolation of chimeric BoNT/A1B1 toxin using NTNHA/B. A polyclonal antibody against BoNT/A is used to track the purification of a chimeric toxin made of BoNT/A (LC$_{(RY)}$, $H_N$) fused to BoNT/B $H_C$ domain. Eluted fractions contain non-activated BoNT/A1B1 protein at ~150 kDa. The prominent band at ~70 kDa is likely a fragment of NTNHA/B that is recognized by the polyclonal antibody.

DETAILED DESCRIPTION OF CERTAIN EMBODIMENTS THE INVENTION

Figure 1A:
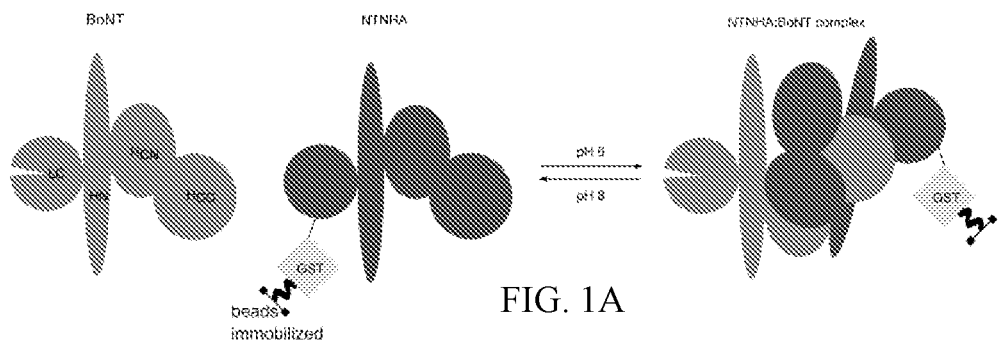
FIG. 1A and FIG. 1B is an illustration of an embodiment of a purification principle and protocol for BoNTs as described herein.

Botulinum neurotoxins (BoNTs) are highly potent protein toxins produced by spore-bearing *Clostridium botulinum*. In the last few decades, these deadly agents have been found useful in treating numerous neuromuscular disorders and in aesthetic applications by blocking neurotransmitter release in the injected muscles. Now established therapeutic agents, BoNTs are widely produced in large scales by several manufacturers around the world. Available data suggest manufacturing procedures rely on decades-old methodologies that utilize sporulating strains, and toxin isolation is achieved by many laborious and inefficient bulk purification steps. An improved method for the direct purification and activation of therapeutic BoNTs is needed.

Botulinum neurotoxins (BoNTs) are the most toxic substances known to man. Seven serotypes of BoNTs (A-G) proteins have been identified as ~150 kDa products of different strains of the bacterium *Clostridium botulinum* (Montal 2010). These toxins cause botulism in animals, a severe neuromuscular disease manifested in extreme flaccid paralysis. The molecular basis of this toxicity lies the toxins' ability to potently bind receptors on motor neurons at the neuromuscular junction (NMJ), internalize by endocytosis, and traverse the endosomal membrane to release their enzymatic chain into the cytosol. The released protease then cleaves the cellular machinery (SNARE proteins) responsible for synaptic vesicle fusion at the NMJ, thus inhibiting neurotransmission by blocking acetylcholine release (Blasi et al. 1993; Borden Lacy et al. 1998; Rossetto et al. 2014).

Botulinum neurotoxins (BoNTs) can also be used as tools to locally control muscle activities, especially uncontrolled activities or abnormalities due to muscular spasticity (Masuyer et al. 2014). This neuro-inhibitory function of BoNTs was explored as a treatment strategy for many muscular disorders, including strabismus and managing multiple dystonias and lower urinary tract dysfunctions (LUTD) (Jankovic & Brin 1991; Truong & Jost 2006; Visco et al. 2012; Jiang et al. 2015). As a therapeutic and/or cosmetic agent, BoNTs can be used to paralyze facial muscles for the purpose of smoothing wrinkles (Hexsel et al. 2011). Additional applications of the toxins aim to alleviate depression and prophylactic treatment of migraines (Finzi & Rosenthal 2014; Jackson et al. 2012). The clinical uses of the toxin have garnered much public interest (Sifferlin 2017).

Botulinum neurotoxins (BoNTs) can be isolated from a growth of spore-forming clostridium strain and subsequently purified to a final product (Pickett 2014). The available data on BoNTs production processes and isolation suggests that producers utilize methodologies of culture and growth conditions in native strains similar to those originating decades ago (Pickett & Perrow 2009; Snipe & Sommer 1928; Duff, Wright, et al. 1957; Duff, Klerer, et al. 1957; Bonventre & Kempe 1959; Schantz & Johnson 1992; Pickett 2014). Such methods are limited by the efficiency in which the native clostridium strain can produce the toxin and typically involve lengthy fermentation periods of the natural source of the toxin (spore-producing clostridium strains) followed by laborious toxin-isolation procedures often under harsh conditions involving several acid/alcohol precipitations, crystallizations and/or multiple chromatographic steps (DasGupta & Boroff 1967; Tse et al. 1982; Schantz & Johnson 1992; Malizio et al. 2000).

Producing tagged BoNTs recombinantly is feasible with the inclusion of an affinity tag (e.g. $His_{6X}$ or GST-fusion) to aid in toxin purification using affinity chromatographies. Such approaches, however, have disadvantages, for example in use of BoNTs as therapeutic biologics. For instance, the affinity tags may adversely affect biological activity of the toxin and/or have undesired antigenicity. Removal of a tag after purification also requires additional enzymatic and purification steps while producing non-native N- or C-termini in the final product. Further, recombinant BoNTs need to be activated post-purification by an endoproteinase to obtain functional and potent dichain toxins. This proteolytic step leads to non-specific degradations which necessitates additional purification steps to remove endoproteinases and or degradation products. Aside from engineering and containment challenges for toxin production from spore-forming strains and subsequent purifications (Malizio et al. 2000; Pickett 2014), these recombinant approaches can compromise most properties in the final product, ranging from quality and potency to efficient reproducibility. A new strategy to safely and efficiently isolate active therapeutic BoNTs would be beneficial for large-scale production and facile isolation of BoNTs.

Studies on the biochemical properties and cellular mechanisms by which clostridial neurotoxins gain entry to the neuronal cytosol have provided some understanding of the structural, molecular, and mechanistic functions of clostridial neurotoxins (Blasi et al. 1993; Borden Lacy et al. 1998; Dong et al. 2006; Rossetto et al. 2014). Foodborne botulisms require passage of intact toxins and other products of the bacterium through a host's gastrointestinal tract. The molecular and structural basis of this ability to avoid degradation remained a mystery until recently, when larger complexes called "progenitor toxin complexes" (PTCs) were characterized to constitute the whole toxic agent encountered by a target organism. In addition to the proteolytically active toxin, these multi-protein complexes are typically comprised of a serotype-specific non-toxic non-hemagglutinin (NTNHA) protein and three hemagglutinin proteins (HAs) (Lee et al. 2014). Previously considered to aid toxin functions (Schantz & Johnson 1992), PTCs are now known to physically shield and protect BoNTs from the harsh gastrointestinal environment to safely reach its destinations: first to epithelial barriers and subsequently to NMJs where it can be internalized into the cytosol via synaptic vesicle recycling mechanisms. In a structural study (Gu et al. 2012), Gu and coworkers indicated in atomic details a minimally effective PTC (m-PTC) in a non-covalent complex of BoNT/A:NTNHA/A. The co-crystal structure of the toxin:NTNHA complex indicated a pH-dependent complex formation. BoNT/A and NTNHA/A were reported to be able to form a tight complex with nanomolar-level affinity under slightly acidic conditions (~pH 6). However, such complex formation was said not to occur at neutral-alkaline pH.

Disclosed herein are compositions and methods relating to the purification of BoNT which utilize the natural affinity of the BoNT molecule for the non-toxic non-hemagglutinin (NTNHA) protein. BoNT naturally forms a dimer complex with the NTNHA chaperone protein and is protected from protease and acidic degradation in the gastrointestinal tract. The binding is reversible and is dependent on pH, binding at pH<7, and dissociating at pH>7.4. The NTNHA protein is added to a mixture containing the BoNT at a pH that promotes binding. The BoNT:NTNHA complex is isolated from other components of the mixture by immobilization of the NTNHA within the complex. Following washing, the BoNT is then released from the complex by raising the pH to promote dissociation. Since this method does not rely on an affinity modification of the BoNT, un-tagged forms of the toxin can be purified.

The purification methods described herein also make possible activation of the BoNT while in the BoNT:NTNHA complex. Following activation, the BoNT can be released from the complex thereby generating a purified, activated form of the toxin.

Aspects of the invention relate to a method of purifying a BoNT. Typically the BoNT is in the context of an aqueous solution containing contaminating components, such as a cellular extract. The method comprises combining the solution with the NTNHA molecule under conditions appropriate for binding of the BoNT to the NTNHA. Practically, this can involve combining the NTNHA molecule with the aqueous solution (e.g., cellular extract or a cleared cellular extract). The BoNT can be isolated by virtue of the NTNHA molecule. Generally this is accomplished by immobilization of the NTNHA to a matrix. Unbound materials are removed from the complex, for example, by washing the matrix (e.g, using a wash buffer amount of 3-4 volumes of the matrix). Following washing, the BoNT is released from the complex, for example, by elution from the matrix bound NTNHA, to produce a purified polypeptide.

The BoNT can be activated prior to release from the complex by digestion with a protease. This can be accomplished by contacting the matrix bound complex with a protease under conditions appropriate for cleavage of the BoNT that do not otherwise disrupt the complex (e.g., that preserve the required pH). The protease is eliminated along with other unbound materials, by washing the matrix (e.g., with a wash buffer). The activated, purified BoNT can then be eluted by contacting the matrix with an aqueous solution that dissociates the BoNT from the NTNHA complex (e.g., with an elution buffer). In some embodiments, activation of the polypeptide is not required or desired.

The NTNHA used in the method must be compatible with the BoNT. The term compatible, when used in reference to the NTNHA and the BoNT, refers to the molecules being able to form a tight and stable complex with one another. In one embodiment, the BoNT and the NTNHA are components of the same naturally occurring BoNT serotype protein complex. This occurs when the BoNT and NTNHA coding sequences are from the same operon. As the term "serotype" is used herein to describe the NTNHA molecule, being "from a serotype" refers to an NTNHA molecule derived from an operon which encodes a specific serotype of BoNT. Compatible may also refer to a BoNT or chimeric polypeptide having a region (e.g., the Hc region) that is compatible with the NTNHA. In one embodiment, the NTNHA and the Hc region of the BoNT are both derived from the same naturally occurring BoNT serotype complex.

Immobilization of the NTNHA to the matrix can occur prior to or following binding of the BoNT. In one embodiment, the NTNHA is attached to a matrix and a solution comprising the BoNT is added to the matrix to thereby contact the Hc polypeptide to the NTNHA and promote complex formation. In one embodiment, the NTNHA and BoNT are in a complex prior to attachment of the NTNHA to the matrix.

In one embodiment, an affinity moiety is introduced onto the NTNHA protein (e.g., by expression as a fusion protein), and the tagged protein is used to bind and isolate the BoNT under conditions that promote the BoNT:NTNHA binding. The BoNT:NTNHA complex is isolated by affinity purification of the NTNHA within the complex.

Binding buffers, incubation buffers, wash buffers, and protease digestion buffers, will promote conditions appropriate for formation and preservation of the Hc-NTNHA complex. This includes, without limitation, having a pH that promotes complex formation. Typically this will be a pH of less than 7.5, for example less than 6. In one embodiment, the buffer pH is from 2-8. In one embodiment, the buffer pH is from 5-7. In one embodiment the pH is about 5, about 6, or about 7. The binding buffers, incubation buffers and wash buffers may all be highly similar or the same. The buffers may further contain additional components other than those specified herein. In one embodiment, the buffer further contains a stabilizing agent for the BoNT polypeptide (e.g., serum albumin, polysaccharide, trehalose, or surfactant). The pH of the buffers can be optimized for the various components therein within the specified ranges. The skilled practitioner will appreciate that buffer pH should preserve the overall protein structure, avoiding a pH that approaches the PI of the protein which may precipitate the protein.

The buffers will preferably have physiological ionic strength (e.g., within the range of 100-200 mM KCl or NaCl). A variety of salts are available to create the required ionic strength. Salt concentrations that are too high may disrupt the interactions due to polar/ionic interference. In one embodiment, the salt concentration is 400 mM or less. Conditions of low salt are also expected to work sufficiently. In one embodiment, the salt concentration is 150 mM. In one embodiment, the buffer comprises 50 mM MES, 150 mM NaCl, and has pH 6. In one embodiment, the buffer in which binding occurs (binding buffer) further comprises one or more protease inhibitors (e.g., phenylmethylsulfonyl fluoride (PMSF)). In one embodiment, the binding buffer comprises PMSF at a concentration of from about 0.1 to 1 mM. In one embodiment, the PMFS is about 1 mM.

Washing can be performed, for example, using a wash buffer. A typical amount for washing is 3-4 volumes of the matrix.

The BoNT molecule contains several domains and binds to the NTNHA molecule through its receptor binding domain (otherwise referred to as the Hc domain). As such, the herein described methods are applicable to the purification of any polypeptide comprising a receptor binding domain (Hc polypeptide) of Botulinum neurotoxin (e.g, full length BoNT or fragment thereof comprising the Hc polypeptide, or a chimeric polypeptide comprising the Hc domain).

In one embodiment of the methods described herein, the NTNHA is present at a molar ratio between about 1:1 and about 10:1 to the BoNT or the receptor binding domain thereof, for example about 2:1, 3:1, 4:1 or 5:1 to the BoNT or receptor binding domain thereof.

Activation of bound BoNT or a fragment thereof, is achieved by contacting the BoNT:NTNHA complex (e.g., when bound to the matrix) with an appropriate protease. In one embodiment, the protease cleaves a protein after a lysine residue. In one embodiment, the proteases is, without limitation, trypsin, pepsin, Lys-C endoprotease, Lys-N endoproteinase, arginyl endopeptidase, plasmin, omptin, or the clostridial protease as described in EP2524963. Preferred conditions will result in no substantial degradation of the NTNHA, of any associated affinity moieties, or of their binding target. Conditions appropriate for cleavage include the appropriate concentration of protease, and the appropriate conditions for activity of the protease (e.g., temperature, incubation time, buffer components, etc.). Such conditions can be achieved by use of an appropriate protease digestion buffer. The amount of the protease used can be determined by the amount of the NTNHA molecule or by the amount of the BoNT molecule. In one embodiment, the protease is present at a molar ratio of from about 1:2 to about 1:1000 to the NTNHA molecule. In one embodiment, the protease is present at a molar ration of from about 1:5 to about 1:100 to the NTNHA molecule, for example, about 1:10, 1:20, 1:30, 1:40, or 1:50. In one embodiment of the methods described herein, the protease is added at a molar ratio from about 1:2 to about 1:1000 to the BoNT (e.g., from about 1:5 to about 1:100 to the BoNT), or about 1:10, 1:20, 1:30, 1:40 or 1:50.

Appropriate conditions for the specific protease used will be determined by the skilled practitioner. The length of time for exposure to the protease will also vary with the protease, the concentration used, and the temperature. In one embodiment, the protease is contacted at a temperature between 2° C. and 40° C., preferably between 4° C. and 37° C., (e.g., 4° C., 16° C., 20° C., or 37° C.). In one embodiment, the protease is contacted at room temperature (about 20-22° C.).

In one embodiment, the protease is contacted for about 10 minutes to about 18 hours, preferably between 30 minutes and 5 hours (e.g., about 30 minutes, 1 hour, 2, 3, 4 or 5 hours). In one embodiment, the protease is contacted for about 4 hours. In one embodiment the protease is Lys-C endoprotease and the incubation time is about 30 minutes.

In one embodiment, the protease is contacted to the matrix at a pH of about 5.5 to about 8.5. In one embodiment, the protease is contacted to the matrix at a pH of about 6 to about 8, (e.g., about 6, 7 or 8).

In one embodiment, the protease is selected from the proteases trypsin and Lys-C endoproteinase, and is contacted to the matrix at room temperature for about 30 minutes to 2 hours at a pH between 6 and 7.

Elution of the BoNT from the BoNT-NTNHA complex is accomplished using an aqueous solution with a pH that promotes dissociation of the complex (referred to herein as an elution buffer). Preferably, the elution buffer disrupts the BoNT-NTNHA complex by being of the appropriate pH, while otherwise substantially preserving the integrity of the Hc polypeptide and substantially preserving the immobilization of the NTNHA (e.g., preserving binding of the NTNHA to a matrix). The elution buffer will further preferably have physiological ionic strength. A variety of buffers available are appropriate for use (e.g., Tris, MOPS, HEPES, phosphate buffer, etc). In one embodiment, the elution buffer is the same as the binding and/or wash buffer, differing only in pH. In one embodiment, the elution buffer is about 50 mM Tris, 150 mM NaCl with an appropriate pH discussed herein (e.g., pH 8).

The elution buffer used (e.g., those described herein) can be from about pH 7 to about pH 11. In one embodiment, the pH is 7.5 or greater. In one embodiment, the pH is about 8. The elution buffer may further contain additional components other than those specified herein. The pH of the elution buffer can be optimized for the various components therein.

Typically the BoNT is purified from a cellular extract. In one embodiment, the cellular extract is a cleared cellular extract. The term "cleared cellular extract" refers to the extract being substantially free of all particulate matter such as when removed by centrifugation and/or filtration.

The BoNT and the NTNHA may be co-expressed in the same host cell, for example E. coli. The method may utilize the NTNHA expressed therein with the BoNT. Alternatively, the BoNT and the NTNHA can be expressed in different host cells. The respective cell extracts can be used to produce/isolate the respective proteins. The BoNT can be produced in a recombinant manner in a heterologous host cell such a E. coli, or produced in its native Clostridial cell. The NTNHA can be produced in a recombinant manner in a heterologous host cell such a *E. coli*, or in its native Clostridial cell.

"Purification", or "purified", as used herein, refers to a BoNT or fragment thereof that is "substantially pure", with respect to other components of a preparation (e.g., other polypeptides). It can refer to a BoNT or fragment that is at least about 50%, 60%, 70%, or 75%, preferably at least about 85%, more preferably at least about 90%, and most preferably at least about 95% pure, with respect to other components. Recast, the terms "substantially pure" or "essentially purified", with regard to a BoNT or fragment, refers to a preparation that contains fewer than about 20%, more preferably fewer than about 15%, 10%, 8%, 7%, most preferably fewer than about 5%, 4%, 3%, 2%, 1%, or less than 1%, of one or more other components (e.g., other polypeptides or cellular components).

Other aspects of the invention relate to the components used in the methods described herein. One aspect of the invention relates to the NTNHA polypeptide used to bind the BoNT. The NTNHA polypeptide can be full length NTNHA, or a functional fragment thereof. A functional fragment of NTNHA is considered to retain the binding property to the compatible BoNT Hc domain, and protect the BoNT from degradation, while allowing activation. The NTNHA polypeptide may further comprise additional heterologous amino acids. As the term is used herein, heterologous refers to a molecule of a different origin. For example, a heterologous affinity moiety differs from any internal affinity moieties naturally present in the NTNHA molecule.

Heterologous sequences may be covalently linked to the NTNHA (e.g., by expression as a fusion protein or by post-translational modification of the NTNHA molecule). In one embodiment, the additional heterologous amino acid sequences is a heterologous affinity moiety.

Heterologous amino acid sequences can be present on the N-terminus, C-terminus, or internally. Such sequences when present should be designed to preserve the interaction of the NTNHA with the BoNT Hc domain. In one embodiment, the heterologous sequence is an affinity moiety and there is no intervening sequence between the affinity moiety and the NTNHA sequence. In one embodiment, the heterologous amino acids are located at the N-terminus of the NTNHA.

In one embodiment, the heterologous amino acids lack a functional protein cleavage site such as those that typically are used to remove an affinity tag from a fusion protein. In one embodiment, the invention excludes an NTNHA polypeptide comprising a myc-tag fused to the N-terminus, e.g., NTNHA-A1 (Gu et al., Science 335: 977-981 (2012)).

In one aspect of the invention, the NTNHA polypeptide is stably attached to a matrix. Stable attachment refers to attachment that is not disrupted by the conditions of the various buffers described herein. Attachment to the matrix can be via covalent or non-covalent interactions. In one embodiment, attachment to the matrix is through the interaction of a heterologous affinity moiety on the NTNHA polypeptide with a corresponding binding moiety on the matrix (e.g., a GST affinity moiety on the NTNHA with glutathione present on the matrix).

In one embodiment the NTNHA polypeptide in the various forms described herein (e.g., linked to an affinity moiety and/or stably attached to a matrix) is further in a complex with a compatible BoNT or a polypeptide comprising a receptor binding domain (Hc) thereof. In one embodiment, the BoNT or Hc is a native protein. In one embodiment, the BoNT or Hc is a genetically modified receptor binding domain (e.g., with increased binding for a specific receptor).

In one embodiment, the NTNHA polypeptide comprising the affinity moiety is further bound to a binding target through binding of the affinity moiety. The binding target may further be stably attached to a matrix.

Another aspect of the invention relates to an aqueous solution which contains the NTNHA polypeptide described herein. The NTNHA polypeptide within the solution can be of any form described herein, such as linked to an affinity moiety, stably attached to a matrix, and/or bound to a binding target through an affinity moiety, any of which may be further bound to a compatible BoNT.

Nucleic acid sequences that encode the NTNHA and affinity moiety fusion protein described herein are also encompassed by the invention. The nucleic acid sequences encoding the proteins can be optimized for *E. coli* expression. In one embodiment, the nucleic acid sequences are in the context of a vector (e.g. an expression vector). Vectors should be compatible with the host cells in which the nucleic acids are intended to be propagated and/or expressed.

NTNHA

NTNHA is a 140 kDa protein synthesized by *Clostridium botulinum*. NTNHA genes occur within operons that encode a particular serotype BoNT protein. BoNT and the NTNHA produced from the same opeon are components of the same naturally occurring BoNT protein complex, and form a tight, stable complex with one another. NTNHA binds the BoNT with a $K_d$ of approximately 30.8 nM, at a 1:1 stoichiometry (Shenyan et al., Science 335: 977-981 (2012)). Preferably the NTNHA is derived from the same *Clostridium botulinum* strain which produces that serotype (and subtype) of BoNT or Hc fragment being purified (A, A1, A2, A3, A4-A, A4-B, types B, C, C1, D, E, F or G). Some overlap of binding between serotypes can be expected. The amino acid sequences of different NTNHA proteins are available to the skilled practitioner, as are the encoding nucleic acid sequences, such as NTNHA proteins derived from operons encoding BoNTserotypes: A1 (YP_001253341.1), A2 (WP_012704905), B (WP_003404192.1), C1 (YP_398515.1), D (BAA75083.1), E (WP_003409842), F (YP_001390122.1), and G (CAA61228.1). In one embodiment, the invention excludes use of the NTNHA/A (NTNHA/A1) molecule and the encoding nucleic acids.

BoNT

Different serotypes of botulinum neurotoxins are known in the art (A-G), and many subtypes also exist (A1, A2, A3, A4-A, A4-B). Methods described herein can be used to purify native BoNT (produced by clostridial bacteria), or a recombinant protein. Recombinant BoNT can be produced in any other type of host such as other prokaryotic cells, eukaryotic cells, tissues or organisms.

Mutated variants of BoNT (e.g., resulting from amino acid substitutions, insertions, or deletions) can also be isolated. In one embodiment, the variant has increased toxicity (e.g., by having increased binding to the cellular receptors). Such mutated variants can comprise a "modified receptor binding domain" or "modified $H_C$". A modified Hc, as the term is used herein, has one or more non-naturally occurring substitution mutations that enhance the binding of the *C. botulinum* neurotoxin molecule in which it is comprised, to a receptor for *C. botulinum* neurotoxin located on the surface of a target cell. Such a molecule is typically generated through genetic recombination technology. The modified $H_C$ has a binding activity for the receptor for *C. botulinum* neurotoxin that is stronger than its wild type counterpart. Examples of modified receptor binding domains are disclosed in U.S. Application 2015/166972, the contents of which are incorporated herein by reference. The invention is further useful for isolating any molecule possessing or retaining the biological activity of the botulinum toxin, such as a fusion (or chimeric) protein, truncated protein, protein fragment, or a mutated variant of botulinum toxin such as a protein having one or more amino acids added, deleted or replaced.

In one embodiment, the BoNT isolated by the methods described herein has toxic activity. The activity of the BoNT can be determined by measuring the proteolytic activity on the appropriate substrate. Botulinum toxin types A and E toxins cleave the protein SNAP-25. Botulinum toxin types B, D, F and G cleave vesicle-associated membrane protein (VAMP, called synaptobrevin). Botulinum toxin type C1 cleaves both SNAP25 and also the protein syntaxin. Assays that can be used to determine this activity are known in the art such as described in WO 95/33850, the contents of which are incorporated by reference herein.

Affinity Moieties

The NTNHA can be attached to an affinity moiety. The affinity moiety specifically binds a binding target under the conditions of the methods described herein (e.g., from about pH 6 to about pH 8). A variety of affinity moieties are known in the art and available for use in the invention. An affinity moiety can be a member of a specific binding pair, such as an epitope that is specifically recognized by an antibody. When an epitope is used as the affinity moiety, the antibody is used as the binding target. Many such affinity moiety: antibody combinations are known in the art and commercially available. Examples include, without limitation, c-myc (Roth et al, (1991) J. Cell Biol. 115:587-596), myc (EQKLISEEDL (SEQ ID NO: 8); Evan G I, et al. (1985) Mol. Cell Biol. 5:3610-3616; Munro S. and Pelham H R B, (1987) Cell 48:899-907; Borjigin J. and Nathans J., (1994) 269:14715-14727; Smith D J, (1997) BioTechniques 23:116-120) FLAG® (U.S. Pat. Nos. 4,703,004; 4,851,341 and 5,011,912), HA, derived from the influenza hemagglutinin protein (Wilson I A, et al., (1984) Cell, 37:767; Field J. et al. Mol. Cell Biol. (1988) 8:2159-2165; Xu Y, et al. (2000) Mol Cell Biol. 20:2138-2146), IRS (RYIRS (SEQ ID NO: 9); Liang T C et al. (1996) 329:208-214; Luo W et. al. (1996) Arch. Biochem. Biophys. 329:215-220), AU1 and AU5 ((DTYRYI (SEQ ID NO: 10) and TDFLYK (SEQ ID NO: 11)); Lim P S et al. (1990) J. Infect. Dis. 162:1263-1269; Goldstein D J et al. (1992) 190:889-893; Koralnik I J et al. (1993) J. Virol. 67:2360-2366), glu-glu (a 9 amino acid epitope from polyoma virus medium T antigen (EE-EEYMPME (SEQ ID NO: 12)); Grussenmeyer, T. et al. (1985) PNAS. USA 82:7952-7954; Rubinfeld. B. et al. (1991) Cell 65:1033-1042), KT3 (an 11 amino acid epitope from the SV40 large T antigen (KPPTPPPEPET (SEQ ID NO: 13)); MacArthur H. and Walter G. (1984) J. Virol. 52:483-491; Martin G A et al. (1990) 63:843-849; Di Paolo G et al. (1997) 272:5175-5182), T7 (an 11 amino acid leader peptide from T7 major capsid protein (MASMTGGQQMG (SEQ ID NO: 14))), S-TAG, HSV (an 11 amino acid peptide from herpes simplex virus glycoprotein D (QPELAPE-DPEDC (SEQ ID NO: 15))), VSV-G (an 11 amino acid epitope from the carboxy terminus of vesicular stomatitis virus glycoprotein, (YTDIEMNRLGK (SEQ ID NO: 16)); Kreis T. (1986) EMBO J. 5:931-941; Turner J R et al (1996) 271:7738-7744), Anti-Xpress (8 amino acid epitope, (DLYDDDK (SEQ ID NO: 17))), and VS (14 amino acid epitope from paramoxyvirus SV5, (GKPIPNPLLGLDST (SEQ ID NO: 18))).

Another epitope commonly used as an affinity moiety is the FLAG®. This sequence typically consists of DYKDDDDK (SEQ ID NO: 19), but any combination of 3 to 6 aspartic or glutamic acid residues is also considered a FLAG® sequence. The FLAG® affinity tag has effectively been used in various expression systems for the purification of recombinant fusion proteins (Brizzard et al. (1994) Bio-Techniques 16:730-735; Lee et al. (1994) Nature 372:739-746; Xu et al. (1993) Development 117:1223-1237; Dent et al. (1995) Mol. Cell Biol. 15:4125-4135; Ritchie et al. (1999) BioChem Journal 338:305-10).

There are also many affinity moieties that are not epitope based, and these can also be used in the invention. GST (Glutathione-S-transferase) is an affinity moiety envisioned for use in the instant invention (U.S. Pat. Nos. 5,654,176; 6,303,128 and 6,013,462). The poly-histidine affinity moiety is a non-natural consecutive sequence of histidine amino acid residues including any corresponding peptides disclosed in U.S. Pat. Nos. 5,284,933 and 5,310,663. Typically such sequences comprise four to ten histidine residues (SEQ ID NO: 20).

In one embodiment, the affinity moiety is glutathione-S-transferase (GST), C-myc tag, Chitin-binding domain, Streptavidin binding protein (SBP), Cellulose-binding domain, Calmodulin-binding peptide, S-tag, Strep-tag II, FLA, Protein A, Protein G, histidine affinity tag (HAT), Poly-His, or maltose binding protein (MBP). In one embodiment, the affinity moiety is not GST, C-myc tag, Chitin-binding domain, SBP, Cellulose-binding domain, Calmodulin-binding peptide, S-tag, Strep-tag II, FLA, Protein A, Protein G, HAT, Poly-His, or MBP. In one embodiment, the affinity moiety is AviTag™, V5, Myc, T7, FLAG, HSV, VSV-G, poly His (typically His$_6$ (SEQ ID NO: 1)), biotin, or STREP (WSHPQFEK (SEQ ID NO: 21)). In one embodiment, the affinity moiety is not AviTag™, V5, Myc, T7, FLAG, HSV, VSV-G, poly His, biotin, or STREP.

Binding pair members that interact with or are found naturally within the mammalian (human) body such as antibodies that naturally bind to NTNHA, or molecules recognized by transporters in the liver and/or kidney, are excluded from the compositions described herein.

Binding Targets for Affinity Moieties

Binding targets are used to immobilize the NTNHA polypeptide through binding of the affinity moiety. The binding target will typically be specific for a given affinity moiety. Binding targets are attached to the matrix such that their binding affinity for the affinity moiety is preserved. For example, the binding target for an epitope tag is an antibody which specifically binds the epitope tag. The binding target for GST is glutathione. The binding target for biotin is avidin or streptavidin. The binding target for STREP is Strep-tactin. The binding target for polyHis is bivalent nickel or cobalt ions. The binding target for protein G is the Fc portion of IgG. The binding target for protein A is the Fc portin of immunoglobulin of various species.

Matrix

Various inert substance typically used to immobilize a molecule through physical attachment can be used as the matrix in the invention. The matrix, otherwise referred to as a substrate, can be made from a wide variety of materials and may take a variety of forms. Materials include, without limitation metal, metal alloy, polymer, plastic, paper, glass, fabric, packaging material, biological material such as cells, tissues, hydrogels, proteins, peptides, nucleic acids, and any combinations thereof. Forms the matrix can take include, without limitation, beads (including polymer microbeads, magnetic microbeads, and the like), filters, fibers, screens, mesh, tubes, hollow fibers, scaffolds, plates, channels, and any combination thereof. Other examples of substrate matrixes known in the art include, but are not limited to, nucleic acid scaffolds, protein scaffolds, lipid scaffolds, dendrimers, microparticles or microbeads, nanotubes, and microtiter plates. In one embodiment, the matrix components are in the form of a column.

In one embodiment, the NTNHA polypeptide is attached to the matrix by the coupling of an affinity moiety present on the NTNHA to a binding target present on the matrix surface. Various affinity moieties and binding targets are available for use, example of which are discussed herein. In one embodiment, the matrix is coated with glutathione as the binding target (e.g., glutathione-linked agarose beads). In one embodiment, the glutathione coated matrix is in the form of a column.

In one embodiment, the NTNHA polypeptide is conjugated directly to a matrix surface through a covalent or non-covalent interaction. This can occur through the N-terminus, the C-terminus, or internally to the molecule. It may further be useful to include a linker on the NTNHA polypeptide in order to facilitate attachment to the substrate.

Conjugation to the substrate can be accomplished using a variety of methods in the art. Examples of covalent attachment include, without limitation silane coupling (Weetall, 15 Adv. Mol. Cell Bio. 161 (2008); Weetall, 44 Meths. Enzymol. 134 (1976)), and use of NHS reaction or a conjugation agent. Non-covalent attachment can be based on ionic interactions, van der Waals interactions, dipole-dipole interactions, hydrogen bonds, electrostatic interactions, and/or shape recognition interactions. Without limitations, conjugation can include either a stable or a labile bond or conjugation agent. Exemplary conjugations include, but are not limited to, covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, cyclodextrin/adamantly host guest interaction) and the like. As used herein, the term "conjugation agent" means an organic moiety that connects two parts of a compound. Linkers typically comprise a direct bond or an atom such as oxygen or sulfur, a unit such as NR1, C(O), C(O)NH, SO, SO2, SO2NH or a chain of atoms, where one or more methylenes can be interrupted or terminated by O, S, S(O), SO2, NH, C(O)N(R1)2, C(O), cleavable linking group, substituted or unsubstituted aryl, substituted or unsubstituted heteroaryl, substituted or unsubstituted heterocyclic; where R1 is hydrogen, acyl, aliphatic or substituted aliphatic.

A variety of conjugation chemistry is available for conjugating two molecules together and can be used for linking the NTNHA polypeptide to a matrix. Exemplary coupling molecules and/or functional groups for conjugating at least one engineered microbe-targeting molecule to a substrate include, but are not limited to, a polyethylene glycol (PEG, NH2-PEGX-COOH which can have a PEG spacer arm of various lengths X, where 1<X<100, e.g., PEG-2K, PEG-5K, PEG-10K, PEG-12K, PEG-15K, PEG-20K, PEG-40K, and the like), maleimide conjugation agent, PASylation, HESylation, Bis(sulfosuccinimidyl) suberate conjugation agent, DNA conjugation agent, peptide conjugation agent, silane conjugation agent, polysaccharide conjugation agent, hydrolyzable conjugation agent, and any combinations thereof.

The amount of NTNHA bound to the matrix can be determined and optimized by the skilled practitioner. In one embodiment, the matrix has about 20 mg/ml of NTNHA polypeptide. In one embodiment, the matrix has about 5 mg/ml polypeptide, or about 2 mg/ml polypeptide.

Proteases

Any protease that will cleave the BoNT can be used in the herein described methods. Such proteases include, without limitation trypsin, pepsin, Lys-C endoproteinase, Lys-N endoproteinase, arginyl endopeptidase, plasmin, omptin and a clostridial protease as described in EP2524963. In one embodiment, the protease is trypsin or Lys-C endoproteinase. In one embodiment, the protease is a protease that cleaves a BoNT non-native (i.e. exogenous) cleavage site. In such clostridial toxins, the native protease cleavage site (also known as the activation site) is modified or replaced with a protease cleavage site that is not native to that clostridial toxin. Non-native proteases that may be employed include Enterokinase (DDDDK↓(SEQ ID NO: 2)), Factor Xa (IEGR↓(SEQ ID NO: 3)/IDGR↓(SEQ ID NO: 4)), TEV (Tobacco Etch virus) (ENLYFQ↓G (SEQ ID NO: 5)), Thrombin (LVPR↓GS (SEQ ID NO: 6)) and PreScission (LEVLFQ↓GP (SEQ ID NO: 7)), (the denotes the cleavage site).

Nucleic Acid Vectors

Another aspect of the invention relates to a nucleic acid vector comprising the nucleic acid molecule encoding the NTNHA polypeptide described herein. The vector can be a vector solely for propagation of a nucleic acid sequence in an organism or cell or can also be for expression of the nucleic acid sequence as a polypeptide in that organism or cell.

In one embodiment the vector is an expression vector. Such an expression vector is referred to herein as an expression construct, and comprises a nucleic acid molecule disclosed herein operably-linked to the expression vector useful for expressing the nucleic acid molecule in a cell or cell-free extract. A wide variety of expression vectors can be employed for expressing a nucleic acid molecule encoding a NTNHA polypeptide described herein including, without limitation, a viral expression vector (e.g., retroviruses, vaccinia virus, adeno-associated virus, herpes viruses, or bovine papilloma virus), a prokaryotic expression vector, a eukaryotic expression vectors, such as, e.g., a yeast expression vector, an insect expression vector, a mammalian expression vector, and a cell-free extract expression vector. In one embodiment, the expression vector is a baculovirus expression vector. Suitable expression vectors include, without limitation, Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen) or baculovirus-derived vectors. Expression vectors derived from viruses may be used for delivery of the nucleic acids of the invention into a targeted cell population. A number of expression vectors for producing fusions with affinity moieties such as those described herein are available in the art. The selection, making and use of an appropriate expression vector are routine procedures undertaken by the skilled practitioner.

Host Cells

Another aspect of the invention relates to a cell in which one or more of the molecules described herein (e.g., the NTNHA polypeptide and/or the BoNT polypeptide) is propagated and/or expressed. Such a cell is referred to as a host cell. Host cells may be genetically modified to express the molecules described herein, such as by transfection with a vector encoding the proteins, and/or may express one or more of the molecules (e.g., the BoNT) naturally. In one embodiment, the host cell comprises a nucleic acid that encodes the NTNHA polypeptide (e.g., in the context of a vector). In one embodiment, the host cell expresses the nucleic acid (e.g. from an expression vector). In some embodiments, cells used in accordance with the present invention include prokaryotic cells and eukaryotic cells. Non-limiting examples of prokaryotic cell are *Escherichia coli* cells, *Clostridium botulinum* cell, *Clostridium tetani* cells, *Clostridium beratti* cells, *Clostridium butyricum* cells, or *Clostridium perfringens* cells. Non-limiting examples of eukaryotic cells are insect cells, yeast cells, amphibian cells, mammalian cell, plant cells. Non-limiting examples of insect cells are *Spodoptera frupperda* cells, *Aedes albopictus* cells, *Trichoplusia ni* cells, *Estigmene acrea* cells, *Bombyx mori* cells and *Drosophila melanogaster* cells. Non-limiting examples of yeast cells are *Saccharomyces cerevisiae* cells, *Schizosaccharomyces pombe* cells, *Pichia pastoris* cells, *Hansenula polymorpha* cells, *Kluyveromyces lactis* cells and *Yarrowia lipolytica* cells.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages can mean±1%, or ±5%, or ±10%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention is further illustrated by the following examples, which should not be construed as further limiting.

EXAMPLES

Example 1

A New Method for Purifying and Activating BoNTs

Herein is proposed a new method to purify and activate un-tagged, natural forms of BoNTs through simple steps of affinity purification. This method is based on a unique feature of BoNTs: these toxins naturally form a dimer complex with its chaperon protein, known as NTNHA. The biological purpose of this dimer is to protect toxins from proteases and the harsh acidic environment in the gastrointestinal (GI) tract. The interactions between BoNTs and NTNHA are pH-dependent: they bind at pH<7, and dissociate from each other at pH>7.4. Therefore, introducing an affinity tag onto the NTNHA can be utilized to isolate the natural forms of BoNTs in solutions with pH<7. Bound BoNTs can then be released by simply raising the pH of the solution to >pH 7.4. In another words, instead of putting an affinity tag onto BoNTs, its binding partner can be tagged. This allows the production of natural forms of BoNTs through convenient affinity purification method.

In addition to purification, BoNTs need to be activated by limited proteolysis. Recombinant BoNTs are usually activated post-purification with an endoproteinase (such as trypsin). This method has several drawbacks: 1) there are chances for non-specific cutting by the endoproteinase, which compromises toxin activity and yield; 2) the endoproteinase needs to be removed after the reaction is completed, requiring an additional separation step that compromises yield and activity of toxins.

The activation site on BoNTs is still exposed on the surface of BoNT-NTNHA complex, whereas other susceptible sites of BoNTs are often protected in the complex. This provides an opportunity to treat toxins with the endoproteinase while the toxin is still in the complex with NTNHA. This approach addresses both problems in previous methods: 1) NTNHA will protect toxins from non-specific cutting by the endoproteinase; 2) the endoproteinase can be easily removed in a single washing step along with all other non-toxin proteins that do not bind to NTNHA.

Results

Each naturally occurring BoNT has its own, naturally occurring NTNHA partner. BoNT/B and NTNHA/B were used as prototypes to establish the feasibility of our approach. Briefly, the NTNHA/B was expressed as a fusion protein with the commonly used GST tag (Glutathione-S-transferase). The GST-NTNHA/B was purified, immobilized on Glutathione beads, and was subsequently equilibrated with the toxin binding buffer (pH=6). This resin was then added to *E. Coli* cell lysate containing recombinantly expressed BoNT/B and incubated for 1 hour at 4° C. to allow for complex formation under pH 6 conditions. Subsequently, the bead-bound complex was washed with the binding buffer to remove non-specific contaminants and unbound proteins. Bound BoNT/B was either eluted from beads using a pH 8 elution buffer, or subjected to trypsin treatment to be activated.

Figure 1B:
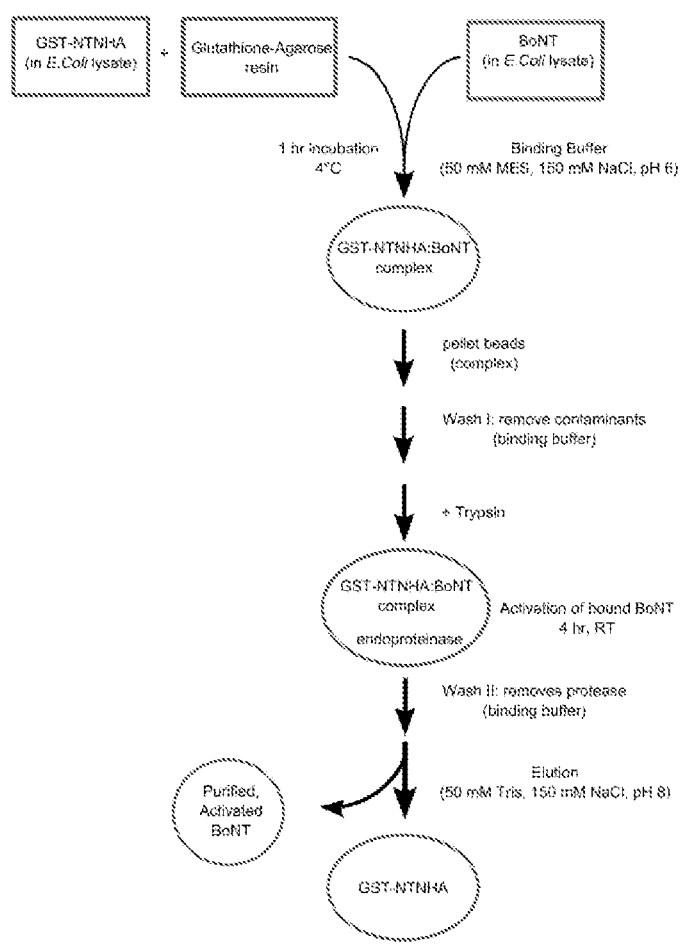
Figures 2A, 2B:
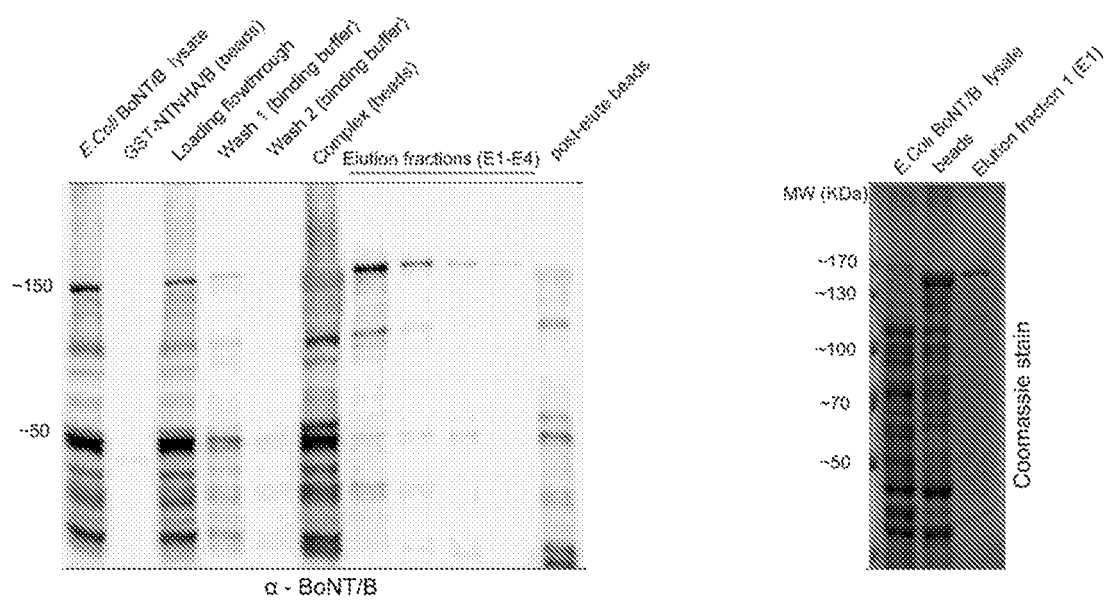
Figures 3A, 3B:
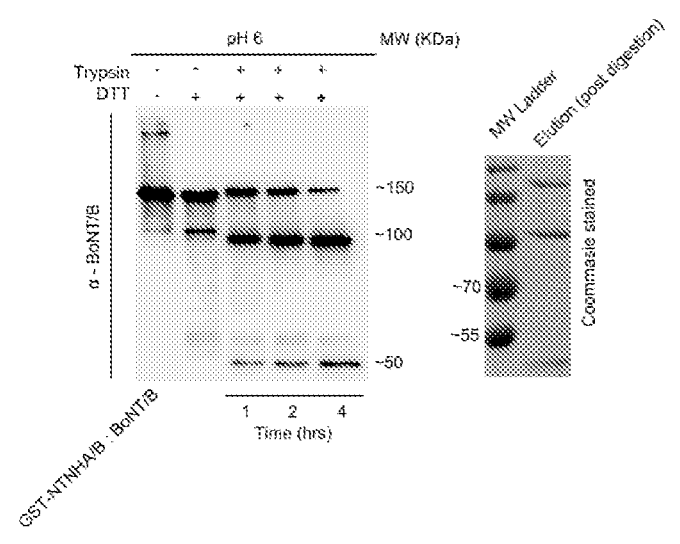

The purification principle and steps are illustrated schematically in FIG. 1A and FIG. 1B. The results indicated that BoNT/B can be efficiently purified from crude bacterial lysates using this method (FIG. 2A), with high yield and purity of final protein (FIG. 2B). A fraction of the resin containing the NTNHA/B:BoNT/B complex was subjected to trypsin-mediated cleavage. The results, shown in FIG. 3A and FIG. 3B, indicate BoNT can be efficiently activated within a few hours on beads in the complex, and can be subsequently eluted from the beads to produce native, active toxin.

Figure 4:
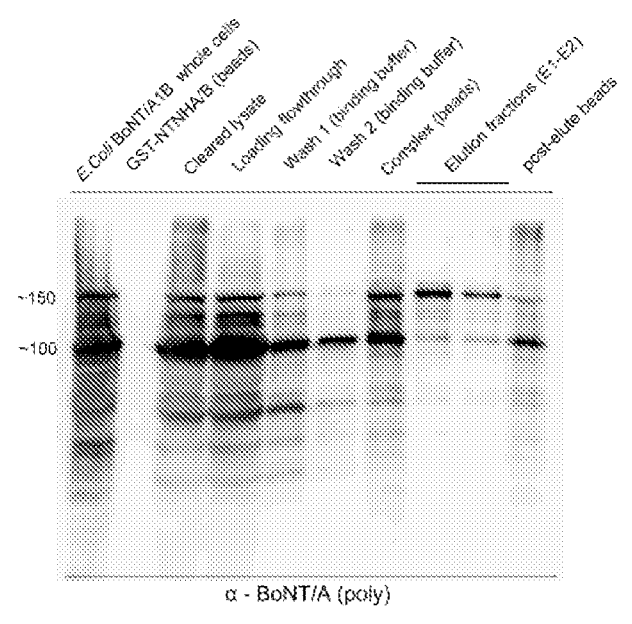

Whether NTNHA that is specific to one serotype can be used to purify chimeric toxins that contain a segment of that toxin, particularly the receptor binding domain was explored. The receptor binding domain mediates the majority of interactions between NTNHA and BoNT. The results, shown in FIG. 4, indicate the successful use of NTNHA/B to purify a hybrid toxin (BoNT/A1B) containing the BoNT/B receptor binding domain.

These experimental results serve as proof of concept of a method that can be used to purify widely used therapeutic toxin: BoNT/A (with NTNHA/A) and BoNT/B (with NTNHA/B), purify other serotypes of BoNTs (with suitable NTNHAs), purify recombinant BoNTs containing mutations, purify chimeric BoNTs (with NTNHA that binds to the receptor binding domain or specifically designed chimeric NTNHA proteins). Advantages of this method are 1) the ability to purify BoNTs with natural N- and C-terminals that are expressed recombinantly, through convenient affinity purification, 2) mild buffer conditions (pH 6-8) minimize any potential damage to toxins, 3) specific pH dependent binding and elution yields highly pure toxins conveniently, reducing the need for further purification, 4) protection from NTNHA reduces non-specific cutting by the activating protease during the activation step, and 5) activation by protease prior to elution of toxins, abolishes the need to separately remove the protease.

Materials and Methods

Protein Expression and Purification. NTNHA/B was expressed in *E. Coli* as a Glutathione-S-Transferase fusion protein (GST-NTNHA/B) with the GST being fused to the N-terminus of the NTNHA/B protein; BoNT/B was expressed in *E. Coli* with a C-terminal $His_6$ tag (SEQ ID NO: 1). Bacterial cultures (1 L) were grown at 37 degree and protein expression was induced with the addition of Isopropyl β-D-1-thiogalactopyranoside (IPTG) (250 µM) when the culture optical density at 600 nm ($OD_{600}$) reached ~0.6 AU. The cultures were then transferred to a 20 degree shaking incubator for overnight expression (~16 hrs). Bacteria were harvested by centrifugation at 5500×g and the resulting pellets were frozen until purification. BoNT/B pellets were thawed and solubilized in binding buffer (50 mM MES, 150 mM NaCl, pH 6) with 5 ml/gram of dry bacterial pellet; NTNHA/B pellet were thawed and solubilized in a different binding buffer (50 mM Tris, 150 mM NaCl, pH 8). 1 mM of phenylmethylsulfonyl fluoride (PMSF) was added before lysis by sonication on ice (Branson Sonifier 250) for 15 min (3×5 min, 50% power). The crude lysate was then cleared by centrifugation (30,000×g, 15 min) and the supernatant was filtered using 0.45 µm syringe filters (Nalgene).

GST-NTNHA/B purification. 600 µL Pierce Glutathione-Agarose beads (50% slurry; Thermo) equilibrated with binding buffer was added to ~20 mL of GST-NTNHA/B supernatant and allowed to batch bind for 1 hr at 4 degree. The beads were recovered by centrifugation (700×g) and washed twice with 3 resin bed volumes of binding buffer (50 mM Tris, 150 mM NaCl, pH 8). The estimated concentration of purified GST-NTNHA/B was ~0.6 mg/mL (BCA assay and SDS-PAGE analysis).

pH-dependent complexation; protease activation; and elution of purified BoNT. The agarose beads harboring GST-NTNHA/B were added to ~5 mL of BoNT/B cleared *E. Coli* lysate for batch binding for 2 hrs at 4 degree in a rocking conical tube. The beads were harvested by (700×g) and washed twice with 3× resin bed volumes of binding buffer (50 mM MES, 150 mM NaCl, pH 6).

Trypsin or Lys-C endoproteinase (Sigma-Aldrich) was added at a molar ratio of 1:10 at pH 6 (on beads) to activate the NTNHA-bound toxin in a final volume of 500 µL. The reaction proceeded on a rotating platform at room temperature and monitored for 4 hrs by sampling small aliquots for subsequent analysis. The resin was washed twice with binding buffer to remove the proteases and unbound impurities. The purified and activated BoNT was eluted with two resin volumes of high pH buffer (50 mM Tris, 150 mM NaCl, pH 8).

SDS-PAGE and WB analysis. 10 µL of all samples (with or without the reducing agent DTT) were applied to 9% SDS-PAGE gels. After separation, the gel was stained with Coomassie stain or subjected to standard immunoblotting analysis. A human monoclonal antibody was used to detect BoNT/B and a polyclonal rabbit antibody was used to detect BoNT/A1B chimeric toxin.

Example 2

Facile, Direct Isolation of Recombinant BoNTs from Crude Bacterial Lysates

The association between BoNT and NTNHA is facilitated by numerous pH sensors on the two molecules that form specific surface recognition (Gu et al. 2012). This interlocked complex protects active toxin from the harsh acidic environment through which it must traverse to reach its cellular destinations.

The present Example confirms feasibility of isolating a recombinant full-length BoNT (inactive BoNT/B, hereafter termed BoNT/B$_{\{RY\}}$) that is expressed in *E. coli*, as described herein. The complex partner that facilitates toxin isolation is a GST-tagged compatible serotype of its recombinant complex partner, NTNHA/B. The GST-tagged NTNHA-B molecule and the BoNT/B$_{\{RY\}}$ were expressed separately in *E. coli* hosts and protein production was achieved using standard auto-induction methods (Studier 2005). For GST-NTNHA-B isolation, a one-step batch purification with agarose-glutathione beads was performed as described in methods. The immobilized GST-NTNHA-B was stable for short-medium term storage at 4 degree for approximately one week, although longer term storage lead to possible spontaneous nicking as reported previously (Sagane et al. 2002; Gu et al. 2012). This reagent was subsequently used to isolate BoNT/B$_{RY}$ and the chimeric BoNT/A1$_{\{RY\}}$B1 in a simple workflow (FIG. 6B), where the agarose beads were the bait in pulling the recombinant toxins out of crude lysates under favorable conditions (e.g. pH 6.0, 150 mM NaCl). SDS-Page analysis of relevant fractions from the purification scheme is shown in FIG. 6C. The regenerated GST-NTNHA/B after elution can be readily used in another cycle of purification to isolate more compatible toxins from fresh or alternative extracts. The eluted full-length toxin is selectively released from the complex upon buffer exchange on the beads and can be visualized on SDS-PAGE or by western blot (WB) analysis (FIG. 7A). Moreover, such mild conditions for isolating full-length (FL) toxins are more likely to preserve its protease activity and functional roles in binding its cellular targets. As the canonical neuronal receptor for BoNT/B, a Synaptotagmin derived labeled peptide is shown to interact with the isolated full-length toxin in an in-vitro fluorescence anisotropy binding assay (FIG. 7B).

The Complexed Toxin is Efficiently Activated by Exogenous Proteases

Figure 8A:
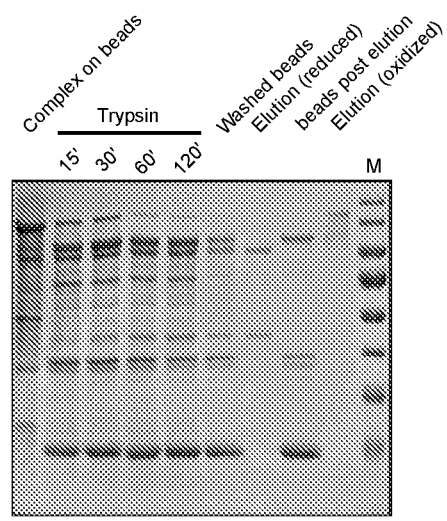
FIGS. 8A-8C show complexed BoNT is efficiently activated yet protected from non-specific cleavage.
Figure 8B:
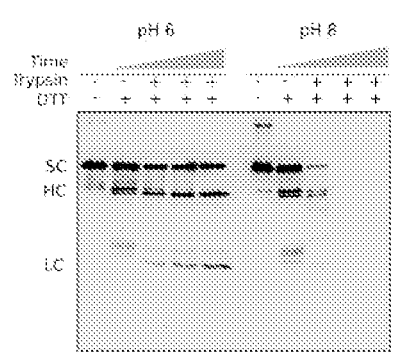
Figure 8C:
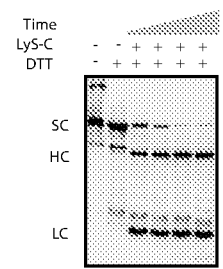

As dichain (AB) toxins, BoNTs are expressed as a single polypeptide chain that undergoes activation to generate a functional molecule linked by a disulfide bridge between the heavy and light chains. "Nicking" by exogenous or endogenous proteases that cleave the polypeptide chain between two conserved cysteines that maintain a covalent bridge between the LC and HC can improve potency, and may be required for maximum potency (FIG. 6A). The present Example documents that addition of such proteases (e.g., specifically of an exogenous protease) can be incorporated into purification protocol workflows as described herein and, in some embodiments, can help maximize recovery of active toxins. For example, complexed GST-NTNHA/B:BoNT/B$_{\{RY\}}$ can be cleaved by catalytic amounts of trypsin or Lys-C endoproteinase under mild conditions at room temperature and the nicked toxin can be selectively released in higher pH buffer. FIGS. 8A-8C show time courses of activating complexed single chain BoNT//B$_{\{RY\}}$ to release the ~50 kD protease domain (LC) and the ~100 kDa HC in samples that contain dithiothreitol (DTT). The lower pH binding conditions and the lower activity of the proteases (Kasserra & Laidler 1969; Jekel et al. 1983) play a protective role from nonspecific/excessive degradation of the toxin and/or NTNHA (FIG. 8B). The purity and extent of toxin nicking can be visualized either on SDS-PAGE gel or detected by WB analysis (FIG. 8A and FIG. 8C).

Chimeric Recombinant Toxins can be Isolated Using a Common NTNHA Serotype

Figure 9:
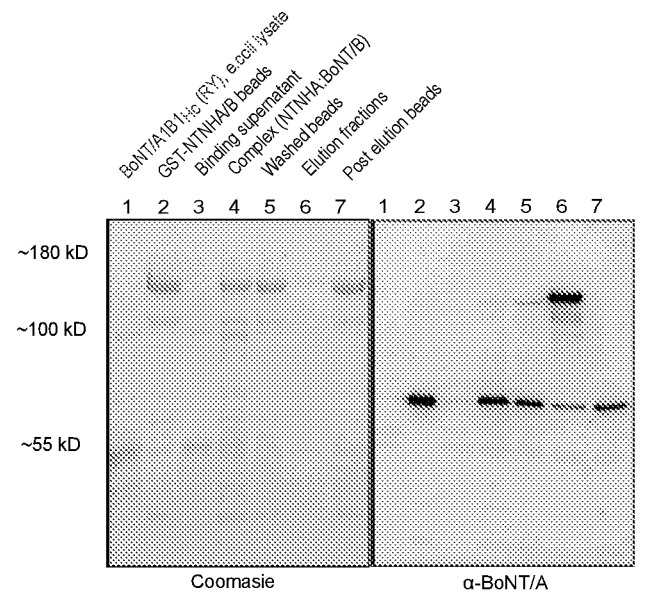

The present Example confirms that a chimeric recombinant botulinum neurotoxin can be purified using a complex-based purification protocol as described herein using various targets that may serve as therapeutic backbones for future biologics. The receptor binding domain of BoNTs mediates most polar contacts with NTNHA (Gu et al. 2012). The present Example confirms that recombinant botulinum neurotoxin can be purified via complex formation with NTNHA. A chimeric recombinant protein (BoNT/A1$_{\{RY\}}$B1) that is constructed from inactive BoNT/A LC, BoNT/A H$_N$, and BoNT/B H$_e$ was used as a proof-of-concept. Using the same recombinant GST-NTNHA/B above, complexation and enrichment of the chimeric protein on the NTNHA beads could be detected despite low expression levels of the toxin (FIG. 9). The cleared lysate for the chimeric toxin contained degradation products and large impurities that often preclude efficient complexation with the immobilized NTNHA. Therefore, the BoNT/A1$_{\{RY\}}$B1 lysate was passed once over, and eluted from a Ni-NTA resin before exposure to the immobilized NTNHA on agarose resin. Subsequent activation profiles with this chimeric toxin may be similar to that of BoNT/B$_{\{RY\}}$, possibly with varying efficiencies.

Discussion

This Example demonstrates isolation of recombinantly expressed BoNTs using a NTNHA/B as a noncovalent progenitor complex partner. Both BoNT/B$_{\{RY\}}$ and NTNHA/B were overexpressed separately in E. coli hosts. The NTNHA/B was expressed as a fusion protein with a GST tag appended to its N-terminus as an affinity moiety towards the solid agarose-glutathione resin. BoNT/B$_{\{RY\}}$ (and the chimeric BoNT/A1$_{\{RY\}}$B1) were expressed as wild-type sequences except for the inactivation mutations and a C-terminal His$_{6X}$ tag. Bacterial lysis in a low pH buffer released these toxins in a lysate that was incubated with the agarose beads harboring GST-NTNHA/B. After complex formation, the solid media is washed extensively to remove impurities; after which the toxins can either be eluted by high pH buffer exchange or activated through an additional step where an exogenous endoprotease is applied to the resin-bound complex.

As confirmed by the findings documented in the present Example, the present disclosure provides a solution for efficiently isolating active, therapeutic BoNTs from various sources under mild conditions. Enhanced methodology to isolate, activate, and elute purified BoNTs can be immensely useful, such as in large-scale production of therapeutic BoNTs. Potential benefits include the following: 1) efficient isolation of recombinant BoNTs from crude lysates under mild conditions unlike those in current practices (Malizio et al. 2000; Donovan 2007); 2) high-purity, activated toxins can be produced using a single purification scheme as it enables extensive washing of contaminates and avoids multiple chromatography steps; 3) the immobilized NTNHA can properly protect from non-specific cleavage of toxin in the activation step, which can be readily incorporated in the purification protocol (as opposed to the common post purification activation). This can increase final yields and homogeneity of the final activated toxin; and 4) the immobilized GST-NTNHA can serve multiple sequential purifications as it is regenerated at the end of every cycle with little loss; and 5) such methodology can be expanded to isolation of chimeric therapeutic toxins with compatible receptor binding domains.

Materials and Methods

Protein Expression and Purification

NTNHA/B was expressed as a Glutathione-S-Transferase fusion protein (GST-NTNHA/B) in a pGEX vector; BoNT/B$_{\{RY\}}$ and BoNT/A1$_{\{RY\}}$B1 were expressed with a C-terminal (His$_{6X}$) tag in a pET32-a vector in E. coli (BL21DE3). Cell cultures (typically 300 mL) were grown in autoinduction media (Formedium™, UK) in baffled 2L flasks at 37° C. with vigorous shaking (>250 RPM). When cultures reached OD of ~0.6, the cell cultures were transferred to a 20° C. shaking incubator for overnight expression (~16 hrs). Cells were harvested by centrifugation at 5500×g and the resulting pellets were frozen at −20° C. until purification. BoNT/B$_{\{RY\}}$ cell pellets were thawed and solubilized in binding buffer (50 mM MES, 150 mM NaCl, pH 6) with 5 ml/gram of dry cell pellet. GST-NTNHA/B cells were thawed and solubilized in TBS binding buffer (50 mM Tris, 150 mM NaCl, pH 8). Phenylmethylsulfonyl fluoride (PMSF) was added to the solubilized cells at a final concentration of 0.1 mM before lysis by sonication on ice (Branson Sonifier 250) for 15 min (3×5 min); 30% power. The crude lysates were then cleared by centrifugation (30,000×g, 15 min) and the supernatant was filtered using 0.45 μm syringe filters (Nalgene).

GST-NTNHA/B Purification

600 μL Pierce Glutathione-Agarose beads (50% slurry; Thermo) were equilibrated with binding buffer and added to ~20 mL of GST-NTNHA/B supernatant and allowed to batch bind for 1 hr at 4° C. on a gently rocking platform. The beads were recovered by centrifugation (700×g) and washed twice with 3× resin bed volumes of binding buffer (1× TBS). The estimated concentration of purified GST-NTNHA/B was typically ~0.5 mg/mL (BCA assay and SDS-PAGE analysis).

Binding, Activation, and Elution of Purified BoNTs

The agarose beads harboring GST-NTNHA/B were added to 10-25 mL of BoNT/B$_{\{RY\}}$ or BoNT/A1$_{\{RY\}}$B1 cleared lysates (in MES, pH 6) buffer and allowed batch binding to proceed for 2 hours at 4° C. in a 50-mL conical tube on a rocking platform. The beads were harvested by (700×g) and washed twice with 3× resin bed volumes of binding buffer (MES, pH 6). If no activation is desired, bound purified toxins may be eluted at this stage as described below.

Trypsin or Lys-C endoproteinase (Sigma-Aldrich) were added at a molar ratio of 1:10 endoproteinase:GST-NTNHA/B at pH 6 (on beads) to activate the bound toxin in a final volume of 500-1000 uL. The reaction proceeded on a rotating (tumbling) platform at room temperature and monitored (either 2-4 hours as in FIG. 8A and FIG. 8C; or overnight at 4° C. as in FIG. 8B) by sampling small aliquots for subsequent analysis. The resin was washed twice with binding buffer to remove the proteases and impurities. The purified and activated BoNT/B$_{\{RY\}}$ was eluted in fractions of two resin volumes of high pH buffer (TBS: 50 mM Tris, 150 mM NaCl, pH 8).

SDS-PAGE and WB Analysis

10 μL of all samples (with or without the reducing agents DTT or βME) were applied to 8-12% SDS-PAGE gels. After separation, gels were stained with Coomassie stain or subjected to standard Western blotting procedure. A monoclonal rabbit antibody (1:5000) was used to detect BoNT/B$_{\{RY\}}$ and a polyclonal rabbit antibody (1:2000) raised against BoNT/A was used to detect BoNT/A1$_{\{RY\}}$B1.

Fluorescence Anisotropy

Human Synaptotagmin 1 (Syt 1) derived peptide (AA 33-53) was synthesized with an N-terminal FITC label (GenScript, Piscataway N.J.) and used as a receptor in the binding experiment at 50-100 nM. The eluted full-length toxins were concentrated in Vivaspin 6 filtration units (10K MWCO, GE). Binding experiments (50 uL) were measured in black 96-well plate (Corning) using a filter-based plate reader (485/520 nm excitation/emission). BoNT/A and BoNT/B Hc were separately expressed and purified and served as negative and positive controls, respectively.

REFERENCES

Blasi, J. et al., 1993. Botulinum neurotoxin A selectively cleaves the synaptic protein SNAP-25. *Nature*, 365 (6442), pp. 160-163.

Bonventre, P. F. & Kempe, L. L., 1959. Physiology of toxin production by *Clostridium botulinum* types A and B. III. Effect of pH and temperature during incubation on growth, autolysis. and toxin production. *Applied microbiology*, 7, pp. 374-377.

Borden Lacy, D. et al., 1998. Crystal structure of botulinum neurotoxin type A and implications for toxicity. *Nature structural & molecular biology*, 5(10), pp. 898-902.

DasGupta, B. R. & Boroff, D. A., 1967. Chromatographic isolation of hemagglutinin-free neurotoxin from crystalline toxin of *Clostridium botulinum* type A. *Biochimica et biophysica acta*, 147(3), pp. 603-605.

Dong, M. et al., 2006. SV2 is the protein receptor for botulinum neurotoxin A. *Science*, 312(5773), pp. 592-596.

Donovan, S., 2007. Botulinum toxin production method. *US Patent*. Available at: https://www.google.com/patents/US7189541 [Accessed Mar. 10, 2017].

Duff, J. T., Wright, G. G., et al., 1957. Studies on immunity to toxins of *Clostridium botulinum*. I. A simplified procedure for isolation of type A toxin. *Journal of bacteriology*, 73(1), pp. 42-47.

Duff, J. T., Klerer, J., et al., 1957. Studies on immunity to toxins of *Clostridium botulinum*. II. Production and purification of type B toxin for toxoid. *Journal of bacteriology*, 73(5), pp. 597-601.

Finzi, E. & Rosenthal, N. E., 2014. Treatment of depression with onabotulinumtoxinA: a randomized, double-blind, placebo controlled trial. *Journal of psychiatric research*, 52, pp. 1-6.

Gu, S. et al., 2012. Botulinum neurotoxin is shielded by NTNHA in an interlocked complex. *Science*, 335(6071), pp. 977-981.

Hexsel, C. et al., 2011. Botulinum toxin type A for aging face and aesthetic uses. *Dermatologic therapy*, 24(1), pp. 54-61.

Jackson, J. L., Kuriyama, A. & Hayashino, Y., 2012. Botulinum toxin A for prophylactic treatment of migraine and tension headaches in adults: a meta-analysis. *JAMA: the journal of the American Medical Association*, 307(16), pp. 1736-1745.

Jankovic, J. & Brin, M. F., 1991. Therapeutic uses of botulinum toxin. *The New England journal of medicine*, 324(17), pp. 1186-1194.

Jekel, P. A., Weijer, W. J. & Beintema, J. J., 1983. Use of endoproteinase Lys-C from Lysobacter enzymogenes in protein sequence analysis. *Analytical biochemistry*, 134 (2), pp. 347-354.

Jiang, Y.-H., Liao, C.-H. & Kuo, H.-C., 2015. Current and potential urological applications of botulinum toxin A. *Nature reviews. Urology*, 12(9), pp. 519-533.

Kasserra, H. P. & Laidler, K. J., 1969. pH Effects in trypsin catalysis. *Canadian journal of chemistry*, 47(21), pp. 4021-4029.

Lee, K. et al., 2014. Molecular basis for disruption of E-cadherin adhesion by botulinum neurotoxin A complex. *Science*, 344(6190), pp. 1405-1410.

Malizio, C. J., Goodnough, M. C. & Johnson, E. A., 2000. Purification of *Clostridium botulinum* type A neurotoxin. *Methods in molecular biology*, 145, pp. 27-39.

Masuyer, G. et al., 2014. Engineered botulinum neurotoxins as new therapeutics. Annual review of pharmacology and toxicology, 54, pp. 27-51.

Montal, M., 2010. Botulinum neurotoxin: a marvel of protein design. Annual review of biochemistry, 79, pp. 591-617.

Pickett, A., 2014. Botulinum Toxin as a Clinical Product: Manufacture and Pharmacology. In Clinical Applications of Botulinum Neurotoxin. Current Topics in Neurotoxicity. Springer New York, pp. 7-49.

Pickett, A. & Perrow, K., 2009. Composition and Molecular Size of *Clostridium botulinum* Type A Toxin-Hemagglutinin Complex. *The protein journal*, 28(5), pp. 248-249.

Rossetto, O., Pirazzini, M. & Montecucco, C., 2014. Botulinum neurotoxins: genetic, structural and mechanistic insights. *Nature reviews. Microbiology*, 12(8), pp. 535-549.

Sagane, Y. et al., 2002. Spontaneous Nicking in the Non-toxic-Nonhemagglutinin Component of the *Clostridium botulinum* Toxin Complex. *Biochemical and biophysical research communications*, 292(2), pp. 434-440.

Schantz, E. J. & Johnson, E. A., 1992. Properties and use of botulinum toxin and other microbial neurotoxins in medicine. *Microbiological reviews*, 56(1), pp. 80-99.

Sifferlin, A., 2017. Botox: The Drug That's Treating Everything. *Time*. Available at: http://time.com/4623409/botox-drug-treating-everything/[Accessed Mar. 10, 2017].

Snipe, P. T. & Sommer, H., 1928. Studies on botulinus toxin 3. Acid precipitation of botulinus toxin. *The Journal of infectious diseases*, 43(2), pp. 152-160.

Studier, F. W., 2005. Protein production by auto-induction in high-density shaking cultures. *Protein expression and purification*, 41(1), pp. 207-234.

Truong, D. D. & Jost, W. H., 2006. Botulinum toxin: clinical use. *Parkinsonism & related disorders,* 12(6), pp. 331-355.

Tse, C. K. et al., 1982. Preparation and characterisation of homogeneous neurotoxin type A from *Clostridium botulinum*. Its inhibitory action on neuronal release of acetylcholine in the absence and presence of beta-bungarotoxin. *European journal of biochemistry/FEBS,* 122(3), pp. 493-500.

Visco, A. G. et al., 2012. Anticholinergic therapy vs. onabotulinumtoxina for urgency urinary incontinence. *The New England journal of medicine,* 367(19), pp. 1803-1813.

What is claimed:

1. A composition comprising:
a complex of:
polypeptide (the "NTNHA polypeptide") comprising a NTNHA polypeptide covalently linked with a heterologous affinity moiety; which NTNHA polypeptide is complexed with
a BoNT protein, or a polypeptide comprising a BoNT receptor binding domain (the "BoNT RBD polypeptide"), comprising a protease cleavage site;
wherein the complex is non-covalently associated with:
a target of the heterologous affinity moiety; and
further wherein the protease cleavage site is accessible so that, when the complex is contacted with the protease, the BoNT RBD polypeptide is cleaved into first and second portions, at least one of which remains complexed with the NTNHA polypeptide.

2. The composition of claim 1, wherein the NTNHA and the affinity moiety are expressed as a fusion protein.

3. The composition of claim 1, wherein the affinity moiety specifically binds a binding target under conditions of about pH 6 to about pH 8.

4. The composition of claim 1, wherein the affinity moiety is selected from the group consisting of glutathione-S-transferase (GST), C-myc tag, Chitin-binding domain, Streptavidin binding protein (SBP), Cellulose-binding domain, Calmodulin-binding peptide, S-tag, Strep-tag II, FLA, Protein A, Protein G, histidine affinity tag (HAT), Poly-His, and maltose binding protein (MBP).

5. The composition of claim 1, wherein the NTNHA is from serotype B, A, C1, D, E, F, or G.

6. The composition of claim 5, wherein the NTNHA is from serotype B.

7. The composition of claim 1, wherein the BoNT or the polypeptide comprises a modified receptor binding domain of Clostridial botulinum serotype B (B-Hc).

8. The composition of claim 1, wherein:
i) the affinity moiety is located at a position selected from the group consisting of the N-terminus of NTNHA amino acid sequence, the C-terminus of NTNHA amino acid sequence, and internal to the NTNHA amino acid sequence;
ii) the affinity moiety specifically binds a binding target under conditions of about pH 6 to about pH 8; and/or
iii) the affinity moiety is selected from the group consisting of glutathione-S-transferase (GST), C-myc tag, Chitin-binding domain, Streptavidin binding protein (SBP), Cellulose-binding domain, Calmodulin-binding peptide, S-tag, Strep-tag II, FLA, Protein A, Protein G, histidine affinity tag (HAT), Poly-His, and maltose binding protein (MBP).

9. The composition of claim 1, wherein the binding target is stably attached to a matrix.

10. The composition of claim 1, wherein the complex is intact in solution at pH 6 and disrupted in solution at pH 8.

11. A composition comprising:
a complex of:
polypeptide (the "NTNHA polypeptide") comprising a NTNHA polypeptide covalently linked with a heterologous affinity moiety; which NTNHA polypeptide is complexed with
at least one of first and second cleaved portions of a BoNT protein, or of a polypeptide comprising a BoNT receptor binding domain (the "BoNT RBD polypeptide"), which portions represent fragments that flank a protease cleavage site in the intact BoNT protein or BoNT RBD polypeptide;
wherein the complex is non-covalently associated with:
a target of the heterologous affinity moiety.

12. The composition of claim 11, wherein the NTNHA and the affinity moiety are covalently linked as a fusion protein.

13. The composition of claim 11, wherein the affinity moiety specifically binds a binding target under conditions of about pH 6 to about pH 8.

14. The composition of claim 11, wherein the affinity moiety is selected from the group consisting of glutathione-S-transferase (GST), C-myc tag, Chitin-binding domain, Streptavidin binding protein (SBP), Cellulose-binding domain, Calmodulin-binding peptide, S-tag, Strep-tag II, FLA, Protein A, Protein G, histidine affinity tag (HAT), Poly-His, and maltose binding protein (MBP).

15. The composition of claim 11, wherein the NTNHA is from serotype B, A, C1, D, E, F, or G.

16. The composition of claim 15, wherein the NTNHA is from serotype B.

17. The composition of claim 11, wherein the BoNT or the polypeptide comprises a modified receptor binding domain of Clostridial botulinum serotype B (B-Hc).

18. The composition of claim 11, wherein:
i) the affinity moiety is located at a position selected from the group consisting of the N-terminus of NTNHA amino acid sequence, the C-terminus of NTNHA amino acid sequence, and internal to the NTNHA amino acid sequence;

ii) the affinity moiety specifically binds a binding target under conditions of about pH 6 to about pH 8; and/or iii) the affinity moiety is selected from the group consisting of glutathione-S-transferase (GST), C-myc tag, Chitin-binding domain, Streptavidin binding protein (SBP), Cellulose-binding domain, Calmodulin-binding peptide, S-tag, Strep-tag II, FLA, Protein A, Protein G, histidine affinity tag (HAT), Poly-His, and maltose binding protein (MBP).

19. The composition of claim 11, wherein the binding target is stably attached to a matrix.

20. The composition of claim 11, wherein the complex is intact in solution at pH 6 and disrupted in solution at pH 8.

* * * * *

SEQUENCE LISTING

```
<160> NUMBER OF SEQ ID NOS: 30

<210> SEQ ID NO 1
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 1

His His His His His His
1               5

<210> SEQ ID NO 2
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      Enterokinase peptide"

<400> SEQUENCE: 2

Asp Asp Asp Asp Lys
1               5

<210> SEQ ID NO 3
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Factor Xa peptide"

<400> SEQUENCE: 3

Ile Glu Gly Arg
1

<210> SEQ ID NO 4
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Factor Xa peptide"

<400> SEQUENCE: 4

Ile Asp Gly Arg
1

<210> SEQ ID NO 5
<211> LENGTH: 7
<212> TYPE: PRT
<213> ORGANISM: Tobacco Etch virus

<400> SEQUENCE: 5

Glu Asn Leu Tyr Phe Gln Gly
```

```
1               5

<210> SEQ ID NO 6
<211> LENGTH: 6
<212> TYPE: PRT
<213> ORGANISM: Unknown
<220> FEATURE:
<221> NAME/KEY: source
<223> OTHER INFORMATION: /note="Description of Unknown:
      Thrombin peptide"

<400> SEQUENCE: 6

Leu Val Pro Arg Gly Ser
1               5

<210> SEQ ID NO 7
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      PreScission peptide"

<400> SEQUENCE: 7

Leu Glu Val Leu Phe Gln Gly Pro
1               5

<210> SEQ ID NO 8
<211> LENGTH: 10
<212> TYPE: PRT
<213> ORGANISM: Unknown
<220> FEATURE:
<221> NAME/KEY: source
<223> OTHER INFORMATION: /note="Description of Unknown:
      myc peptide"

<400> SEQUENCE: 8

Glu Gln Lys Leu Ile Ser Glu Glu Asp Leu
1               5                   10

<210> SEQ ID NO 9
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      IRS peptide"

<400> SEQUENCE: 9

Arg Tyr Ile Arg Ser
1               5

<210> SEQ ID NO 10
<211> LENGTH: 6
<212> TYPE: PRT
<213> ORGANISM: Bovine papillomavirus 1

<400> SEQUENCE: 10

Asp Thr Tyr Arg Tyr Ile
1               5

<210> SEQ ID NO 11
<211> LENGTH: 6
<212> TYPE: PRT
<213> ORGANISM: Bovine papillomavirus 1
```

```
<400> SEQUENCE: 11

Thr Asp Phe Leu Tyr Lys
1               5

<210> SEQ ID NO 12
<211> LENGTH: 9
<212> TYPE: PRT
<213> ORGANISM: Polyomavirus sp.

<400> SEQUENCE: 12

Glu Glu Glu Glu Tyr Met Pro Met Glu
1               5

<210> SEQ ID NO 13
<211> LENGTH: 11
<212> TYPE: PRT
<213> ORGANISM: Simian virus 40

<400> SEQUENCE: 13

Lys Pro Pro Thr Pro Pro Pro Glu Pro Glu Thr
1               5                   10

<210> SEQ ID NO 14
<211> LENGTH: 11
<212> TYPE: PRT
<213> ORGANISM: Enterobacteria phage T7

<400> SEQUENCE: 14

Met Ala Ser Met Thr Gly Gly Gln Gln Met Gly
1               5                   10

<210> SEQ ID NO 15
<211> LENGTH: 12
<212> TYPE: PRT
<213> ORGANISM: Herpes simplex virus

<400> SEQUENCE: 15

Gln Pro Glu Leu Ala Pro Glu Asp Pro Glu Asp Cys
1               5                   10

<210> SEQ ID NO 16
<211> LENGTH: 11
<212> TYPE: PRT
<213> ORGANISM: Vesicular stomatitis virus

<400> SEQUENCE: 16

Tyr Thr Asp Ile Glu Met Asn Arg Leu Gly Lys
1               5                   10

<210> SEQ ID NO 17
<211> LENGTH: 7
<212> TYPE: PRT
<213> ORGANISM: Unknown
<220> FEATURE:
<221> NAME/KEY: source
<223> OTHER INFORMATION: /note="Description of Unknown:
      Anti-Xpress peptide"

<400> SEQUENCE: 17

Asp Leu Tyr Asp Asp Asp Lys
1               5

<210> SEQ ID NO 18
<211> LENGTH: 14
<212> TYPE: PRT
```

```
<213> ORGANISM: Paramyxovirus SV5

<400> SEQUENCE: 18

Gly Lys Pro Ile Pro Asn Pro Leu Leu Gly Leu Asp Ser Thr
1               5                   10

<210> SEQ ID NO 19
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Asp Tyr Lys Asp Asp Asp Asp Lys
1               5

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(10)
<223> OTHER INFORMATION: /note="This sequence may encompass 4-10
      residues"

<400> SEQUENCE: 20

His His His His His His His His His His
1               5                   10

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Trp Ser His Pro Gln Phe Glu Lys
1               5

<210> SEQ ID NO 22
<211> LENGTH: 1193
<212> TYPE: PRT
<213> ORGANISM: Clostridium botulinum

<400> SEQUENCE: 22

Met Asn Ile Asn Asp Asn Leu Ser Ile Asn Ser Pro Val Asp Asn Lys
1               5                   10                  15

Asn Val Val Val Arg Ala Arg Lys Thr Asp Thr Val Phe Lys Ala
                20                  25                  30

Phe Lys Val Ala Pro Asn Ile Trp Val Ala Pro Glu Arg Tyr Tyr Gly
            35                  40                  45

Glu Ser Leu Ser Ile Asp Glu Glu Tyr Lys Val Asp Gly Gly Ile Tyr
        50                  55                  60

Asp Ser Asn Phe Leu Ser Gln Asp Ser Glu Lys Asp Lys Phe Leu Gln
65                  70                  75                  80
```

-continued

Ala Ile Ile Thr Leu Leu Lys Arg Ile Asn Ser Thr Asn Ala Gly Glu
              85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
    130                 135                 140

Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Thr Glu Ile Trp Phe Gln Pro Phe Leu Thr
        195                 200                 205

Tyr Lys Tyr Asp Glu Phe Tyr Ile Asp Pro Ala Ile Glu Leu Ile Lys
    210                 215                 220

Cys Leu Ile Lys Ser Leu Tyr Phe Leu Tyr Gly Ile Lys Pro Ser Asp
225                 230                 235                 240

Asp Leu Val Ile Pro Tyr Arg Leu Arg Ser Glu Leu Glu Asn Ile Glu
                245                 250                 255

Tyr Ser Gln Leu Asn Ile Val Asp Leu Leu Val Ser Gly Gly Ile Asp
            260                 265                 270

Pro Lys Phe Ile Asn Thr Asp Pro Tyr Trp Phe Thr Asp Asn Tyr Phe
        275                 280                 285

Ser Asn Ala Lys Lys Val Phe Glu Asp His Arg Asn Ile Tyr Glu Thr
    290                 295                 300

Glu Ile Glu Gly Asn Asn Ala Ile Gly Asn Asp Ile Lys Leu Arg Leu
305                 310                 315                 320

Lys Gln Lys Phe Arg Ile Asn Ile Asn Asp Ile Trp Glu Leu Asn Leu
                325                 330                 335

Asn Tyr Phe Ser Lys Glu Phe Ser Ile Met Met Pro Asp Arg Phe Asn
            340                 345                 350

Asn Ala Leu Lys His Phe Tyr Arg Lys Gln Tyr Tyr Lys Ile Asp Tyr
        355                 360                 365

Pro Glu Asn Tyr Ser Ile Asn Gly Phe Val Asn Gly Gln Ile Asn Ala
    370                 375                 380

Gln Leu Ser Leu Ser Asp Arg Asn Gln Asp Ile Ile Asn Lys Pro Glu
385                 390                 395                 400

Glu Ile Ile Asn Leu Leu Asn Gly Asn Asn Val Ser Leu Met Arg Ser
                405                 410                 415

Asn Ile Tyr Gly Asp Gly Leu Lys Ser Thr Val Asp Asp Phe Tyr Ser
            420                 425                 430

Asn Tyr Lys Ile Pro Tyr Asn Arg Ala Tyr Glu Tyr His Phe Asn Asn
        435                 440                 445

Ser Asn Asp Ser Ser Leu Asp Asn Val Asn Ile Gly Val Ile Asp Asn
    450                 455                 460

Ile Pro Glu Ile Ile Asp Val Asn Pro Tyr Lys Glu Asn Cys Asp Lys
465                 470                 475                 480

Phe Ser Pro Val Gln Lys Ile Ser Thr Arg Glu Ile Asn Thr Asn
                485                 490                 495

-continued

```
Ile Pro Trp Pro Ile Asn Tyr Leu Gln Ala Gln Asn Thr Asn Asn Glu
            500                 505                 510

Lys Phe Ser Leu Ser Ser Asp Phe Val Glu Val Val Ser Ser Lys Asp
            515                 520                 525

Lys Ser Leu Val Tyr Ser Phe Leu Ser Asn Val Met Phe Tyr Leu Asp
            530                 535                 540

Ser Ile Lys Asp Asn Ser Pro Ile Asp Thr Asp Lys Lys Tyr Tyr Leu
545                 550                 555                 560

Trp Leu Arg Glu Ile Phe Arg Asn Tyr Ser Phe Asp Ile Thr Ala Thr
            565                 570                 575

Gln Glu Ile Asn Thr Asn Cys Gly Ile Asn Lys Val Val Thr Trp Phe
            580                 585                 590

Gly Lys Ala Leu Asn Ile Leu Asn Thr Ser Asp Ser Phe Val Glu Glu
            595                 600                 605

Phe Gln Asn Leu Gly Ala Ile Ser Leu Ile Asn Lys Lys Glu Asn Leu
            610                 615                 620

Ser Met Pro Ile Ile Glu Ser Tyr Glu Ile Pro Asn Asp Met Leu Gly
625                 630                 635                 640

Leu Pro Leu Asn Asp Leu Asn Glu Lys Leu Phe Asn Ile Tyr Ser Lys
            645                 650                 655

Asn Thr Ala Tyr Phe Lys Lys Ile Tyr Tyr Asn Phe Leu Asp Gln Trp
            660                 665                 670

Trp Thr Gln Tyr Tyr Ser Gln Tyr Phe Asp Leu Ile Cys Met Ala Lys
            675                 680                 685

Arg Ser Val Leu Ala Gln Glu Thr Leu Ile Lys Arg Ile Ile Gln Lys
            690                 695                 700

Lys Leu Ser Tyr Leu Ile Gly Asn Ser Asn Ile Ser Ser Asp Asn Leu
705                 710                 715                 720

Ala Leu Met Asn Leu Thr Thr Thr Asn Thr Leu Arg Asp Ile Ser Asn
            725                 730                 735

Glu Ser Gln Ile Ala Met Asn Asn Val Asp Ser Phe Leu Asn Asn Ala
            740                 745                 750

Ala Ile Cys Val Phe Glu Ser Asn Ile Tyr Pro Lys Phe Ile Ser Phe
            755                 760                 765

Met Glu Gln Cys Ile Asn Asn Ile Asn Ile Lys Thr Lys Glu Phe Ile
            770                 775                 780

Gln Lys Cys Thr Asn Ile Asn Glu Asp Glu Lys Leu Gln Leu Ile Asn
785                 790                 795                 800

Gln Asn Val Phe Asn Ser Leu Asp Phe Glu Phe Leu Asn Ile Gln Asn
            805                 810                 815

Met Lys Ser Leu Phe Ser Ser Glu Thr Ala Leu Leu Ile Lys Glu Glu
            820                 825                 830

Thr Trp Pro Tyr Glu Leu Val Leu Tyr Ala Phe Lys Glu Pro Gly Asn
            835                 840                 845

Asn Val Ile Gly Asp Ala Ser Gly Lys Asn Thr Ser Ile Glu Tyr Ser
            850                 855                 860

Lys Asp Ile Gly Leu Val Tyr Gly Ile Asn Ser Asp Ala Leu Tyr Leu
865                 870                 875                 880

Asn Gly Ser Asn Gln Ser Ile Ser Phe Ser Asn Asp Phe Phe Glu Asn
            885                 890                 895

Gly Leu Thr Asn Ser Phe Ser Ile Tyr Phe Trp Leu Arg Asn Leu Gly
            900                 905                 910

Lys Asp Thr Ile Lys Ser Lys Leu Ile Gly Ser Lys Glu Asp Asn Cys
```

```
                915                 920                 925
Gly Trp Glu Ile Tyr Phe Gln Asp Thr Gly Leu Val Phe Asn Met Ile
    930                 935                 940

Asp Ser Asn Gly Asn Glu Lys Asn Ile Tyr Leu Ser Asp Val Ser Asn
945                 950                 955                 960

Asn Ser Trp His Tyr Ile Thr Ile Ser Val Asp Arg Leu Lys Glu Gln
                965                 970                 975

Leu Leu Ile Phe Ile Asp Asp Asn Leu Val Ala Asn Glu Ser Ile Lys
            980                 985                 990

Glu Ile Leu Asn Ile Tyr Ser Ser Asn Ile Ile Ser Leu Leu Ser Glu
        995                 1000                1005

Asn Asn Pro Ser Tyr Ile Glu Gly Leu Thr Ile Leu Asn Lys Pro
    1010                1015                1020

Thr Thr Ser Gln Glu Val Leu Ser Asn Tyr Phe Glu Val Leu Asn
    1025                1030                1035

Asn Ser Tyr Ile Arg Asp Ser Asn Glu Glu Arg Leu Glu Tyr Asn
    1040                1045                1050

Lys Thr Tyr Gln Leu Tyr Asn Tyr Val Phe Ser Asp Lys Pro Ile
    1055                1060                1065

Cys Glu Val Lys Gln Asn Asn Asn Ile Tyr Leu Thr Ile Asn Asn
    1070                1075                1080

Thr Asn Asn Leu Asn Leu Gln Ala Ser Lys Phe Lys Leu Leu Ser
    1085                1090                1095

Ile Asn Pro Asn Lys Gln Tyr Val Gln Lys Leu Asp Glu Val Ile
    1100                1105                1110

Ile Ser Val Leu Asp Asn Met Glu Lys Tyr Ile Asp Ile Ser Glu
    1115                1120                1125

Asp Asn Arg Leu Gln Leu Ile Asp Lys Asn Asn Ala Lys Lys
    1130                1135                1140

Met Ile Ile Ser Asn Asp Ile Phe Ile Ser Asn Cys Leu Thr Leu
    1145                1150                1155

Ser Tyr Asn Gly Lys Tyr Ile Cys Leu Ser Met Lys Asp Glu Asn
    1160                1165                1170

His Asn Trp Met Ile Cys Asn Asn Asp Met Ser Lys Tyr Leu Tyr
    1175                1180                1185

Leu Trp Ser Phe Lys
    1190

<210> SEQ ID NO 23
<211> LENGTH: 1159
<212> TYPE: PRT
<213> ORGANISM: Clostridium botulinum

<400> SEQUENCE: 23

Met Lys Ile Asn Asn Phe Asn Ile Asp Ser Leu Ile Asp Asn Arg
1               5                   10                  15

Asp Val Ala Ile Val Arg Gly Arg Lys Thr Asp Thr Phe Phe Lys Val
            20                  25                  30

Phe Gln Val Ala Pro Asn Ile Trp Ile Ala Pro Glu Arg Tyr Tyr Gly
        35                  40                  45

Glu Ser Leu Asn Ile Asn Glu Asp Gln Lys Ser Asp Gly Gly Ile Tyr
    50                  55                  60

Asp Ser Asn Phe Leu Ser Thr Asn Asp Glu Lys Asp Glu Phe Leu Gln
65                  70                  75                  80
```

-continued

```
Ala Thr Val Lys Ile Leu Gln Arg Ile Asn Asn Val Ile Gly Ala
                 85                  90                  95
Lys Leu Leu Ser Leu Ile Ser Thr Ala Ile Pro Phe Pro Tyr Glu Tyr
            100                 105                 110
Lys Pro Gly Asp Tyr Arg Gln Thr Asn Tyr Leu Val Ser Lys Asp Asn
        115                 120                 125
Gln His Tyr Tyr Thr Ala Asn Leu Val Ile Phe Gly Pro Gly Thr Asn
    130                 135                 140
Ile Val Glu Asn Asn Ala Ile Tyr Tyr Lys Glu Asp Ser Glu Asn
145                 150                 155                 160
Gly Met Gly Thr Met Ser Glu Ile Trp Phe Gln Pro Phe Leu Thr Tyr
                165                 170                 175
Lys Tyr Gly Gln Phe Tyr Val Asp Pro Ala Leu Glu Leu Ile Lys Cys
            180                 185                 190
Leu Ile Lys Ser Leu Tyr Tyr Leu Tyr Gly Ile Lys Pro Ser Asp Asp
        195                 200                 205
Leu Ser Ile Pro Tyr Arg Leu Arg Ser Glu Leu Asn Ser Phe Glu Tyr
    210                 215                 220
Ser Glu Leu Asp Met Ile Asp Phe Leu Ile Ser Gly Gly Thr Glu Tyr
225                 230                 235                 240
Lys Leu Leu Asp Thr Asn Pro Tyr Trp Phe Thr Asp Asn Tyr Phe Ile
                245                 250                 255
Asp Ala Pro Lys Asn Phe Glu Lys Tyr Lys Asn Asp Tyr Glu Thr Lys
            260                 265                 270
Ile Lys Asn Asn Asp Ile Ala Asn Ser Ile Lys Leu Tyr Leu Glu
        275                 280                 285
Gln Lys Phe Lys Thr Asn Ala Gln Asp Ile Trp Glu Leu Asn Leu Ser
    290                 295                 300
Tyr Phe Ser Thr Glu Phe Glu Ile Met Met Pro Glu Ile Phe Asn Asn
305                 310                 315                 320
Ala Leu Asn His Tyr Tyr Arg Lys Glu Tyr Tyr Val Ile Asp Tyr Phe
                325                 330                 335
Lys Asn Tyr Asn Ile Asn Gly Phe Ile Asn Gly Gln Ile Lys Thr Ile
            340                 345                 350
Leu Pro Leu Ser Lys Tyr Asn Lys Asn Ile Ile Asn Lys Pro Glu Leu
        355                 360                 365
Val Val Asn Leu Ile Asn Glu Asn Asn Thr Val Leu Met Lys Ser Asn
    370                 375                 380
Val Tyr Gly Asp Gly Leu Lys Gly Thr Met Asp Asn Phe Tyr Ala Ala
385                 390                 395                 400
Tyr Lys Ile Pro Tyr Asn Ile Gly Asp Glu Tyr His Ile Asn Tyr Ser
                405                 410                 415
Tyr Leu Asn Asn Val Asn Val Glu Glu Ile Asn Asn Ile Pro Pro Ile
            420                 425                 430
Asn Asp Ala Asp Ile Tyr Pro Tyr Arg Lys Asn Ser Asp Pro Phe Ile
        435                 440                 445
Pro Val Tyr Asn Ile Thr Glu Thr Lys Glu Ile Asn Thr Thr Thr Pro
    450                 455                 460
Leu Ser Val Asn Tyr Leu Gln Ala Gln Val Thr Asn Ser Asn Asp Ile
465                 470                 475                 480
Ser Leu Ser Ser Asp Phe Ser Lys Val Ile Ser Ser Lys Asp Arg Ser
                485                 490                 495
Leu Val Tyr Ser Phe Leu Asp Asn Thr Ile Asp Tyr Leu Asp Ser Ile
```

-continued

```
            500                 505                 510
Lys Tyr Asp Glu Pro Ile Asp Thr Asp Lys Tyr Tyr Leu Trp Leu
            515                 520                 525
Lys Glu Ile Phe Arg Asn Tyr Ser Phe Asp Met Thr Glu Thr Gln Glu
        530                 535                 540
Val Asn Thr Pro Cys Gly Ile Asn Lys Val Val Pro Trp Leu Gly Lys
545                 550                 555                 560
Ala Leu Asn Ile Leu Asn Thr Gly Asn Ser Phe Ile Glu Glu Phe Lys
                565                 570                 575
Ser Leu Gly Pro Ile Ser Leu Ile Asn Lys Lys Glu Asn Ile Thr Met
            580                 585                 590
Pro Lys Ile Glu Ile Asp Glu Ile Pro Asn Ser Met Leu Asn Leu Ser
        595                 600                 605
Phe Lys Asp Leu Ser Glu Asn Leu Phe Asn Arg Phe Ser Lys Asn Asn
    610                 615                 620
Ser Tyr Phe Glu Lys Ile Tyr Tyr Asp Phe Leu Asp Gln Trp Trp Thr
625                 630                 635                 640
Gln Tyr Tyr Ser Gln Tyr Phe Asp Leu Ile Cys Met Ala Lys Lys Ser
                645                 650                 655
Ile Leu Ala Gln Glu Thr Leu Ile Lys Lys Ile Gln Lys Lys Leu
            660                 665                 670
Ser Tyr Leu Ile Gly Asn Ser Asn Ile Ser Ser Asp Asn Leu Ala Leu
        675                 680                 685
Met Asn Leu Thr Thr Thr Asn Thr Leu Arg Asp Ile Ser Asn Glu Ser
    690                 695                 700
Gln Ile Ala Met Asn Asn Val Asp Ser Phe Leu Asn Ser Ala Ala Ile
705                 710                 715                 720
Cys Val Phe Glu Gly Asn Ile Tyr Ser Lys Phe Ile Ser Phe Met Glu
                725                 730                 735
Gln Cys Ile Asn Asn Ile Asn Lys Asn Thr Arg Glu Phe Ile Gln Lys
            740                 745                 750
Cys Thr Asn Ile Thr Glu Asn Glu Lys Leu Gln Leu Ile Asn Gln Asn
        755                 760                 765
Ile Phe Ser Ser Leu Asp Phe Asp Phe Leu Asn Ile Glu Asn Leu Lys
    770                 775                 780
Ser Leu Phe Ser Ser Glu Thr Ala Leu Leu Ile Lys Glu Glu Thr Ser
785                 790                 795                 800
Pro Tyr Glu Leu Val Leu Tyr Ala Phe Gln Glu Pro Asp Asn Asn Ala
                805                 810                 815
Ile Gly Asp Ala Ser Ala Lys Asn Thr Ser Ile Glu Tyr Ser Lys Asp
            820                 825                 830
Ile Asp Leu Val Tyr Gly Ile Asn Ser Asp Ala Leu Tyr Leu Asn Gly
        835                 840                 845
Ser Asn Gln Ser Ile Ser Phe Ser Asn Asp Phe Phe Glu Asn Gly Leu
    850                 855                 860
Thr Asn Ser Phe Ser Ile Tyr Phe Trp Leu Arg Asn Leu Gly Lys Asp
865                 870                 875                 880
Thr Ile Lys Ser Lys Leu Ile Gly Ser Lys Glu Asp Asn Cys Gly Trp
                885                 890                 895
Glu Ile Tyr Phe Gln Asp Thr Gly Leu Val Phe Asn Met Ile Asp Ser
            900                 905                 910
Asn Gly Asn Glu Lys Asn Ile Tyr Leu Ser Asp Val Ser Asn Asn Ser
        915                 920                 925
```

Trp His Tyr Ile Thr Ile Ser Val Asp Arg Leu Lys Glu Gln Leu Leu
                930                 935                 940

Ile Phe Ile Asp Asp Asn Leu Val Ala Asn Glu Ser Ile Lys Glu Ile
945                 950                 955                 960

Leu Asn Ile Tyr Ser Ser Asn Ile Ile Ser Leu Leu Ser Glu Asn Asn
                965                 970                 975

Pro Ser Tyr Ile Glu Gly Leu Thr Ile Leu Asn Lys Pro Thr Thr Ser
                980                 985                 990

Gln Glu Val Leu Asn Asn Tyr Phe Lys Val Leu Asn Asn Ser Tyr Ile
            995                 1000                1005

Arg Asp Ser Asn Glu Glu Arg Leu Glu Tyr Asn Lys Thr Tyr Gln
        1010                1015                1020

Leu Tyr Asn Tyr Val Phe Ser Asp Lys Pro Ile Cys Glu Val Lys
        1025                1030                1035

Gln Asn Asn Asn Ile Tyr Leu Thr Ile Asn Asn Thr Asn Asn Leu
        1040                1045                1050

Asn Leu Gln Pro Ser Lys Phe Lys Leu Leu Ser Ile Asn Ser Asn
        1055                1060                1065

Lys Gln Tyr Val Gln Lys Phe Asp Glu Val Ile Ile Ser Ile Leu
        1070                1075                1080

Gly Asn Met Glu Lys Tyr Ile Asp Ile Ser Glu Asp Asn Arg Leu
        1085                1090                1095

Gln Leu Ile Asp Asn Lys Asn Gly Ala Lys Lys Met Ile Ile Ser
        1100                1105                1110

Asn Asp Met Phe Ile Ser Asn Cys Leu Thr Leu Ser Cys Gly Gly
        1115                1120                1125

Lys Tyr Ile Cys Leu Ser Met Lys Asp Glu Asn His Asn Trp Met
        1130                1135                1140

Ile Cys Asn Asn Asp Met Ser Lys Tyr Leu Tyr Leu Trp Ser Phe
        1145                1150                1155

Lys

<210> SEQ ID NO 24
<211> LENGTH: 1197
<212> TYPE: PRT
<213> ORGANISM: Clostridium botulinum

<400> SEQUENCE: 24

Met Asn Ile Asn Asp Asn Leu Ser Ile Asn Ser Pro Val Asp Asn Lys
1               5                   10                  15

Asn Val Val Val Arg Ala Arg Lys Thr Asp Thr Val Phe Lys Ala
                20                  25                  30

Phe Lys Val Ala Pro Asn Ile Trp Val Ala Pro Glu Arg Tyr Tyr Gly
            35                  40                  45

Glu Ser Leu Ser Ile Asp Glu Glu Tyr Lys Val Asp Gly Gly Ile Tyr
        50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

```
Pro Lys Ser Asn Lys Lys Leu Asn Ser Leu Ile Ser Thr Ile Pro
    130                 135                 140

Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Thr Glu Ile Trp Phe Gln Pro Phe Leu Thr
        195                 200                 205

Tyr Lys Tyr Asp Glu Phe Tyr Ile Asp Pro Ala Ile Glu Leu Ile Lys
    210                 215                 220

Cys Leu Ile Lys Ser Leu Tyr Phe Leu Tyr Gly Ile Lys Pro Ser Asp
225                 230                 235                 240

Asp Leu Val Ile Pro Tyr Arg Leu Arg Ser Glu Leu Glu Asn Ile Glu
                245                 250                 255

Tyr Ser Gln Leu Asn Ile Val Asp Leu Leu Val Ser Gly Gly Ile Asp
            260                 265                 270

Pro Lys Phe Ile Asn Thr Asp Pro Tyr Trp Phe Thr Asp Asn Tyr Phe
        275                 280                 285

Ser Asn Ala Lys Lys Val Phe Glu Asp His Arg Asn Ile Tyr Glu Thr
290                 295                 300

Gln Ile Glu Gly Asn Asn Ala Ile Gly Asn Asp Ile Lys Leu Arg Leu
305                 310                 315                 320

Lys Gln Lys Phe Arg Ile Asn Ile Asn Asp Ile Trp Glu Leu Asn Leu
                325                 330                 335

Asn Tyr Phe Ser Lys Glu Phe Ser Ile Met Met Pro Asp Arg Phe Asn
            340                 345                 350

Asn Ala Leu Lys His Phe Tyr Arg Lys Gln Tyr Tyr Lys Ile Asp Tyr
        355                 360                 365

Pro Glu Asn Tyr Ser Ile Asn Gly Phe Val Asn Gly Gln Ile Asn Val
370                 375                 380

Gln Leu Ser Leu Ser Asp Arg Asn Gln Asp Ile Ile Asn Lys Pro Glu
385                 390                 395                 400

Glu Ile Ile Asn Leu Leu Asn Gly Asn Asn Val Ser Leu Met Arg Ser
                405                 410                 415

Asn Ile Tyr Gly Asp Gly Leu Lys Ser Thr Val Asp Asp Phe Tyr Ser
            420                 425                 430

Asn Tyr Lys Ile Pro Tyr Asn Arg Ala Tyr Glu Tyr His Phe Asn Asn
        435                 440                 445

Ser Asn Asp Ser Ser Leu Asp Asn Val Asn Ile Gly Val Ile Asp Asn
450                 455                 460

Ile Pro Glu Ile Ile Asp Val Asn Pro Tyr Lys Glu Asn Cys Asp Lys
465                 470                 475                 480

Phe Ser Pro Val Gln Lys Ile Thr Ser Thr Arg Glu Ile Asn Thr Asn
                485                 490                 495

Ile Pro Trp Pro Ile Asn Tyr Leu Gln Ala Gln Asn Thr Asn Asn Glu
            500                 505                 510

Lys Phe Ser Leu Ser Ser Asp Phe Val Glu Val Ser Ser Lys Asp
        515                 520                 525

Lys Ser Leu Val Tyr Ser Phe Leu Ser Asn Val Met Phe Tyr Leu Asp
530                 535                 540
```

```
Ser Ile Lys Asp Asn Ser Pro Ile Asp Thr Asp Lys Lys Tyr Tyr Leu
545                 550                 555                 560

Trp Leu Arg Glu Ile Phe Arg Asn Tyr Ser Phe Asp Ile Thr Ala Thr
                565                 570                 575

Gln Glu Ile Asn Thr Asp Cys Gly Ile Asn Lys Val Val Thr Trp Phe
            580                 585                 590

Gly Lys Ala Leu Asn Ile Leu Asn Thr Ser Asp Ser Phe Val Glu Glu
        595                 600                 605

Phe Gln Asn Leu Gly Pro Ile Ser Leu Ile Asn Lys Lys Glu Asn Leu
    610                 615                 620

Ser Met Pro Ile Ile Glu Ile Tyr Gly Ile Pro Asn Asp Met Leu Gly
625                 630                 635                 640

Leu Pro Leu Asn Asp Leu Asn Glu Lys Leu Phe Asn Ile Tyr Leu Lys
                645                 650                 655

Asn Ile Leu Tyr Phe Lys Lys Val Tyr Phe Asn Phe Leu Asp Gln Trp
            660                 665                 670

Trp Thr Glu Tyr Tyr Ser Gln Tyr Phe Asp Leu Ile Cys Met Ala Lys
        675                 680                 685

Gln Ser Ile Leu Ala Gln Glu Lys Leu Ile Lys Gln Ile Ile Gln Asn
    690                 695                 700

Lys Leu Gln Asp Leu Phe Lys Ala Asp Ile Ser Met Asp Lys Leu Asn
705                 710                 715                 720

Leu Met Asn Leu Ala Thr Glu Lys Thr Phe Ile Asp Leu Ser Asn Glu
                725                 730                 735

Ser Gln Ile Ala Ile Asn Asn Ile Asn Asp Phe Leu Asn Lys Ser Ala
            740                 745                 750

Ile Cys Val Phe Asp Thr Asn Ile Tyr Pro Lys Phe Ile Ser Phe Met
        755                 760                 765

Glu Gln Cys Ile Asn Ser Val Asn Ser Asn Val Thr Ala Phe Ile Gln
    770                 775                 780

Lys Cys Thr Asn Ile Thr Glu Asp Glu Lys Leu Gln Leu Ile Lys Leu
785                 790                 795                 800

Asn Thr Phe Met Asn Ile Asp Phe Glu Phe Phe Asp Ile Gln Ser Ile
                805                 810                 815

Lys Asp Leu Ile Thr Ser Glu Thr Asp Leu Ile Lys Glu Glu Lys Glu
            820                 825                 830

Ser Asp Tyr Asn Leu Phe Leu Phe Thr Leu Gln Glu Asp Asn Asn Lys
        835                 840                 845

Val Ile Glu Asp Ile Ser Gly Lys Asn Thr Leu Val Lys Tyr Ser Asp
850                 855                 860

Ser Ile Ser Leu Val Tyr Gly Val Asn Gly Asp Ala Leu Tyr Leu Lys
865                 870                 875                 880

Glu Pro Asp Glu Ser Val Ser Phe Ser Asn Lys Ala Phe Glu Asn Gly
                885                 890                 895

Leu Thr Asn Ser Phe Ser Ile Cys Phe Trp Leu Arg Asn Leu Gly Glu
            900                 905                 910

Asp Ile Ile Thr Ser Lys Leu Ile Glu Asn Lys Ala Asp Asn Cys Gly
        915                 920                 925

Trp Glu Ile Tyr Phe Glu Asn Asn Gly Leu Val Phe Ser Ile Val Asp
    930                 935                 940

Cys Asn Gly Asn Glu Glu Asn Ile Tyr Leu Ser Asp Val Ile Ser Lys
945                 950                 955                 960

Asn Trp Tyr Tyr Ile Ser Ile Ser Ile Asp Arg Leu Arg Asn Gln Leu
```

-continued

```
            965                 970                 975
Leu Ile Phe Ile Asn Asp Lys Leu Ile Ala Asn Gln Ser Ile Glu Gln
            980                 985                 990
Ile Leu Asn Ile Tyr Ser Ser Asn  Thr Ile Ser Leu Val  Asn Glu Asn
            995                 1000                1005
Asn Pro  Ile Tyr Ile Glu Gly  Leu Ser Ile Leu Asn  Arg Ser Ile
   1010                 1015                1020
Thr Ser  Glu Glu Val Val Asn  Asn Tyr Phe Ser Tyr  Leu Asn Asn
   1025                 1030                1035
Ser Tyr  Ile Arg Asp Ile Ser  Gly Glu Arg Leu Glu  Tyr Asn Lys
   1040                 1045                1050
Thr Tyr  Glu Leu Tyr Asn Tyr  Val Phe Pro Glu Asn  Ser Leu Tyr
   1055                 1060                1065
Glu Val  Thr Glu Asn Asn Asn  Ile Tyr Leu Ser Ile  Lys Asp Thr
   1070                 1075                1080
Asn Asn  Leu Asn Ile Gln Gly  Ala Lys Phe Lys Leu  Ile Asn Ile
   1085                 1090                1095
Asp Ala  Asn Lys Gln Tyr Val  Gln Lys Trp Asp Glu  Gly Val Val
   1100                 1105                1110
Cys Leu  Leu Gly Asp Glu Glu  Lys Tyr Val Asp Ile  Ser Ser Glu
   1115                 1120                1125
Asn Asn  Arg Ile Gln Leu Val  Asn Ser Lys Asp Thr  Ala Lys Arg
   1130                 1135                1140
Ile Ile  Phe Asn Asn Asp Ile  Phe Met Pro Asn Cys  Leu Thr Phe
   1145                 1150                1155
Ala Tyr  Asn Asn Lys Tyr Leu  Ser Leu Ser Leu Arg  Asp Arg Asn
   1160                 1165                1170
Tyr Asn  Trp Met Ile Cys Asn  Asn Asp Asn Ile Pro  Lys Ala
   1175                 1180                1185
Ala His  Leu Trp Ala Leu Lys  Gly Ile
   1190                 1195

<210> SEQ ID NO 25
<211> LENGTH: 1196
<212> TYPE: PRT
<213> ORGANISM: Clostridium phage c-st

<400> SEQUENCE: 25

Met Asp Ile Asn Asp Asp Leu Asn Ile Asn Ser Pro Val Asp Asn Lys
1               5                   10                  15
Asn Val Val Ile Val Arg Ala Arg Lys Thr Asn Thr Phe Phe Lys Ala
                20                  25                  30
Phe Lys Val Ala Pro Asn Ile Trp Val Ala Pro Glu Arg Tyr Tyr Gly
            35                  40                  45
Glu Pro Leu Asp Ile Ala Glu Glu Tyr Lys Leu Asp Gly Gly Ile Tyr
        50                  55                  60
Asp Ser Asn Phe Leu Ser Gln Asp Ser Glu Arg Glu Asn Phe Leu Gln
65                  70                  75                  80
Ala Ile Ile Ile Leu Leu Lys Arg Ile Asn Asn Thr Ile Ser Gly Lys
                85                  90                  95
Gln Leu Leu Ser Leu Ile Ser Thr Ala Ile Pro Phe Pro Tyr Gly Tyr
            100                 105                 110
Ile Gly Gly Gly Tyr Ser Ser Pro Asn Ile Phe Thr Phe Gly Lys Thr
        115                 120                 125
```

-continued

```
Pro Lys Ser Asn Lys Lys Leu Asn Ser Leu Val Thr Ser Thr Ile Pro
    130                 135                 140
Phe Pro Phe Gly Gly Tyr Arg Glu Thr Asn Tyr Ile Glu Ser Gln Asn
145                 150                 155                 160
Asn Lys Asn Phe Tyr Ala Ser Asn Ile Ile Phe Gly Pro Gly Ser
                165                 170                 175
Asn Ile Val Glu Asn Asn Val Ile Tyr Tyr Lys Lys Asn Asp Ala Glu
            180                 185                 190
Asn Gly Met Gly Thr Met Ala Glu Ile Val Phe Gln Pro Leu Leu Thr
        195                 200                 205
Tyr Lys Tyr Asn Lys Phe Tyr Ile Asp Pro Ala Met Glu Leu Thr Lys
    210                 215                 220
Cys Leu Ile Lys Ser Leu Tyr Phe Leu Tyr Gly Ile Lys Pro Ser Asp
225                 230                 235                 240
Asn Leu Val Val Pro Tyr Arg Leu Arg Thr Glu Leu Asp Asn Lys Gln
                245                 250                 255
Phe Ser Gln Leu Asn Ile Ile Asp Leu Leu Ile Ser Gly Gly Val Asp
            260                 265                 270
Leu Glu Phe Ile Asn Thr Asn Pro Tyr Trp Phe Thr Asn Ser Tyr Phe
        275                 280                 285
Pro Asn Ser Ile Lys Met Phe Glu Lys Tyr Lys Asn Ile Tyr Lys Thr
    290                 295                 300
Glu Ile Glu Gly Asn Asn Ala Ile Gly Asn Asp Ile Lys Leu Arg Leu
305                 310                 315                 320
Lys Gln Lys Phe Gln Ile Asn Val Gln Asp Ile Trp Asn Leu Asn Leu
                325                 330                 335
Asn Tyr Phe Cys Gln Ser Phe Asn Ser Ile Ile Pro Asp Arg Phe Ser
            340                 345                 350
Asn Ala Leu Lys His Phe Tyr Arg Lys Gln Tyr Tyr Thr Met Asp Tyr
        355                 360                 365
Thr Asp Asn Tyr Asn Ile Asn Gly Phe Val Asn Gly Gln Ile Asn Thr
    370                 375                 380
Lys Leu Pro Leu Ser Asn Lys Asn Thr Asn Ile Ile Ser Lys Pro Glu
385                 390                 395                 400
Lys Val Val Asn Leu Val Asn Glu Asn Asn Ile Ser Leu Met Lys Ser
                405                 410                 415
Asn Ile Tyr Gly Asp Gly Leu Lys Gly Thr Thr Glu Asp Phe Tyr Ser
            420                 425                 430
Thr Tyr Lys Ile Pro Tyr Asn Glu Glu Tyr Glu Tyr Arg Phe Asn Asp
        435                 440                 445
Ser Asp Asn Phe Pro Leu Asn Asn Ile Ser Ile Glu Glu Val Asp Ser
    450                 455                 460
Ile Pro Glu Ile Ile Asp Ile Asn Pro Tyr Lys Asp Asn Ser Asp Asn
465                 470                 475                 480
Leu Val Phe Thr Gln Ile Thr Ser Met Thr Glu Glu Val Thr Thr His
                485                 490                 495
Thr Ala Leu Ser Ile Asn Tyr Leu Gln Ala Gln Ile Thr Asn Asn Glu
            500                 505                 510
Asn Phe Thr Leu Ser Ser Asp Phe Ser Lys Val Val Ser Ser Lys Asp
        515                 520                 525
Lys Ser Leu Val Tyr Ser Phe Leu Asp Asn Leu Met Ser Tyr Leu Glu
    530                 535                 540
Thr Ile Lys Asn Asp Gly Pro Ile Asp Thr Asp Lys Lys Tyr Tyr Leu
```

```
                545                 550                 555                 560
         Trp Leu Lys Glu Val Phe Lys Asn Tyr Ser Phe Asp Ile Asn Leu Thr
                         565                 570                 575
         Gln Glu Ile Asp Ser Met Cys Gly Ile Asn Glu Val Val Leu Trp Phe
                         580                 585                 590
         Gly Lys Ala Leu Asn Ile Leu Asn Thr Ser Asn Ser Phe Val Glu Glu
                         595                 600                 605
         Tyr Gln Asp Ser Gly Ala Ile Ser Leu Ile Ser Lys Lys Asp Asn Leu
                         610                 615                 620
         Arg Glu Pro Asn Ile Glu Ile Asp Asp Ile Ser Asp Ser Leu Leu Gly
         625                 630                 635                 640
         Leu Ser Phe Lys Asp Leu Asn Asn Lys Leu Tyr Glu Ile Tyr Ser Lys
                         645                 650                 655
         Asn Ile Val Tyr Phe Lys Lys Ile Tyr Phe Ser Phe Leu Asp Gln Trp
                         660                 665                 670
         Trp Thr Glu Tyr Tyr Ser Gln Tyr Phe Glu Leu Ile Cys Met Ala Lys
                         675                 680                 685
         Gln Ser Ile Leu Ala Gln Glu Ser Leu Val Lys Gln Ile Val Gln Asn
                         690                 695                 700
         Lys Phe Thr Asp Leu Ser Lys Ala Ser Ile Pro Pro Asp Thr Leu Lys
         705                 710                 715                 720
         Leu Ile Arg Glu Thr Thr Glu Lys Thr Phe Ile Asp Leu Ser Asn Glu
                         725                 730                 735
         Ser Gln Ile Ser Met Asn Arg Val Asp Asn Phe Leu Asn Lys Ala Ser
                         740                 745                 750
         Ile Cys Val Phe Val Glu Asp Ile Tyr Pro Lys Phe Ile Ser Tyr Met
                         755                 760                 765
         Glu Lys Tyr Ile Asn Asn Ile Asn Ile Lys Thr Arg Glu Phe Ile Gln
                         770                 775                 780
         Arg Cys Thr Asn Ile Asn Asp Asn Glu Lys Ser Ile Leu Ile Asn Ser
         785                 790                 795                 800
         Tyr Thr Phe Lys Thr Ile Asp Phe Lys Phe Leu Asp Ile Gln Ser Ile
                         805                 810                 815
         Lys Asn Phe Phe Asn Ser Gln Val Glu Gln Val Met Lys Glu Ile Leu
                         820                 825                 830
         Ser Pro Tyr Gln Leu Leu Leu Phe Ala Ser Lys Gly Pro Asn Ser Asn
                         835                 840                 845
         Ile Ile Glu Asp Ile Ser Gly Lys Asn Thr Leu Ile Gln Tyr Thr Glu
         850                 855                 860
         Ser Ile Glu Leu Val Tyr Gly Val Asn Gly Glu Ser Leu Tyr Leu Lys
         865                 870                 875                 880
         Ser Pro Asn Glu Thr Ile Lys Phe Ser Asn Lys Phe Phe Thr Asn Gly
                         885                 890                 895
         Leu Thr Asn Asn Phe Thr Ile Cys Phe Trp Leu Arg Phe Thr Gly Lys
                         900                 905                 910
         Asn Asp Asp Lys Thr Arg Leu Ile Gly Asn Lys Val Asn Asn Cys Gly
                         915                 920                 925
         Trp Glu Ile Tyr Phe Glu Asp Asn Gly Leu Val Phe Glu Ile Ile Asp
                         930                 935                 940
         Ser Asn Gly Asn Gln Glu Ser Val Tyr Leu Ser Asn Ile Ile Asn Asp
         945                 950                 955                 960
         Asn Trp Tyr Tyr Ile Ser Ile Ser Val Asp Arg Leu Lys Asp Gln Leu
                         965                 970                 975
```

```
Leu Ile Phe Ile Asn Asp Lys Asn Val Ala Asn Val Ser Ile Asp Gln
                980             985                 990

Ile Leu Ser Ile Tyr Ser Thr Asn Ile Ile Ser Leu Val Asn Lys Asn
            995                 1000                1005

Asn Ser Ile Tyr Val Glu Glu Leu Ser Val Leu Asp Asn Pro Ile
        1010            1015                1020

Thr Ser Glu Glu Val Ile Arg Asn Tyr Phe Ser Tyr Leu Asp Asn
    1025            1030                1035

Ser Tyr Ile Arg Asp Ser Ser Lys Ser Leu Leu Glu Tyr Asn Lys
        1040            1045                1050

Asn Tyr Gln Leu Tyr Asn Tyr Val Phe Pro Glu Thr Ser Leu Tyr
    1055            1060                1065

Glu Val Asn Asp Asn Asn Lys Ser Tyr Leu Ser Leu Lys Asn Thr
    1070            1075                1080

Asp Gly Ile Asn Ile Ser Ser Val Lys Phe Lys Leu Ile Asn Ile
    1085            1090                1095

Asp Glu Ser Lys Val Tyr Val Gln Lys Trp Asp Glu Cys Ile Ile
    1100            1105                1110

Cys Val Leu Asp Gly Thr Glu Lys Tyr Leu Asp Ile Ser Pro Glu
    1115            1120                1125

Asn Asn Arg Ile Gln Leu Val Ser Ser Lys Asp Asn Ala Lys Lys
    1130            1135                1140

Ile Thr Val Asn Thr Asp Leu Phe Arg Pro Asp Cys Ile Thr Phe
    1145            1150                1155

Ser Tyr Asn Asp Lys Tyr Phe Ser Leu Ser Leu Arg Asp Gly Asp
    1160            1165                1170

Tyr Asn Trp Met Ile Cys Asn Asp Asn Lys Val Pro Lys Gly
    1175            1180                1185

Ala His Leu Trp Ile Leu Glu Ser
    1190            1195

<210> SEQ ID NO 26
<211> LENGTH: 1196
<212> TYPE: PRT
<213> ORGANISM: Clostridium botulinum D phage

<400> SEQUENCE: 26

Met Asp Ile Asn Asp Asp Leu Asn Ile Asn Ser Pro Val Asp Asn Lys
1               5                   10                  15

Asn Val Val Ile Val Arg Ala Arg Lys Thr Asn Thr Phe Phe Lys Ala
                20                  25                  30

Phe Lys Val Ala Pro Asn Ile Trp Val Ala Pro Glu Arg Tyr Tyr Gly
            35                  40                  45

Glu Pro Leu Asp Ile Ala Glu Glu Tyr Lys Leu Asp Gly Gly Ile Tyr
        50                  55                  60

Asp Ser Asn Phe Leu Ser Gln Asp Ser Glu Arg Glu Asn Phe Leu Gln
65                  70                  75                  80

Ala Ile Ile Ile Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
                100                 105                 110

Ile Gly Gly Gly Tyr Ser Ser Pro Asn Ile Phe Thr Phe Gly Lys Thr
            115                 120                 125

Pro Lys Ser Asn Lys Lys Leu Asn Ser Leu Val Thr Ser Thr Ile Pro
```

```
                130             135             140
        Phe Pro Phe Gly Gly Tyr Arg Glu Thr Asn Tyr Ile Glu Ser Gln Asn
        145                 150                 155                 160

Asn Lys Asn Phe Tyr Ala Ser Asn Ile Val Ile Phe Gly Pro Gly Ser
                        165                 170                 175

Asn Ile Val Glu Asn Asn Val Ile Tyr Lys Lys Asn Asp Ala Glu
                    180                 185                 190

Asn Gly Met Gly Thr Met Ala Glu Ile Val Phe Gln Pro Leu Leu Thr
                    195                 200                 205

Tyr Lys Tyr Asn Lys Phe Tyr Ile Asp Pro Ala Met Glu Leu Thr Lys
                210                 215                 220

Cys Leu Ile Lys Ser Leu Tyr Phe Leu Tyr Gly Ile Lys Pro Ser Asp
        225                 230                 235                 240

Asn Leu Val Val Pro Tyr Arg Leu Arg Thr Glu Leu Asp Asn Lys Gln
                        245                 250                 255

Phe Ser Gln Leu Asn Ile Ile Asp Leu Leu Ile Ser Gly Gly Val Asp
                    260                 265                 270

Leu Glu Phe Ile Asn Thr Asn Pro Tyr Trp Phe Thr Asn Ser Tyr Phe
                275                 280                 285

Pro Asn Ser Ile Lys Met Phe Glu Lys Tyr Lys Asn Ile Tyr Lys Thr
        290                 295                 300

Glu Ile Glu Gly Asn Asn Ala Ile Gly Asn Asp Ile Lys Leu Arg Leu
        305                 310                 315                 320

Lys Gln Lys Phe Gln Ile Asn Val Gln Asp Ile Trp Asn Leu Asn Leu
                        325                 330                 335

Asn Tyr Phe Cys Gln Ser Phe Asn Ser Ile Ile Pro Asp Arg Phe Ser
                    340                 345                 350

Asn Ala Leu Lys His Phe Tyr Arg Lys Gln Tyr Tyr Thr Met Asp Tyr
                    355                 360                 365

Thr Asp Asn Tyr Asn Ile Asn Gly Phe Val Asn Gly Gln Ile Asn Thr
                370                 375                 380

Lys Leu Pro Leu Ser Asn Lys Asn Thr Asn Ile Ile Ser Lys Pro Glu
        385                 390                 395                 400

Lys Val Val Asn Leu Val Asn Glu Asn Asn Ile Ser Leu Met Lys Ser
                        405                 410                 415

Asn Ile Tyr Gly Asp Gly Leu Lys Gly Ser Thr Glu Asp Phe Tyr Ser
                    420                 425                 430

Thr Tyr Lys Ile Pro Tyr Asn Glu Glu Tyr Glu Tyr Arg Phe Asn Asp
                435                 440                 445

Ser Asp Asn Phe Pro Leu Asn Asn Ile Ser Glu Glu Val Asp Ser
            450                 455                 460

Ile Pro Glu Ile Ile Asp Ile Asn Pro Tyr Lys Asp Asn Ser Asp Asn
        465                 470                 475                 480

Leu Val Phe Thr Gln Ile Thr Ser Met Thr Glu Glu Val Thr Thr His
                        485                 490                 495

Thr Ala Leu Ser Ile Asn Tyr Leu Gln Ala Gln Ile Thr Asn Asn Glu
                    500                 505                 510

Asn Phe Thr Leu Ser Ser Asp Phe Ser Lys Val Val Ser Ser Lys Asp
                515                 520                 525

Lys Ser Leu Val Tyr Ser Phe Leu Asp Asn Leu Met Ser Tyr Leu Glu
                530                 535                 540

Thr Ile Lys Asn Asp Gly Pro Ile Asp Thr Asp Lys Lys Tyr Tyr Leu
        545                 550                 555                 560
```

-continued

Trp Leu Lys Glu Val Phe Lys Asn Tyr Ser Phe Asp Ile Asn Leu Thr
                565                 570                 575

Gln Glu Ile Asp Ser Met Cys Gly Ile Asn Glu Val Val Leu Trp Phe
                580                 585                 590

Gly Lys Ala Leu Asn Ile Leu Asn Thr Ser Asn Ser Phe Val Glu Glu
                595                 600                 605

Tyr Gln Asp Ser Gly Ala Ile Ser Leu Ile Ser Lys Lys Asp Asn Leu
                610                 615                 620

Arg Glu Pro Asn Ile Glu Ile Asp Asp Ile Ser Asp Ser Leu Leu Gly
625                 630                 635                 640

Leu Ser Phe Lys Asp Leu Asn Asn Lys Leu Tyr Glu Ile Tyr Ser Lys
                645                 650                 655

Asn Ile Val Tyr Phe Lys Lys Ile Tyr Phe Ser Phe Leu Asp Gln Trp
                660                 665                 670

Trp Thr Glu Tyr Tyr Ser Gln Tyr Phe Glu Leu Ile Cys Met Ala Lys
                675                 680                 685

Gln Ser Ile Leu Ala Gln Glu Ser Leu Val Lys Gln Ile Val Gln Asn
                690                 695                 700

Lys Phe Thr Asp Leu Ser Lys Ala Ser Ile Pro Pro Asp Thr Leu Lys
705                 710                 715                 720

Leu Ile Arg Glu Thr Thr Glu Lys Thr Phe Ile Asp Leu Ser Asn Glu
                725                 730                 735

Ser Gln Ile Ser Met Asn Arg Val Asp Asn Phe Leu Asn Lys Ala Ser
                740                 745                 750

Ile Cys Val Phe Val Glu Asp Ile Tyr Pro Lys Phe Ile Ser Tyr Met
                755                 760                 765

Glu Lys Tyr Ile Asn Asn Ile Asn Ile Lys Thr Arg Glu Phe Ile Gln
                770                 775                 780

Arg Cys Thr Asn Ile Asn Asp Asn Glu Lys Ser Ile Leu Ile Asn Ser
785                 790                 795                 800

Tyr Thr Phe Lys Thr Ile Asp Phe Lys Phe Leu Asp Ile Gln Ser Ile
                805                 810                 815

Lys Asn Phe Phe Asn Ser Gln Val Glu Gln Val Met Lys Glu Ile Leu
                820                 825                 830

Ser Pro Tyr Gln Leu Leu Phe Ala Ser Lys Gly Pro Asn Ser Asn
                835                 840                 845

Ile Ile Glu Asp Ile Ser Gly Lys Asn Thr Leu Ile Gln Tyr Thr Glu
                850                 855                 860

Ser Ile Glu Leu Val Tyr Gly Val Asn Gly Glu Ser Leu Tyr Leu Lys
865                 870                 875                 880

Ser Pro Asn Glu Thr Ile Lys Phe Ser Asn Lys Phe Phe Thr Asn Gly
                885                 890                 895

Leu Thr Asn Asn Phe Thr Ile Cys Phe Trp Leu Arg Phe Thr Gly Lys
                900                 905                 910

Asn Asp Asp Lys Thr Arg Leu Ile Gly Asn Lys Val Asn Asn Cys Gly
                915                 920                 925

Trp Glu Ile Tyr Phe Glu Asp Asn Gly Leu Val Phe Glu Ile Ile Asp
                930                 935                 940

Ser Asn Gly Asn Gln Glu Ser Val Tyr Leu Ser Asn Ile Ile Asn Asp
945                 950                 955                 960

Asn Trp Tyr Tyr Ile Ser Ile Ser Val Asp Arg Leu Lys Asp Gln Leu
                965                 970                 975

```
Leu Ile Phe Ile Asn Asp Lys Asn Val Ala Asn Val Ser Ile Asp Gln
            980                 985                 990

Ile Leu Ser Ile Tyr Ser Thr Asn Ile Ile Ser Leu Val Asn Lys Asn
            995                1000                1005

Asn Ser Ile Tyr Val Glu Glu Leu Ser Val Leu Asp Asn Pro Ile
        1010                1015                1020

Thr Ser Glu Glu Val Ile Arg Asn Tyr Phe Ser Tyr Leu Asp Asn
        1025                1030                1035

Ser Tyr Ile Arg Asp Ser Ser Lys Ser Leu Leu Glu Tyr Asn Lys
        1040                1045                1050

Asn Tyr Gln Leu Tyr Asn Tyr Val Phe Pro Glu Thr Ser Leu Tyr
        1055                1060                1065

Glu Val Asn Asp Asn Asn Lys Ser Tyr Leu Ser Leu Lys Asn Thr
        1070                1075                1080

Asp Gly Ile Asn Ile Ser Ser Val Lys Phe Lys Leu Ile Asn Ile
        1085                1090                1095

Asp Glu Ser Lys Gly Tyr Val Gln Lys Trp Asp Glu Cys Ile Ile
        1100                1105                1110

Cys Val Leu Asp Gly Thr Glu Lys Tyr Leu Asp Ile Ser Pro Glu
        1115                1120                1125

Asn Asn Arg Ile Gln Leu Val Ser Ser Lys Asp Asn Ala Lys Lys
        1130                1135                1140

Ile Thr Val Asn Thr Asp Leu Phe Arg Pro Asp Cys Ile Thr Phe
        1145                1150                1155

Ser Tyr Asn Asp Lys Tyr Phe Ser Leu Ser Leu Arg Asp Gly Asp
        1160                1165                1170

Tyr Asn Trp Met Ile Cys Asn Asp Asn Asn Lys Val Pro Lys Gly
        1175                1180                1185

Ala His Leu Trp Ile Leu Glu Ser
        1190                1195

<210> SEQ ID NO 27
<211> LENGTH: 1163
<212> TYPE: PRT
<213> ORGANISM: Clostridium butyricum

<400> SEQUENCE: 27

Met Lys Ile Asn Gly Asn Leu Asn Ile Asp Ser Pro Val Asp Asn Lys
1               5                   10                  15

Asn Val Ala Ile Val Arg Ser Arg Lys Ser Asp Val Phe Phe Lys Ala
            20                  25                  30

Phe Gln Val Ala Pro Asn Ile Trp Ile Ala Pro Glu Arg Tyr Tyr Gly
        35                  40                  45

Glu Ser Leu Lys Ile Asn Glu Asp Gln Lys Ser Asp Gly Gly Ile Tyr
    50                  55                  60

Asp Ser Asn Phe Leu Ser Thr Asn Asn Glu Lys Asp Glu Phe Leu Gln
65                  70                  75                  80

Ala Thr Ile Lys Leu Leu Gln Arg Ile Asn Asn Asn Val Val Gly Ala
                85                  90                  95

Lys Leu Leu Ser Leu Ile Ser Thr Ala Ile Pro Phe Tyr Glu Asn
            100                 105                 110

Asn Thr Glu Asp Tyr Arg Gln Thr Asn Tyr Leu Ser Ser Lys Asn Asn
        115                 120                 125

Glu His Tyr Tyr Thr Ala Asn Leu Val Ile Phe Gly Pro Gly Ser Asn
    130                 135                 140
```

```
Ile Ile Lys Asn Asn Val Ile Tyr Tyr Lys Lys Glu Tyr Ala Glu Asn
145                 150                 155                 160

Gly Met Gly Thr Met Leu Glu Ile Trp Phe Gln Pro Phe Leu Thr His
            165                 170                 175

Lys Tyr Asp Glu Phe Tyr Val Asp Pro Ala Leu Glu Leu Ile Lys Cys
        180                 185                 190

Leu Ile Lys Ser Leu Tyr Tyr Leu Tyr Gly Ile Lys Pro Asn Asp Asn
        195                 200                 205

Leu Asn Ile Pro Tyr Arg Leu Arg Asn Glu Phe Asn Ser Leu Glu Tyr
    210                 215                 220

Ser Glu Leu Asp Met Ile Asp Phe Leu Ile Ser Gly Gly Ile Asp Tyr
225                 230                 235                 240

Lys Leu Leu Asn Thr Asn Pro Tyr Trp Phe Ile Asp Lys Tyr Phe Ile
            245                 250                 255

Asp Thr Ser Lys Asn Phe Glu Lys Tyr Lys Asn Asp Tyr Glu Ile Lys
        260                 265                 270

Ile Lys Asn Asn Asn Tyr Ile Ala Asn Ser Ile Lys Leu Tyr Leu Glu
        275                 280                 285

Gln Lys Phe Lys Ile Asn Val Lys Asp Ile Trp Glu Leu Asn Leu Ser
290                 295                 300

Tyr Phe Ser Lys Glu Phe Gln Ile Met Met Pro Glu Arg Tyr Asn Asn
305                 310                 315                 320

Ala Leu Asn His Tyr Tyr Arg Lys Glu Tyr Tyr Val Ile Asp Tyr Phe
            325                 330                 335

Lys Asn Tyr Asn Ile Asn Gly Phe Lys Asn Gly Gln Ile Lys Thr Lys
        340                 345                 350

Leu Pro Leu Ser Lys Tyr Asn Lys Glu Ile Ile Asn Lys Pro Glu Leu
        355                 360                 365

Ile Val Asn Leu Ile Asn Gln Asn Asn Thr Val Leu Met Lys Ser Asn
    370                 375                 380

Ile Tyr Gly Asp Gly Leu Lys Gly Thr Val Asp Asn Phe Tyr Ser Asn
385                 390                 395                 400

Tyr Ile Ile Pro Tyr Asn Leu Asn Tyr Glu His Ser Ile Asn Tyr Ser
            405                 410                 415

Tyr Leu Asp Asn Val Asn Ile Glu Glu Ile Glu Lys Ile Pro Pro Ile
        420                 425                 430

Asn Asp Glu Asp Ile Tyr Pro Tyr Arg Lys Asn Ala Asp Thr Phe Ile
        435                 440                 445

Pro Val Tyr Asn Ile Thr Lys Ala Lys Glu Ile Asn Thr Thr Thr Pro
    450                 455                 460

Leu Pro Val Asn Tyr Leu Gln Ala Gln Met Ile Asp Ser Asn Asp Ile
465                 470                 475                 480

Asn Leu Ser Ser Asp Phe Leu Lys Val Ile Ser Ser Lys Gly Ser Leu
            485                 490                 495

Val Tyr Ser Phe Leu Asn Asn Thr Met Asp Tyr Leu Glu Phe Ile Lys
        500                 505                 510

Tyr Asp Lys Pro Ile Asp Thr Asp Lys Lys Tyr Tyr Lys Trp Leu Lys
        515                 520                 525

Ala Ile Phe Arg Asn Tyr Ser Leu Asp Ile Thr Glu Thr Gln Glu Ile
    530                 535                 540

Ser Asn Gln Phe Gly Asp Thr Lys Ile Ile Pro Trp Ile Gly Arg Ala
545                 550                 555                 560
```

```
Leu Asn Ile Leu Asn Thr Asn Ser Phe Val Glu Glu Phe Lys Asn
            565                 570                 575

Leu Gly Pro Ile Ser Leu Ile Asn Lys Lys Glu Asn Ile Thr Ile Pro
        580                 585                 590

Lys Ile Lys Ile Asp Glu Ile Pro Ser Ser Met Leu Asn Phe Ser Phe
        595                 600                 605

Lys Asp Leu Ser Glu Asn Leu Phe Asn Ile Tyr Cys Lys Asn Asn Phe
        610                 615                 620

Tyr Leu Lys Lys Ile Tyr Tyr Asn Phe Leu Asp Gln Trp Trp Thr Gln
625                 630                 635                 640

Tyr Tyr Ser Gln Tyr Phe Asp Leu Ile Cys Met Ala Ser Lys Ser Val
                645                 650                 655

Leu Ala Gln Glu Lys Leu Ile Lys Lys Leu Ile Gln Lys Gln Leu Arg
            660                 665                 670

Tyr Leu Met Glu Asn Ser Asn Ile Ser Ser Thr Asn Leu Ile Leu Ile
            675                 680                 685

Asn Leu Thr Thr Thr Asn Thr Leu Arg Asp Ile Ser Asn Gln Ser Gln
        690                 695                 700

Ile Ala Ile Asn Asn Ile Asp Lys Phe Phe Asn Asn Ala Ala Met Cys
705                 710                 715                 720

Val Phe Glu Asn Asn Ile Tyr Pro Lys Phe Thr Ser Phe Met Glu Gln
                725                 730                 735

Cys Ile Lys Asn Ile Asn Lys Ser Thr Lys Glu Phe Ile Leu Lys Cys
                740                 745                 750

Thr Asn Ile Asn Glu Thr Glu Lys Ser His Leu Ile Met Gln Asn Ser
            755                 760                 765

Phe Ser Asn Leu Asp Phe Asp Phe Leu Asp Ile Gln Asn Met Lys Lys
        770                 775                 780

Leu Phe Asn Ser Tyr Thr Glu Leu Leu Ile Lys Glu Gln Thr Ser Pro
785                 790                 795                 800

Tyr Glu Leu Ser Leu Tyr Ala Phe Gln Glu Gln Asp Asn Asn Val Ile
                805                 810                 815

Gly Asp Thr Ser Gly Lys Asn Thr Leu Val Glu Tyr Pro Lys Asp Ile
            820                 825                 830

Gly Leu Val Tyr Gly Ile Asn Asn Ala Ile His Leu Thr Gly Ala
            835                 840                 845

Asn Gln Asn Ile Lys Phe Thr Asn Asp Tyr Phe Glu Asn Gly Leu Thr
        850                 855                 860

Asn Asn Phe Ser Ile Tyr Phe Trp Leu Arg Asn Leu Asn Gln Asn Thr
865                 870                 875                 880

Ile Lys Ser Lys Leu Ile Gly Ser Lys Glu Asp Asn Cys Gly Trp Glu
            885                 890                 895

Ile Tyr Phe Glu Asn Asn Gly Leu Val Phe Asn Ile Ile Asp Ser Asn
                900                 905                 910

Gly Asn Glu Lys Asn Ile Tyr Leu Ser Asn Ile Ser Asn Lys Ser Trp
        915                 920                 925

His Tyr Ile Val Ile Ser Ile Asn Arg Leu Lys Asp Gln Leu Leu Ile
        930                 935                 940

Phe Ile Asp Asn Ile Leu Val Ala Asn Glu Asp Ile Lys Glu Ile Leu
945                 950                 955                 960

Asn Ile Tyr Ser Ser Asp Ile Ile Ser Leu Leu Ser Asp Asn Asn
            965                 970                 975

Val Tyr Ile Glu Gly Leu Ser Val Leu Asn Lys Thr Ile Asn Ser Asn
```

```
                   980             985             990
Glu Ile Leu Thr Asp Tyr Phe Ser Asp Leu Asn Asn Ser Tyr Ile Arg
                995            1000            1005

Asn Phe Asp Glu Glu Ile Leu Gln Tyr Asn Arg Thr Tyr Glu Leu
   1010            1015            1020

Phe Asn Tyr Val Phe Pro Glu Ile Ala Ile Asn Lys Ile Glu Gln
   1025            1030            1035

Asn Asn Asn Ile Tyr Leu Ser Asn Asn Asn Glu Asn Ser Leu Asn
   1040            1045            1050

Phe Lys Pro Leu Lys Phe Lys Leu Leu Asn Thr Asn Pro Asn Lys
   1055            1060            1065

Gln Tyr Val Gln Lys Trp Asp Glu Val Ile Phe Ser Val Leu Asp
   1070            1075            1080

Gly Thr Glu Lys Tyr Leu Asp Ile Ser Ile Asp Asn Asn Arg Ile
   1085            1090            1095

Gln Leu Val Asp Asn Lys Asn Asn Ala Lys Thr Phe Ile Ile Asn
   1100            1105            1110

Asn Asp Ile Phe Ile Ser Asn Cys Leu Thr Leu Thr Tyr Asn Asn
   1115            1120            1125

Val Asn Val Tyr Leu Ser Ile Lys Asn Gln Asp Tyr Asn Trp Val
   1130            1135            1140

Ile Cys Asp Leu Asn His Asp Ile Pro Lys Lys Ser Tyr Leu Trp
   1145            1150            1155

Ile Leu Lys Asn Ile
   1160

<210> SEQ ID NO 28
<211> LENGTH: 1165
<212> TYPE: PRT
<213> ORGANISM: Clostridium botulinum

<400> SEQUENCE: 28

Met Lys Ile Asn Asp Asp Leu Asn Ile Asn Ser Pro Val Asp Asn Lys
1               5                   10                  15

Asn Val Val Ile Val Arg Ala Arg Lys Thr Asn Ile Phe Phe Lys Ala
            20                  25                  30

Phe Gln Val Ala Pro Asn Ile Trp Val Ala Pro Glu Arg Tyr Tyr Gly
        35                  40                  45

Glu Pro Leu Asn Ile Ser Asp Gln Glu Lys Ser Asp Gly Gly Ile Tyr
    50                  55                  60

Asp Glu Asn Phe Leu Lys Glu Asn Ser Glu Lys Glu Phe Leu Gln
65                  70                  75                  80

Ala Ile Ile Leu Leu Lys Arg Ile Asn Asn Asn Ile Ile Gly Gln
                85                  90                  95

Lys Leu Leu Ser Leu Met Cys Thr Ser Ile Pro Phe Leu His Glu Tyr
            100                 105                 110

Lys Gln Gly Asp Tyr Arg Gln Ser Asn Tyr Leu Gly Ser Lys Asn Ser
        115                 120                 125

Glu Tyr Leu Tyr Ser Ala Asn Ile Val Ile Phe Gly Pro Gly Ser Asn
    130                 135                 140

Ile Val Lys Asn Asn Thr Ile Tyr Tyr Lys Lys Asn Phe Ala Glu Asn
145                 150                 155                 160

Gly Met Gly Thr Met Ala Glu Ile Leu Phe Gln Pro Phe Leu Thr Tyr
                165                 170                 175
```

-continued

```
Lys Tyr Asn Gln Phe Tyr Ala Asp Pro Ala Leu Glu Leu Ile Lys Cys
            180                 185                 190

Leu Ile Lys Ala Ile Tyr Phe Leu Tyr Gly Ile Lys Pro Asn Asp Asn
        195                 200                 205

Leu Asn Ile Pro Tyr Arg Leu Arg Asn Glu Phe Ser Asn Val Glu Tyr
    210                 215                 220

Ser Glu Leu Asn Ile Ile Asp Phe Leu Ile Ser Gly Ile Asp Tyr
225                 230                 235                 240

Lys Phe Ile Asn Thr Asn Pro Tyr Trp Phe Ile Asp Asn Tyr Phe Ile
                245                 250                 255

Asp Val Pro Lys Val Phe Glu Lys His Lys Asn Asp Tyr Glu Ile Asn
            260                 265                 270

Ile Lys Asn Asn Ser Glu Ile Gly Thr Ser Ile Lys Leu Tyr Leu Glu
        275                 280                 285

Gln Lys Phe Lys Thr Asn Val Gln Asp Ile Trp Glu Leu Asn Leu Ser
    290                 295                 300

Tyr Phe Ser Lys Glu Phe Gln Ile Met Met Pro Glu Lys His Asn Asn
305                 310                 315                 320

Ala Leu Lys His Tyr Tyr Arg Lys Glu Tyr Tyr Lys Ile Asn Tyr Ser
                325                 330                 335

Lys Gln Tyr Asp Ile Asn Gly Phe Val Asn Gly Gln Ile Ala Thr Lys
            340                 345                 350

Leu Leu Leu Ser Glu Lys Asn Gln Tyr Ile Ile Asn Lys Pro Gln Leu
        355                 360                 365

Ile Ile Asn Leu Ile Asn Lys Ser Asn Asn Ser Leu Leu Met Lys Ser
    370                 375                 380

Asn Ile Tyr Gly Asp Gly Leu Asn Gly Thr Thr Asp Asn Phe Tyr Arg
385                 390                 395                 400

Asn Tyr Lys Ile Pro Asp Asn Ile Ala Tyr Gln Tyr His Pro Asn Asn
                405                 410                 415

Thr Tyr Leu Asp Asn Val Asn Ile Glu Glu Ile Asn Asn Ile Pro Gln
            420                 425                 430

Ile Thr Asp Ala Asp Ile Tyr Pro Tyr Thr Asn Asn Cys Asp Thr Phe
        435                 440                 445

Ile Pro Ile Tyr Asn Ile Thr Gln Ser Arg Glu Ile Asn Thr Thr Val
    450                 455                 460

Pro Tyr Ser Ile Asn Tyr Leu Gln Ser Gln Ile Met Asn Ser Asp Asp
465                 470                 475                 480

Ile Thr Leu Ser Ser Asp Phe Trp Glu Val Val Cys Ser Asn Asp Lys
                485                 490                 495

Ser Leu Val Tyr Ser Tyr Leu Asp Asn Val Ile Asn Tyr Leu Asp Ser
            500                 505                 510

Ile Lys Asn Asn Thr Pro Ile Asn Thr Asp Lys Lys Tyr Tyr Leu Trp
        515                 520                 525

Leu Lys Glu Ile Phe Arg Asn Tyr Ser Phe Asp Ile Thr Ala Thr Glu
    530                 535                 540

Glu Ile Thr Thr Glu Cys Gly Ile Asn Lys Ile Val Ser Trp Phe Gly
545                 550                 555                 560

Lys Ala Phe Asn Ile Leu Asn Thr Asp Asn Ser Phe Lys Ile Glu Phe
                565                 570                 575

Gln Asn Ser Gly Ala Ile Ala Leu Ile Asn Lys Lys Asp Asn Ile Ile
            580                 585                 590

Ile Pro Lys Ile Glu Ile Asp Glu Met Pro Asn Ser Met Leu Asn Leu
```

```
                595                 600                 605
Ser Phe Glu Asp Leu Asn Glu Gln Leu Tyr Ser Ile Tyr Ser Lys Asn
610                 615                 620

Ile Thr Tyr Phe Lys Lys Ile Tyr Tyr Asn Phe Leu Asp Gln Trp Trp
625                 630                 635                 640

Thr Glu Tyr Tyr Ser Gln Tyr Phe Asp Leu Ile Cys Met Ala Lys Lys
                645                 650                 655

Ser Ile Leu Ala Gln Glu Asn Leu Ile Lys Lys Ile Gln Lys Lys
                660                 665                 670

Ile Ser Tyr Leu Ile Gly Ala Ser Asn Ile Pro Asp Asp Ile Leu Ala
            675                 680                 685

Val Met Arg Leu Thr Thr Asn Thr Leu Arg Asp Ile Ser Val Glu
690                 695                 700

Ser Gln Ile Ala Met Asn Asn Leu Asn Asn Phe Leu Asn Lys Ala Ala
705                 710                 715                 720

Met Cys Val Phe Gln Ser Asn Ile Tyr Pro Lys Phe Ile Ser Phe Met
                725                 730                 735

Glu Gln Cys Ile Lys His Ile Asn Lys Ser Thr Lys Glu Phe Ile Gln
                740                 745                 750

Lys Cys Thr Asn Ile Asn Glu Thr Glu Lys Leu Gln Leu Ile Met Gln
            755                 760                 765

Asn Ser Phe Ser Asn Leu Asp Phe Asp Phe Leu Asp Ile Gln Asn Met
770                 775                 780

Lys Asn Leu Phe Asn Ser Tyr Thr Glu Leu Leu Ile Lys Glu Gln Thr
785                 790                 795                 800

Ser Pro Tyr Glu Leu Ser Leu Tyr Ala Phe Glu Gln Asp Asn Asn
                805                 810                 815

Val Ile Gly Asp Ala Ser Gly Lys Asn Thr Leu Val Glu Tyr Pro Lys
                820                 825                 830

Gly Ile Glu Leu Val Tyr Gly Ile Asn Asn Ser Ala Leu Tyr Leu Asn
            835                 840                 845

Gly Ser Asn Gln Ser Ile Ile Phe Thr Asn Asp Tyr Phe Glu Asn Gly
850                 855                 860

Leu Thr Asn Ser Phe Ser Ile Tyr Phe Trp Leu Arg Asn Leu Gly Gln
865                 870                 875                 880

Asp Thr Ile Lys Ser Lys Leu Ile Gly Ser Lys Glu Tyr Asn Cys Gly
                885                 890                 895

Trp Glu Ile Tyr Phe Gln Glu Ile Gly His Val Phe Asn Met Ile Asp
            900                 905                 910

Ser Asn Gly Asn Glu Lys Asn Ile Tyr Leu Ser Asp Val Ser Asn Asn
            915                 920                 925

Ser Trp His Tyr Ile Thr Ile Ser Val Asp Arg Leu Lys Glu Gln Leu
930                 935                 940

Leu Ile Phe Ile Asp Asp Asn Leu Val Val Asn Glu Ser Ile Lys Asp
945                 950                 955                 960

Ile Leu Asn Ile Tyr Ser Ser Asn Ile Ile Ser Leu Ser Asp Asn
                965                 970                 975

Lys Ala Ser Tyr Ile Glu Gly Leu Thr Ile Leu Asn Lys Pro Thr Thr
            980                 985                 990

Gly Glu Glu Val Leu Arg Asn Tyr  Phe Lys Asn Leu Asn  Asn Ser Tyr
            995                 1000                1005

Val Arg Asp Ser Asn Asp Glu  Arg Leu Glu Tyr Asn  Lys Thr Tyr
     1010                1015                1020
```

```
Gln Leu Tyr Asp Tyr Val Phe Pro Asp Asn Pro Ile Cys Glu Val
    1025                1030                1035

Lys Gln Asp Asn Asn Ile Tyr Leu Thr Ile Asn Asn  Ile Asn Asn
    1040                1045                1050

Leu Asn Met Lys Pro Cys Lys Phe Lys Leu Leu Ser  Ile Asn Ser
    1055                1060                1065

Asn Lys Gln Tyr Val Gln Lys Trp Asp Glu Val Ile  Ile Ser Val
    1070                1075                1080

Leu Tyr Asp Thr Glu Lys Tyr Val Cys Ile Ser Asn  Glu Asn Asn
    1085                1090                1095

Arg Val Lys Ile Ile Asp Asn Lys Ile Met Gln Val  Lys Phe Ile
    1100                1105                1110

Ile Ser Asn Asp Ile Phe Ile Ser Asn Cys Leu Thr  His Ala His
    1115                1120                1125

Asn Asn Lys Tyr Ile Cys Leu Ser Met Lys Asp Glu  Asn Tyr Asn
    1130                1135                1140

Trp Met Ile Cys Asn Asn Glu Ser Asn Ile Pro Lys  Lys Ala Tyr
    1145                1150                1155

Leu Trp Ile Leu Lys Glu Val
    1160                1165

<210> SEQ ID NO 29
<211> LENGTH: 1198
<212> TYPE: PRT
<213> ORGANISM: Clostridium botulinum

<400> SEQUENCE: 29

Met Lys Ile Asn Ser Asn Leu Thr Ile Asn Ser Pro Ile Asp Asn Lys
1               5                   10                  15

Asn Val Val Ile Val Arg Ala Arg Glu Thr Ser Lys Phe Phe Lys Ala
            20                  25                  30

Phe Lys Val Ala Pro Asn Ile Trp Val Ala Pro Glu Arg Tyr Tyr Gly
        35                  40                  45

Glu Ser Leu Ser Ile Glu Glu Ser Lys Lys Val Asn Gly Gly Val Tyr
    50                  55                  60

Asp Ser Asn Phe Leu Ser Gln Asn Asn Glu Lys Asp Lys Phe Leu Gln
65                  70                  75                  80

Ala Ile Ile Thr Leu Leu Lys Arg Ile Asn Ser Asn Ile Ala Gly Glu
                85                  90                  95

Lys Leu Leu Ser Leu Val Ser Thr Ala Ile Pro Phe Pro Tyr Gly Tyr
            100                 105                 110

Ile Gly Gly Gly Tyr Tyr Cys Pro Asn Ile Val Thr Phe Gly Ser Thr
        115                 120                 125

Ile Lys Tyr Asn Lys Lys Ile Asn Ser Leu Ile Ser Thr Thr Ile Pro
    130                 135                 140

Phe Pro Tyr Gly Gly Tyr Arg Glu Thr Asn Tyr Leu Ser Ser Lys Asp
145                 150                 155                 160

Thr Glu Asn Phe Tyr Ala Ala Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Ala Glu Ile Cys Phe Gln Pro Phe Leu Thr
        195                 200                 205

Tyr Lys Tyr Asp Gln Phe Tyr Val Asp Pro Ala Leu Glu Leu Met Glu
```

```
            210                 215                 220
Cys Leu Ile Lys Ser Leu Tyr Phe Leu Tyr Gly Ile Lys Pro Asn Asn
225                 230                 235                 240

Asn Leu Thr Val Pro Tyr Arg Leu Arg Asn Glu Leu Ser Asn Ile Glu
                245                 250                 255

Phe Ser Gln Leu Ser Ile Val Asp Leu Leu Ile Ser Gly Gly Ile Asp
                    260                 265                 270

Ser Lys Phe Ile Asn Thr Asp Pro Tyr Trp Phe Ile Asp Ser Tyr Phe
            275                 280                 285

Ser Asn Ala Lys Thr Thr Phe Glu Glu His Lys Ser Ile Tyr Glu Thr
            290                 295                 300

Glu Ile Lys Gly Asn Asn Ala Ile Gly Asn Asp Ile Lys Leu Arg Leu
305                 310                 315                 320

Lys Gln Lys Phe Gln Thr Thr Val His Asp Ile Trp Gln Leu Asn Leu
                325                 330                 335

Asp Tyr Phe Ser Lys Glu Phe Gln Ile Met Met Pro Tyr Arg Phe Asn
                340                 345                 350

Asn Ala Leu Lys Tyr Tyr Tyr Arg Lys Glu Tyr Tyr Lys Ile Asp Tyr
                355                 360                 365

Pro Glu Lys Tyr Ser Ile Ala Gly Phe Val Asp Gly Gln Leu Asn Thr
370                 375                 380

Gln Leu Ser Leu Ser Asp Lys Asn Gln Tyr Ile Ile Asn Lys Pro Glu
385                 390                 395                 400

Leu Ile Val Asn Leu Ile Ser Glu Asn Asn Ile Ser Leu Met Arg Ser
                405                 410                 415

Asn Ile Tyr Gly Asp Gly Leu Lys Tyr Thr Thr Asp Asn Phe Tyr Ser
                420                 425                 430

Thr Tyr Lys Ile Pro Tyr Asn Arg Ala Tyr Glu Tyr His Phe Asn Asn
                435                 440                 445

Ser Ser Thr Ser Ser Leu Glu Asn Val Asn Val Glu Glu Ile Ser Asn
450                 455                 460

Ile Pro Glu Ile Ile Asp Ile Asn Pro Tyr Arg Glu Asn Ser Asp Ile
465                 470                 475                 480

Phe Ser Pro Val Glu Asn Ile Ile Glu Thr Lys Glu Val Asn Thr Lys
                485                 490                 495

Thr Pro Trp Pro Ile Asn Tyr Leu Gln Ala Gln Ile Pro Asn Asn Glu
                500                 505                 510

Glu Phe Thr Leu Ser Ser Asp Phe Ser Gln Val Val Ser Tyr Lys Thr
            515                 520                 525

Gln Ser Leu Val Tyr Ser Phe Leu Ser Asn Val Ile Ser Tyr Leu Asp
            530                 535                 540

Ser Val Lys Asp Thr Asn Pro Ile Asp Thr Asp Glu Lys Tyr Tyr Leu
545                 550                 555                 560

Trp Leu Arg Glu Ile Phe Arg Asn Tyr Ser Phe Asp Ile Thr Ala Ile
                565                 570                 575

Glu Glu Ile Asn Thr Ser Cys Gly Ile Asn Lys Val Val Ser Trp Phe
                580                 585                 590

Gly Lys Ala Leu Asn Ile Leu Asn Thr Ser Asn Ser Phe Val Lys Glu
            595                 600                 605

Phe Lys Asn Leu Gly Pro Ile Ser Leu Ile Asn Lys Lys Glu Asn Leu
            610                 615                 620

Ser Met Pro Ile Ile Glu Val Asn Glu Ile Pro Asn Asp Met Leu Gly
625                 630                 635                 640
```

```
Leu Ser Leu Lys Asp Leu Asn Glu Lys Leu Phe Asn Ile Tyr Leu Lys
            645                 650                 655
Asn Ile Leu Tyr Phe Lys Lys Val Tyr Phe Ser Phe Leu Asp Gln Trp
            660                 665                 670
Trp Thr Glu Tyr Tyr Ser Gln Tyr Phe Gly Leu Ile Cys Met Ala Lys
            675                 680                 685
Gln Ser Ile Leu Ala Gln Glu Asn Leu Ile Lys Lys Ile Val Gln Lys
            690                 695                 700
Lys Leu Ser Asp Leu Ser Lys Gln Ser Asn Ile Ser Asn Glu Lys Leu
705                 710                 715                 720
Asn Leu Met Asn Leu Thr Thr Glu Lys Thr Phe Ile Asp Leu Ser Asn
            725                 730                 735
Gln Ser Gln Ile Ala Met Asn Asn Ile Asn Asn Phe Leu Asn Lys Ala
            740                 745                 750
Ala Ile Cys Val Phe Glu Ser Asn Ile Tyr Pro Lys Phe Ile Ser Phe
            755                 760                 765
Met Glu Gln Tyr Ile Asn Asn Ile Asn Ile Lys Thr Thr Ala Phe Ile
            770                 775                 780
Arg Lys Cys Thr Asn Ile Thr Glu Lys Glu Lys Leu Gln Leu Ile Asn
785                 790                 795                 800
Gln Asn Thr Phe Asn Asn Leu Asp Phe Glu Phe Phe Asp Ile Gln Thr
            805                 810                 815
Ile Glu Asn Leu Leu Thr Ser Glu Thr Asn Leu Ile Ile Lys Glu Lys
            820                 825                 830
Thr Ser Pro Tyr Asp Leu Leu Leu Phe Ser Leu Gln Glu Ala Asp Arg
            835                 840                 845
Lys Val Ile Lys Asp Ile Ser Gly Lys Asp Thr Leu Val Gln Tyr Ser
            850                 855                 860
Asp Thr Ile Asp Leu Ser Tyr Gly Val Asn Gly Asp Ala Leu Tyr Leu
865                 870                 875                 880
Lys Glu Pro Asn Gln Ser Val Asn Phe Ser Asn Asn Ile Phe Glu Asn
            885                 890                 895
Gly Leu Thr Asn Ser Phe Ser Ile Cys Phe Trp Leu Arg Asn Leu Gly
            900                 905                 910
Gln Asp Asn Leu Ser Ser Asn Leu Ile Gly Asn Ile Val Asn Asn Cys
            915                 920                 925
Gly Trp Gln Ile Tyr Phe Glu Asn Asn Gly Leu Val Phe Ser Met Val
            930                 935                 940
Asp Cys Asn Gly Asn Glu Lys Asn Ile Tyr Leu Ser Asp Val Leu Ser
945                 950                 955                 960
Lys Tyr Trp Tyr Tyr Ile Ser Val Ser Val Asp Arg Leu Arg Asn Lys
            965                 970                 975
Leu Leu Ile Phe Ile Asn Asp Lys Leu Ile Val Asn Glu Ser Ile Glu
            980                 985                 990
Gln Ile Leu Asn Ile Tyr Ser Ser Asn Ile Ile Ser Leu Val Asn Glu
            995                 1000                1005
Asn Asn Pro Ile Cys Ile Glu Glu Leu Ser Ile Leu Asn Lys Ala
            1010                1015                1020
Leu Thr Ser Glu Glu Val Leu Asn Ser Tyr Phe Thr Asn Leu Asn
            1025                1030                1035
Asn Ser Tyr Ile Arg Asp Ser Tyr Gly Ala Arg Leu Glu Tyr Asn
            1040                1045                1050
```

```
Lys Asn Tyr Glu Leu Tyr Asn Tyr Val Phe Pro Glu Asn Ser Leu
    1055                1060                1065

Tyr Glu Val Ile Glu Asn Asn Met Tyr Leu Ser Ile Lys Asn
    1070                1075                1080

Ile Lys Asn Thr Asn Ile Leu Gly Ala Lys Phe Lys Leu Ile Asn
    1085                1090                1095

Thr Asp Glu Ser Lys Gln Tyr Val Gln Lys Trp Asp Glu Val Ile
    1100                1105                1110

Ile Cys Val Leu Gly Asp Thr Glu Lys Tyr Ala Asp Ile Gln Ala
    1115                1120                1125

Gly Asn Asn Arg Ile Gln Leu Val Asn Ser Lys Asp Asn Ala Arg
    1130                1135                1140

Lys Ile Ile Val Asn Asn Asn Ile Phe Arg Pro Asn Cys Val Leu
    1145                1150                1155

Phe Ser Tyr Asn Asn Lys Tyr Leu Ser Leu Ser Leu Arg Asn Arg
    1160                1165                1170

Asn Tyr Asn Trp Met Ile Cys Asn Asp Asn Ser Phe Ile Pro Lys
    1175                1180                1185

His Ala His Leu Trp Ile Leu Lys Lys Ile
    1190                1195

<210> SEQ ID NO 30
<211> LENGTH: 1163
<212> TYPE: PRT
<213> ORGANISM: Clostridium botulinum

<400> SEQUENCE: 30

Met Lys Ile Asn Gly Asn Leu Asn Ile Asp Ser Pro Val Asp Asn Lys
1               5                   10                  15

Asn Val Ala Ile Val Arg Ser Arg Lys Ser Asp Val Phe Phe Lys Ala
            20                  25                  30

Phe Gln Val Ala Pro Asn Ile Trp Ile Val Pro Glu Arg Tyr Tyr Gly
        35                  40                  45

Glu Ser Leu Lys Ile Asn Glu Asp Gln Lys Phe Asp Gly Gly Ile Tyr
    50                  55                  60

Asp Ser Asn Phe Leu Ser Thr Asn Glu Lys Asp Asp Phe Leu Gln
65                  70                  75                  80

Ala Thr Ile Lys Leu Leu Gln Arg Ile Asn Asn Asn Val Val Gly Ala
                85                  90                  95

Lys Leu Leu Ser Leu Ile Ser Thr Ala Ile Pro Phe Pro Tyr Glu Asn
            100                 105                 110

Asn Thr Glu Asp Tyr Arg Gln Thr Asn Tyr Leu Ser Ser Lys Asn Asn
        115                 120                 125

Glu His Tyr Tyr Thr Ala Asn Leu Val Ile Phe Gly Pro Gly Ser Asn
    130                 135                 140

Ile Ile Lys Asn Asn Val Ile Tyr Tyr Lys Lys Glu Tyr Ala Glu Ser
145                 150                 155                 160

Gly Met Gly Thr Met Leu Glu Ile Trp Phe Gln Pro Phe Leu Thr His
                165                 170                 175

Lys Tyr Asp Glu Phe Tyr Val Asp Pro Ala Leu Glu Leu Ile Lys Cys
            180                 185                 190

Leu Ile Lys Ser Leu Tyr Tyr Leu Tyr Gly Ile Lys Pro Asn Asp Asn
        195                 200                 205

Leu Asn Ile Pro Tyr Arg Leu Arg Asn Glu Phe Asn Ser Leu Glu Tyr
    210                 215                 220
```

```
Ser Glu Leu Asp Met Ile Asp Phe Leu Ile Ser Gly Gly Ile Asp Tyr
225                 230                 235                 240

Lys Leu Leu Asn Thr Asn Pro Tyr Trp Phe Ile Asp Lys Tyr Phe Ile
                245                 250                 255

Asp Thr Ser Lys Asn Phe Glu Lys Tyr Lys Asn Asp Tyr Glu Ile Lys
            260                 265                 270

Ile Lys Asn Asn Asn Tyr Ile Ala Asn Ser Ile Lys Leu Tyr Leu Glu
        275                 280                 285

Gln Lys Phe Lys Ile Asn Val Lys Asp Ile Trp Glu Leu Asn Leu Ser
    290                 295                 300

Tyr Phe Ser Lys Glu Phe Gln Ile Met Met Pro Glu Arg Tyr Asn Asn
305                 310                 315                 320

Ala Leu Asn His Tyr Tyr Arg Lys Glu Tyr Tyr Val Ile Asp Tyr Phe
                325                 330                 335

Lys Asn Tyr Asn Ile Asn Gly Phe Lys Asn Gly Gln Ile Lys Thr Lys
            340                 345                 350

Leu Pro Leu Ser Lys Tyr Asn Lys Glu Ile Ile Asn Lys Pro Glu Leu
        355                 360                 365

Ile Val Asn Leu Ile Asn Gln Asn Asn Thr Val Leu Met Lys Ser Asn
370                 375                 380

Ile Tyr Gly Asp Gly Leu Lys Gly Thr Val Asp Asn Phe Tyr Ser Asn
385                 390                 395                 400

Tyr Ile Ile Pro Tyr Asn Leu Asn Tyr Glu His Ser Ile Asn Tyr Ser
                405                 410                 415

Tyr Leu Asp Asn Val Asn Ile Glu Glu Ile Glu Lys Ile Pro Pro Ile
            420                 425                 430

Asn Asp Glu Asp Ile Tyr Pro Tyr Arg Lys Asn Ala Asp Thr Phe Ile
        435                 440                 445

Pro Val Tyr Asn Ile Thr Lys Ala Lys Glu Ile Asn Thr Thr Thr Pro
    450                 455                 460

Leu Pro Val Asn Tyr Leu Gln Ala Gln Met Ile Asp Ser Asn Asp Ile
465                 470                 475                 480

Asn Leu Ser Ser Asp Phe Leu Lys Val Ile Ser Ser Lys Gly Ser Leu
                485                 490                 495

Val Tyr Ser Phe Leu Asn Asn Thr Met Asp Tyr Leu Glu Phe Ile Lys
            500                 505                 510

Tyr Asp Lys Pro Ile Asp Thr Asp Lys Lys Tyr Tyr Lys Trp Leu Lys
        515                 520                 525

Ala Ile Phe Arg Asn Tyr Ser Leu Asp Ile Thr Glu Thr Gln Glu Ile
    530                 535                 540

Ser Asn Gln Phe Gly Asp Thr Lys Ile Ile Pro Trp Ile Gly Arg Ala
545                 550                 555                 560

Leu Asn Ile Leu Asn Thr Asn Asn Ser Phe Val Glu Glu Phe Lys Asn
                565                 570                 575

Leu Gly Pro Ile Ser Leu Ile Asn Lys Lys Glu Asn Ile Thr Ile Pro
            580                 585                 590

Lys Ile Lys Ile Asp Glu Ile Pro Ser Ser Met Leu Asn Phe Ser Phe
        595                 600                 605

Lys Asp Leu Ser Glu Asn Leu Phe Asn Ile Tyr Cys Lys Asn Asn Phe
    610                 615                 620

Tyr Leu Lys Lys Ile Tyr Tyr Asn Phe Leu Asp Gln Trp Trp Thr Gln
625                 630                 635                 640
```

```
Tyr Tyr Ser Gln Tyr Phe Asp Leu Ile Cys Met Ala Ser Lys Ser Val
                645                 650                 655

Leu Ala Gln Glu Lys Leu Ile Lys Lys Leu Ile Gln Lys Gln Leu Arg
            660                 665                 670

Tyr Leu Met Glu Asn Ser Asn Ile Ser Ser Thr Asn Leu Ile Leu Ile
            675                 680                 685

Asn Leu Thr Thr Thr Asn Thr Leu Arg Asp Ile Ser Asn Gln Ser Gln
        690                 695                 700

Ile Ala Ile Asn Asn Ile Asp Lys Phe Phe Asn Ala Ala Met Cys
705                 710                 715                 720

Val Phe Glu Asn Asn Ile Tyr Pro Lys Phe Thr Ser Phe Met Glu Gln
            725                 730                 735

Cys Ile Lys Asn Ile Asn Lys Ser Thr Lys Glu Phe Ile Leu Lys Cys
            740                 745                 750

Thr Asn Ile Asn Glu Thr Glu Lys Ser His Leu Ile Met Gln Asn Ser
            755                 760                 765

Phe Ser Asn Leu Asp Phe Asp Phe Leu Asp Ile Gln Asn Met Lys Asn
        770                 775                 780

Leu Phe Asn Ser Tyr Thr Glu Leu Leu Ile Lys Glu Gln Thr Ser Pro
785                 790                 795                 800

Tyr Glu Leu Ser Leu Tyr Ala Phe Gln Glu Gln Asp Asn Asn Val Ile
            805                 810                 815

Gly Asp Thr Ser Gly Lys Asn Thr Leu Val Glu Tyr Pro Lys Asp Ile
            820                 825                 830

Gly Leu Val Tyr Gly Ile Asn Asn Asn Ala Ile His Leu Thr Gly Ala
            835                 840                 845

Asn Gln Asn Ile Lys Phe Thr Asn Asp Tyr Phe Glu Asn Gly Leu Thr
        850                 855                 860

Asn Asn Phe Ser Ile Tyr Phe Trp Leu Arg Asn Leu Lys Gln Asn Thr
865                 870                 875                 880

Ile Lys Ser Lys Leu Ile Gly Ser Lys Glu Asp Asn Cys Gly Trp Glu
            885                 890                 895

Ile Tyr Phe Glu Asn Asp Gly Leu Val Phe Asn Ile Ile Asp Ser Asn
            900                 905                 910

Gly Asn Glu Lys Asn Ile Tyr Leu Ser Asn Ile Ser Asn Asn Ser Trp
        915                 920                 925

His Tyr Ile Val Ile Ser Ile Asn Arg Leu Lys Asp Gln Leu Leu Ile
        930                 935                 940

Phe Ile Asp Asn Ile Leu Val Ala Asn Glu Asp Ile Lys Glu Ile Leu
945                 950                 955                 960

Asn Ile Tyr Ser Ser Asp Ile Ile Ser Leu Leu Ser Asp Asn Asn
            965                 970                 975

Val Tyr Ile Glu Gly Leu Ser Val Leu Asn Lys Thr Ile Asn Ser Asn
            980                 985                 990

Glu Ile Leu Thr Asp Tyr Phe Ser  Asp Leu Asn Asn Ser  Tyr Ile Arg
            995                 1000                1005

Asn Phe Asp Glu Glu Ile Leu  Gln Tyr Asn Arg Thr  Tyr Glu Leu
    1010                1015                1020

Phe Asn Tyr Val Phe Pro Glu  Ile Ala Ile Asn Lys  Ile Glu Gln
    1025                1030                1035

Asn Asn Asn Ile Tyr Leu Ser  Ile Asn Asn Glu Asn  Asn Leu Asn
    1040                1045                1050

Phe Lys Pro Leu Lys Phe Lys  Leu Leu Asn Thr Asn  Pro Asn Lys
```

```
              1055                1060                1065
Gln Tyr Val Gln Lys Trp Asp Glu Val Ile Phe Ser Val Leu Asp
        1070                1075                1080

Gly Thr Glu Lys Tyr Leu Asp Ile Ser Thr Thr Asn Asn Arg Ile
        1085                1090                1095

Gln Leu Val Asp Asn Lys Asn Asn Ala Gln Ile Phe Ile Ile Asn
        1100                1105                1110

Asn Asp Ile Phe Ile Ser Asn Cys Leu Thr Leu Thr Tyr Asn Asn
        1115                1120                1125

Val Asn Val Tyr Leu Ser Ile Lys Asn Gln Asp Tyr Asn Trp Val
        1130                1135                1140

Ile Cys Asp Leu Asn His Asp Ile Pro Lys Lys Ser Tyr Leu Trp
        1145                1150                1155

Ile Leu Lys Asn Ile
        1160
```